(12) United States Patent
Gellman et al.

(10) Patent No.: US 6,752,814 B2
(45) Date of Patent: *Jun. 22, 2004

(54) DEVICES FOR MINIMALLY INVASIVE PELVIC SURGERY

(75) Inventors: Barry N. Gellman, Easton, MA (US); Rodney Brenneman, San Juan Capistrano, CA (US); David Sauvageau, Methuen, MA (US); William Pintauro, Ft. Lauderdale, FL (US); Rodney Appell, Shaker Heights, OH (US); Armand A. Morin, Berkeley, MA (US)

(73) Assignee: SciMed Life Systems, Inc., Maple Grove, MN (US)

(*) Notice: Subject to any disclaimer, the term of this patent is extended or adjusted under 35 U.S.C. 154(b) by 230 days.

This patent is subject to a terminal disclaimer.

(21) Appl. No.: 10/015,114

(22) Filed: Nov. 12, 2001

(65) Prior Publication Data

US 2002/0055748 A1 May 9, 2002

Related U.S. Application Data

(63) Continuation of application No. 09/023,965, filed on Feb. 13, 1998, now Pat. No. 6,423,080.
(60) Provisional application No. 60/038,171, filed on Feb. 13, 1997.

(51) Int. Cl.[7] .............................................. A61B 17/04
(52) U.S. Cl. ...................................................... 606/148
(58) Field of Search .......................................... 606/148

(56) References Cited

U.S. PATENT DOCUMENTS

| | | | |
|---|---|---|---|
| 3,551,987 A | 1/1971 | Wilkinson | 29/212 |
| 3,575,163 A | 4/1971 | Gaspar | 128/17 |
| 3,744,481 A | 7/1973 | McDonald | 128/6 |
| 3,762,400 A | 10/1973 | McDonald | 128/18 |
| 4,935,027 A | 6/1990 | Yoon | 606/146 |
| 5,064,434 A | 11/1991 | Haber | 623/11 |
| 5,112,344 A | 5/1992 | Petros | 606/148 |
| 5,122,130 A | 6/1992 | Keller | 606/61 |
| 5,165,387 A | 11/1992 | Woodson | 128/6 |
| 5,179,937 A | 1/1993 | Lee | 128/17 |
| 5,237,985 A | 8/1993 | Hodgson et al. | 128/17 |
| 5,300,082 A | 4/1994 | Sharpe et al. | 606/147 |
| 5,308,349 A | 5/1994 | Mikhail | 606/88 |
| 5,330,496 A | 7/1994 | Alferness | 606/171 |
| 5,336,231 A * | 8/1994 | Adair | 606/148 |
| 5,397,330 A | 3/1995 | Mikhail | 606/88 |
| 5,437,603 A | 8/1995 | Cerny et al. | 600/29 |
| 5,462,560 A * | 10/1995 | Stevens | 606/144 |
| 5,536,251 A | 7/1996 | Evard et al. | 604/93 |
| 5,582,188 A | 12/1996 | Benderev et al. | 128/898 |
| 6,258,024 B1 | 7/2001 | van Der Weegen | 600/115 |

FOREIGN PATENT DOCUMENTS

| | | |
|---|---|---|
| EP | 0 417 031 A2 | 9/1990 |
| EP | 0407357 | 1/1991 |
| EP | 0 654 247 A1 | 10/1993 |
| GB | 2214814 | 9/1989 |
| WO | WO 94/12091 | 6/1994 |
| WO | WO 96/06567 | 3/1996 |
| WO | WO 96/28083 | 9/1996 |

OTHER PUBLICATIONS

"The Preiurethral Cutter Clamp", *Lone Star Medical Products, Inc. Catalog*, 2 pages.

Mitchell, "Hook Needle and Retractor for Posterior Urethroplasty." British Journal of Urology 42: 599–600 (1970).

* cited by examiner

*Primary Examiner*—Gary Jackson
(74) *Attorney, Agent, or Firm*—Ropes & Gray LLP

(57) ABSTRACT

Guide member placement devices are provided herein. The guide member placement devices of the invention are particularly useful for blunt dissection and introduction of a guide member into a body in a minimally invasive manner. The disclosed guide member placement devices are also useful in pelvic floor reconstruction procedures because they permit a surgeon to introduce a guide member beneath a urethra without puncturing the vaginal wall.

27 Claims, 76 Drawing Sheets

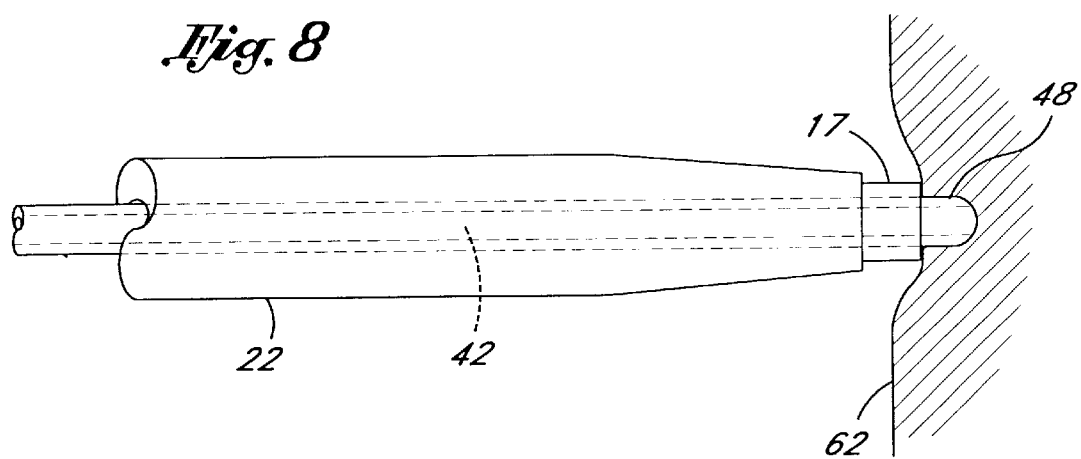

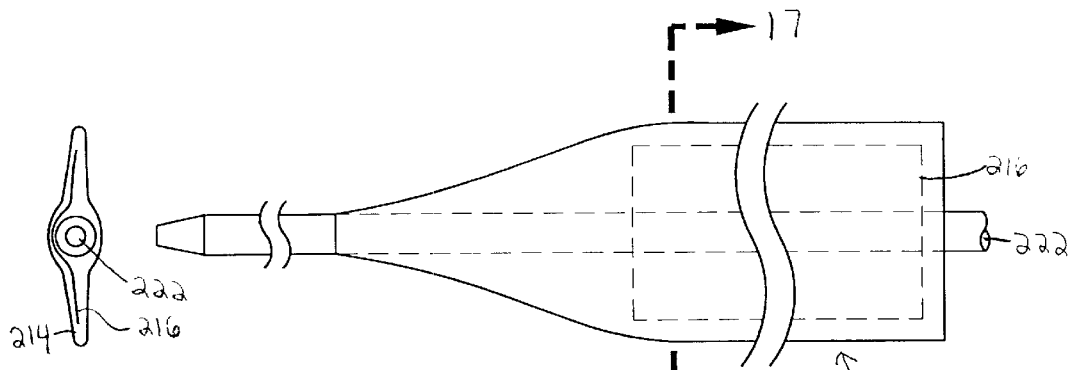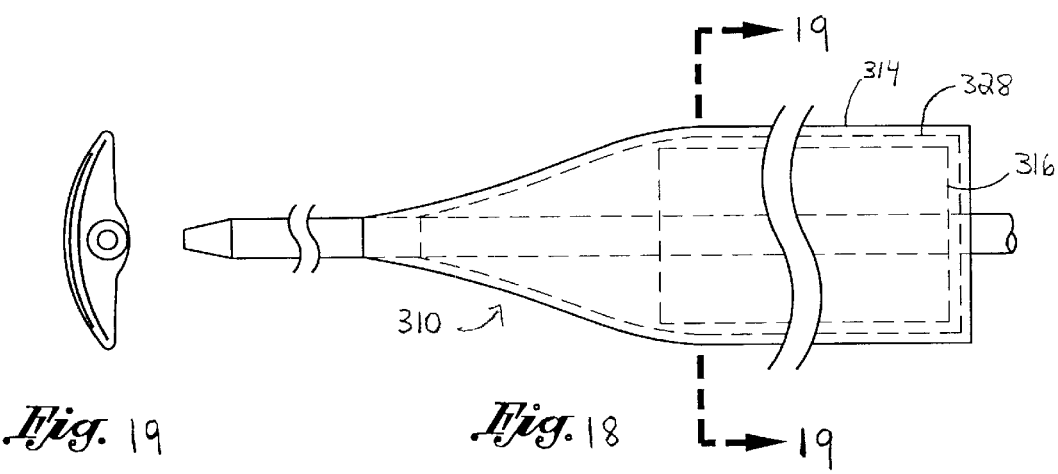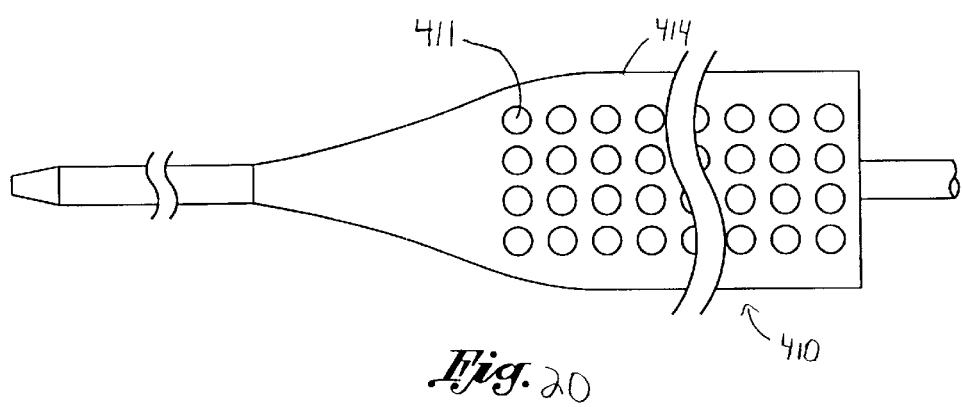

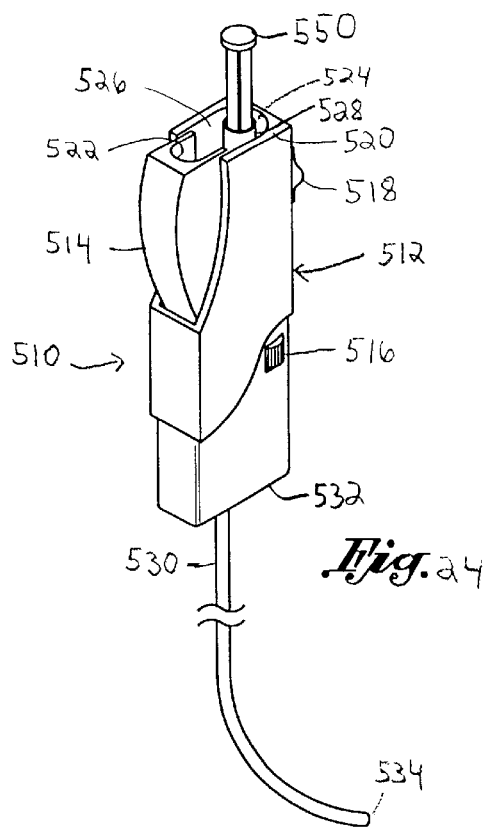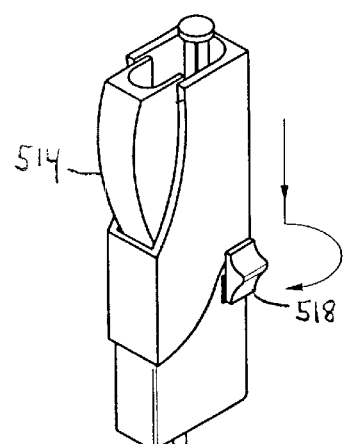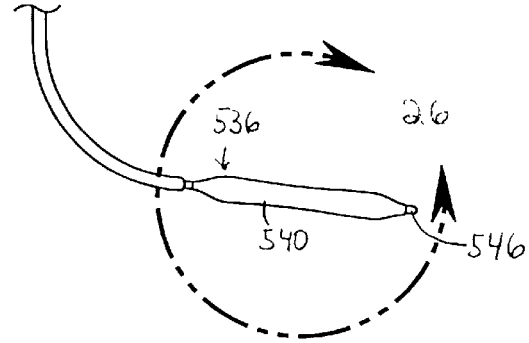
Fig. 24
Fig. 25

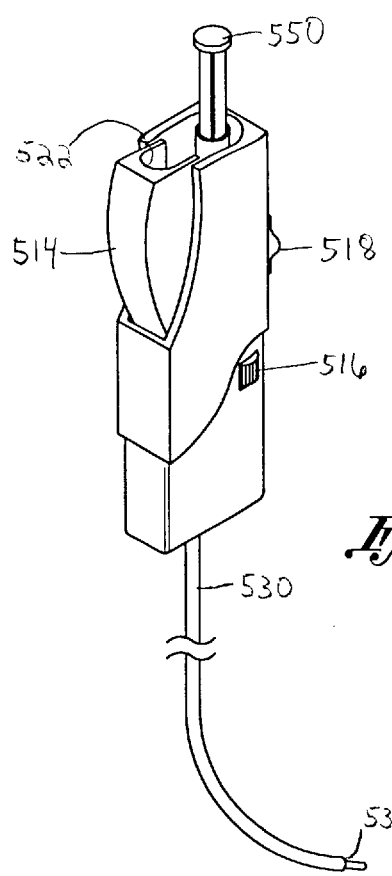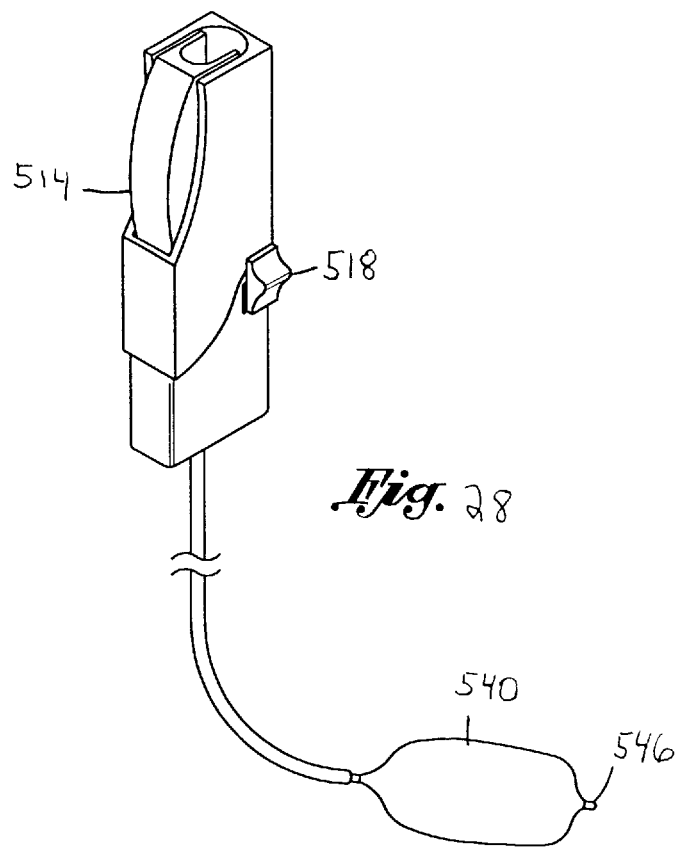

DEVICES FOR MINIMALLY INVASIVE PELVIC SURGERY

This is a continuation of prior application Ser. No. 09/023,965, filed on Feb. 13, 1998, which claims priority to Serial No. 60/038,171, the entire disclosures of which are incorporated by reference herein.

RELATED APPLICATIONS

This is a continuation of U.S. Ser. No. 09/023,965 filed Feb. 13, 1998, U.S. Pat. No. 6,423,080 which claims priority to U.S. Ser. No. 60/038,171, filed on Feb. 13, 1997, the disclosures of which are incorporated herein by reference.

FIELD OF THE INVENTION

The present invention relates to devices and methods for treating incontinence.

BACKGROUND OF THE INVENTION

Urinary incontinence is a widespread problem in the United States and throughout the world. Urinary incontinence affects people of all ages and can severely impact a patient both physiologically and psychologically.

In approximately 30% of the women suffering from urinary incontinence, incontinence is caused by intrinsic sphincter deficiency (ISD), a condition in which the valves of the urethral sphincter do not properly coapt. In approximately another 30% of incontinent women, incontinence is caused by hypermobility, a condition in which the muscles around the bladder relax, causing the bladder neck and proximal urethra to rotate and descend in response to increases in intraabdominal pressure. Hypermobility may be the result of pregnancy or other conditions which weaken the muscles. In an additional group of women with urinary incontinence, the condition is caused by a combination of ISD and hypermobility.

In addition to the conditions described above, urinary incontinence has a number of other causes, including birth defects, disease, injury, aging, and urinary tract infection.

Numerous approaches for treating urinary incontinence are available. For example, several procedures for stabilizing and/or slightly compressing the urethra so as to prevent the leakage of urine have been developed. The stabilizing or compressive force may be applied directly by sutures passing through the soft tissue surrounding the urethra or, alternatively, may be applied by means of a sling located under the urethra and suspended by sutures. The sutures may be anchored to the pubic bone by means of bone anchors or, alternatively, the sutures may be attached to other structures such as fascia.

A device for dissecting around a tubular structure such as the urethra or the bladder neck is available from Lone Star Medical Products. The Lone Star device has two shafts which can be positioned in the tissue between the urethra and the vaginal wall using cystoscopy, vaginal or rectal examination, or an examination of the position of the instrument around the urethra with the bladder opened. The two shafts can be locked together to pinch the intervening tissue. A sharp blade is inserted into one of the shafts and advanced into the second shaft, cutting the tissue in between the two shafts. The cut in the tissue can be expanded using a right angle clamp and an artificial sphincter guided by a suture attached to the cutting blade of the device can be introduced into the expanded cut.

With the Lone Star device, the distance between the two shafts cannot be gradually adjusted. In addition, the ends of the shafts of the Lone Star device come in direct contact with the tissue or bone while being advanced towards the tissue between the urethra and the upper vaginal wall. The shafts of the Lone Star device are flat at their distal ends.

Thus, there is a need for devices which simplify treatments for urinary incontinence and increase their safety. Sling application devices for treating urinary incontinence which reduce the risk of inadvertent pinching of the urethra and undesirable scoring of tissue or bone during advancement of the device would be particularly desirable. It is also desirable to have a sling application device that does not employ a guiding suture and can create or maintain an opening in the tissue between the urethra and the upper vaginal wall without the use of a right angle clamp, thereby simplifying the procedure.

U.S. Pat. No. 5,611,515, issued Mar. 18, 1997 to Benderev et al., introduces pioneering minimally invasive percutaneous and transvaginal bladder neck stabilization approaches. The percutaneous approach of Benderev et al. involves stabilizing the bladder neck using a bone anchor which is percutaneously introduced from the abdominal side of the patient. The transvaginal approach of Benderev et al. involves stabilizing the bladder neck using a staple or bone anchor which is transvaginally placed into the pubic bone. There is also a need for further devices and methods for improving or maintaining urinary continence involving stabilization or compression of the bladder neck or urethra, particularly devices and methods of the present invention that are less invasive than many of those currently available.

SUMMARY OF THE INVENTION

The present invention relates to devices and methods for use in percutaneous and hiatal approaches treatments for urinary incontinence. In particular, the present invention relates to guide member placement devices, sling application catheters, tissue dissectors/dilators, sling application devices and a sling application system, tissue expanders, grasping devices, and balloon catheters. Methods for using the preceding devices to stabilize the bladder neck or the urethral floor in order to maintain or improve urinary continence are also disclosed.

One aspect of the present invention is a guide member placement device for inserting a guide member in a body tissue. The guide member placement device comprises a shaft having a proximal end, a distal end, and a lumen extending therethrough. The lumen of the shaft is adapted for receiving a guidemember. The distal end of the shaft has an engaging member for engaging another guide member placement device. In one embodiment of the guide member placement device, the device further comprises a blunt dissection tip at the distal end of the shaft and a handle with a lumen extending therethrough wherein the lumen of the shaft and the lumen of the handle are aligned. In a further embodiment, the blunt dissection tip is on a blunt dissector within the shaft and is extendable from and retractable in the shaft. In a further embodiment, the guide member placement device is adapted for use in urethral floor reconstruction procedures. In yet another embodiment, the guide member placement device is adapted for use in bladder neck stabilization procedures. In one embodiment of the guide member placement device, the engaging member comprises a male connector. In another embodiment of the guide member placement device, the engaging member comprises a female connector. In yet another embodiment of the guidemember placement device, the shaft has a straight proximal section, a bent intermediate section and a distal end oriented at an angle of approximately 90 degrees relative to the proximal section. In another embodiment, the guide member placement device further comprises a guide member removably positioned in the lumen of the shaft. In one aspect of this embodiment, the guide member comprises a guide wire. In another aspect of this embodiment, the guide member comprises a suture.

Another aspect of the present invention is a method of inserting a guide member into a body tissue. A shaft of a first guide member placement device is inserted percutaneously and advanced through the body tissue to a central point through which the guide member will pass. A shaft of a second guide member placement device is inserted percutaneously and advanced through the body tissue to the central point through which the guide member will pass. An engaging member on a distal end of the shaft of the first guide member placement device is coupled to an engaging member on a distal end of a shaft of a second guide member placement device such that a lumen in the shaft of the first guide member placement device is fluid communication with a lumen in the shaft of the second guide member placement device. A guide member is passed through the lumens of the coupled shafts of the first guide member placement device and the second guide member placement device. The shaft of the first guide member placement device and the shaft of the second guide member placement device are removed from the body, thereby leaving the guide member in the body tissue. In one embodiment of the method, the first and second shafts are percutaneously inserted through first and second suprapubic incisions. In another embodiment of the method, the shafts of the first and second guide member placement devices are inserted into a pre-formed opening or pocket in the body tissue. In another embodiment of the method, the method further comprises the step of creating an opening in the body tissue by extending and retracting a blunt dissector tip from at least one of the guide member placement devices. In another embodiment of the method, the pre-formed opening or pocket is in the tissue between the urethra and the upper vaginal wall such that the guide member is left in the pre-formed opening or pocket.

Another aspect of the present invention is a sling application catheter comprising a catheter having a sling therein, where the sling is releasably engaged with the catheter. In one embodiment of the sling application catheter, the catheter has a pouch therein for releasably engaging the sling. In some embodiments, the catheter is adapted to travel over a guide member. In yet another embodiment of the sling application catheter, the distal end of the catheter is tapered. In yet another embodiment of the sling application catheter, the distal end of the pouch is tapered. In one embodiment of the sling application catheter, the pouch is porous. In another embodiment of the sling application catheter, the pouch further comprises a stiffener for increasing its rigidity. The stiffener may be in the interior of the pouch or on the exterior of the pouch. In another embodiment of the sling application catheter, the stiffener is porous.

Another aspect of the present invention is a method of introducing a sling into a body tissue. The method comprises the steps of passing a sling application catheter catheter through the body tissue. The sling application catheter comprises a catheter having a sling therein which is releasably engaged to the catheter. The sling is released form the sling application catheter, thereby introducing the sling into the body tissue.

In one aspect of the method of introducing a sling into a body tissue, the method further comprises making a first incision and a second incision and the step of passing the sling application catheter through the body tissue comprises passing the sling application catheter into the first incision and out of the second incision. In one embodiment of the method of introducing a sling into a body tissue, the sling is released from the sling application catheter by withdrawing the sling from a pouch in the sling application catheter. In another embodiment, the sling application catheter is passed through the body tissue over a guide member. In yet another embodiment, the sling is introduced into the tissue between the urethra and the upper vaginal wall. In still another embodiment, the first incision and the second incision are suprapubic incisions. In another embodiment, the method further comprises the step of withdrawing the sling from the pouch by grasping an end of the sling while withdrawing the distal end of the sling application catheter out of the second suprapubic incision. In yet another embodiment, the step of withdrawing the sling from the pouch comprises withdrawing a sterile sling.

Another aspect of the present invention is a tissue dissector/dilator for creating and dilating an opening or pocket in a body tissue. The tissue dissector/dilator comprises a body, a noncompliant shaft attached to the body, a dissector carried on the shaft for creating an opening or pocket in the body tissue, and a dilator carried on the shaft for dilating the opening or pocket in the body tissue. In one embodiment, the shaft has a lumen extending therethrough and the dissector is within the lumen in the shaft and is axially movable, such that the dissector can be extended from and retracted in the shaft. In another embodiment, the shaft has a lumen extending therethrough and the dilator is within the lumen in the shaft and is axially movable, such that the dilator can be extended from and retracted in said shaft. In another embodiment, the shaft has a lumen extending therethrough and both the dissector and the dilator are within the lumen of the shaft and are axially movable, such that the dissector and the dilator can be extended from and retracted in the shaft. In one embodiment, the axially movable dissector and the axially movable expandable dilator are integral. In another embodiment, the tissue dissector/dilator is adapted for use in bladder neck stabilization procedures.

In still another embodiment of the tissue dissector/dilator, the body of the tissue dissector/dilator further comprises a first control member for extending and retracting the axially movable integral dissector and expandable dilator between a first position in which the dissector extends from the shaft, a second position in which both the dissector and the dilator extend from the shaft, and a third position in which the dissector and the dilator are retracted inside the shaft. In this embodiment, the body of the tissue dissector/dilator also comprises a second control member for expanding the dilator in the opening or pocket in the body tissue, thereby dilating the opening or pocket and for collapsing the dilator following dilation of the opening or pocket. In another embodiment, the first control member for extending and retracting the axially movable integral dissector and expandable dilator comprises a spring return button which engages the axially movable integral dissector and expandable dilator so as to extend or retract said axially movable integral dissector and expandable dilator. In still another embodiment, the spring return button can be positioned to lock the axially movable integral dissector and expandable dilator in a fully extended position. In yet another embodiment, the spring return button provides a one to one stroke motion to the axially movable integral dissector and expandable dilator.

In a further embodiment of the tissue dissector/dilator, the axially movable integral dissector and expandable dilator is a catheter comprising an outer tube having a lumen extending therethrough and at least one expandable balloon in the lumen of the outer tube. In this embodiment, the expandable balloon has an inflation tube at its proximal end and a blunt dissector at its distal end, wherein the inflation tube is in fluid communication with the interior of the balloon. In still another embodiment, the second control member for expanding the dilator comprises a trigger on the body and a syringe in the body comprising a plunger, a reservoir, and a tip. In this embodiment, the tissue dissector/dilator also comprises a syringe locking mechanism, wherein the tip of the syringe fixedly engages the syringe locking mechanism to place the reservoir of the syringe in fluid communication with the balloon catheter, and the trigger engages the plunger of the syringe such that squeezing the trigger depresses the plunger of the syringe thereby dispensing fluid from the syringe and expanding the balloon of the catheter. In still another embodiment, the catheter further comprises a second lumen adapted for passage of a guide member. In a further embodiment, the catheter further comprises a third lumen. In another embodiment, the third lumen is adapted for receiving an ultrasound catheter. In still another embodiment, the third lumen is adapted for receiving an implant. In another embodiment, the third lumen is adapted for irrigation.

Another aspect of the present invention is a tissue dissector/dilator for creating and dilating an opening or pocket in a body tissue comprising a body, a noncompliant shaft attached to said body, a dissection means carried on the shaft for dissecting an opening or pocket in a body tissue, and a dilation means carried on the shaft for dilating the opening or pocket, Another aspect of the present invention is a method of creating and dilating an opening or pocket in a body tissue. A noncompliant shaft of a tissue dissector/dilator is percutaneously inserted into the body tissue. The shaft is advanced through the body tissue. A dissector is extended from a distal end of the shaft to create a first opening or pocket in the body tissue and a dilator is extended from the distal end of the shaft. The dilator is expanded within the first opening or pocket to dilate the first opening or pocket. In one embodiment of the method, the tissue dissector/dilator is percutaneously inserted through a suprapubic incision. In another embodiment, the body tissue is the tissue between the urethra and the upper vaginal wall and the first opening or pocket is perpendicular to the longitudinal axis of the urethra and extends from one side of the urethra to the other. In another embodiment the method further comprises percutaneously inserting a noncompliant shaft of a second tissue dissector/dilator into the body tissue, advancing the noncompliant shaft of the second tissue dissector/dilator through the body tissue, extending a dissector from a distal end of the shaft of the second tissue dissector/dilator to create a second opening or pocket in the tissue, extending a dilator from the distal end of the shaft of the second tissue dissector/dilator and expanding said dilator within the second opening or pocket, thereby dilating the second opening or pocket and forming from the first and second openings or pockets a continuous opening or pocket in the body tissue. In a further embodiment, the second tissue dissector/dilator is percutaneously inserted through a suprapubic incision. In yet another embodiment of the method, the body tissue is the tissue between the urethra and the upper vaginal wall and the continuous opening or pocket is perpendicular to the longitudinal axis of the urethra and extends from one side of the urethra to the other.

Another aspect of the present invention is a sling application device for inserting a sling into a pocket in a body tissue. The sling application device comprises a first shaft and a second shaft. The first and second shafts have lumens extending therethrough. The lumens have dimensions adapted for receiving a sling therein. The sling application device also comprises an adjuster for incrementally adjusting the distance between said first and second shafts. In one embodiment, the lumens of the first and second shafts have dimensions adapted for receiving a sling introducer having a sling releasably engaged thereto. In another embodiment, the sling application device further comprises a first handle attached to the first shaft and a second handle attached to the second shaft. In this embodiment, the first and second handles have openings therein which are in fluid communication with the lumens in the shafts to which the handles are attached and the first and second handles are adapted to be connected to one another. In another embodiment, the adjuster engages the first and second handles.

In one embodiment of the sling application device the first and second shafts are curved. In still another embodiment, the first and second shafts have a small radius 90° curve at their distal ends, such that the first and second shafts are adapted for use in urethral stabilization procedures. In another embodiment, the first and second shafts have a side bend. In yet another embodiment, the radius of curvature at the distal ends of the first and second shafts is not planar with the axial portions of the shafts of the first and second shafts. In still another embodiment, the upper edges of the distal ends of the first and second shafts are indented relative to the lower edges. In another embodiment, the first and second handles are adapted for interlocking. In a further embodiment, the adjuster comprises an articulating lock. In still another embodiment, the first shaft and the second shaft are cylindrical. In one embodiment, the first shaft and the second shaft comprise flat tubes. In another embodiment, the portion of the first shaft and the second shaft proximal to the bend is cylindrical and the portion distal to the bend is a flat tube. In another embodiment, the proximal portions of the first and second shafts are oriented at an angle of about 90° relative to the distal portions of the first and second shafts. In another embodiment, the sling application device further comprises a blunt dissector for dissecting the body tissue without scoring or creasing tissue or bone with which it comes in contact. In this embodiment, the blunt dissector comprises a dissector shaft adapted for insertion into the first and second shafts of the sling application device. The dissector shaft has a generally rigid tip at its distal end. The rigid tip protrudes from the distal ends of the first and second shafts of the sling application device when the blunt dissector is inserted into the first and second shafts of the sling application device. In yet another embodiment, the blunt dissector comprises an obturator.

Another aspect of the present invention is a sling introducer adapted for introducing a sling attached thereto into an opening or pocket in a body tissue without the use of sutures. The sling introducer comprises a sling engager having the sling releasably engaged thereto. The sling engager is adapted for advancement through a first shaft and a second shaft of a sling application device. The length of the sling introducer is at least equal to the sum of the lengths of the first and second shafts of the sling application device. In one embodiment, the sling engager comprises a pouch for releasably engaging said sling. In another embodiment, the pouch has pores therein for permitting a solution to access said sling. In still another embodiment, the distal end of the pouch has a narrow lead. In a further embodiment, the pouch is reinforced.

Another aspect of the present invention is a tissue cutter for forming a cavity in a tissue. The tissue cutter comprises an elongated housing adapted to fit within a shaft of a sling application device and an extendable and a retractable blade within the housing. The blade is adapted to form the cavity in the tissue. In one embodiment, the blade comprises a razor. In another embodiment, the razor is sized such that the cavity formed with the razor has dimensions adapted for insertion of a sling therein.

Another aspect of the present invention is a sling application system. The sling application system includes a sling application device comprising a first shaft and a second shaft. The first and second shafts of the sling application device have lumens extending therethrough. The lumens have dimensions adapted for receiving a sling introducer therein. The sling application device also comprises an adjuster for incrementally adjusting the distance between the first and second shafts. The sling application system also includes a blunt dissector for dissecting a body tissue without scoring or creasing tissue or bone with which it comes in contact. The blunt dissector comprises a dissector shaft adapted for insertion into the first and second shafts of the sling application device. The dissector shaft has a generally rigid tip at its distal end wherein the generally rigid tip protrudes from the distal ends of the first and second shafts of the sling application device when the blunt dissector is inserted into the first and second shafts. The sling application system also comprises a sling introducer for introducing a sling attached thereto into an opening or pocket in the body tissue without the use of sutures. The sling introducer comprises a sling engager having the sling releasably engaged thereto. The sling engager is adapted for advancement through the lumens of the first and second shafts of the sling application device wherein the sling introducer has a length sufficient to extend between the first and second shafts of the sling application device. In one embodiment, the sling application system further comprises a tissue cutter for forming a cavity in the body tissue. The tissue cutter comprises an elongated housing adapted to fit within the second shaft of the sling application device and an extendable and retractable blade within the housing. The blade is adapted to form a cavity in the body tissue.

Yet another aspect of the present invention is a method for introducing a sling into a body tissue. A first blunt dissector is inserted into a first shaft of a sling application device. The first shaft having the first blunt dissector therein is inserted percutaneously and advanced through the body tissue. A second blunt dissector is inserted into a second shaft of the sling application device. The second shaft having the second blunt dissector therein is inserted percutaneously and advanced through the body tissue. The distance between the distal ends of said first and second shafts is decreased. A sling introducer having the sling releasably engaged thereto is advanced between the first and second shafts of the sling application device. The sling is released from the sling introducer. The first and second shafts are removed from the body tissue, thereby introducing the sling into the body tissue. In one embodiment, the method further comprises making a first incision and a second incision wherein the first shaft of the sling application device is inserted into the first incision prior to advancing it through the body tissue and the second shaft of the sling application device is inserted into the second incision prior to advancing it through the body tissue. In another embodiment, the sling is introduced into a pre-formed pocket in the tissue between the urethra and the vaginal wall. In a further embodiment, the first incision and the second incision are suprapubic incisions. In still another embodiment, the method further comprises inserting a tissue cutter into the first shaft of the sling application device and extending the tissue cutter into the body tissue between the distal ends of the first and second shafts, thereby dissecting the body tissue.

Another aspect of the present invention is a balloon catheter comprising an outer tube having a lumen extending therethrough and at least one expandable balloon adapted for dilating an opening or pocket in the tissue between the urethra and the upper vaginal wall. The expandable balloon has a proximal end and a distal end in the lumen of the outer tube. The expandable balloon also has an inflation tube at its proximal end. The inflation tube is in fluid communication with the interior of the balloon. In one embodiment, the expandable balloon has a blunt dissection tip at its distal end which has sufficient rigidity to allow it to create an opening or pocket in the solid body tissue. In one embodiment, the balloon catheter comprises a plurality of expandable balloons in fluid communication with the inflation tube. In another embodiment, the balloon catheter is adapted to fit in the lumen of a large bore needle. In still another embodiment, the expandable balloon has a flat profile. In another embodiment, the balloon further comprises internal non-expansive ribs. In yet another embodiment, the catheter extends into the interior of the balloon. In still another embodiment, the balloon is on the exterior surface of the catheter.

Another aspect of the present invention is a detachable member sling application device for introducing a sling having sutures attached thereto into an opening or pocket in a body tissue. The detachable member sling application device has a housing with an introduction shaft connected thereto. The introduction shaft has a lumen extending therethrough which is adapted to receive the sling having sutures attached thereto. The detachable member sling application device also has a detachable member on the distal end of the introduction shaft. The detachable member is connected to at least one of the sutures attached to the sling. In one embodiment, the detachable member sling application device further comprises an axially movable needle. In this embodiment, the needle comprises a needle shaft and a sharpened point. The needle is located inside the lumen of the introduction shaft and is extendable therefrom.

Another aspect of the present invention is a retrieval device for introducing a sling into an opening or pocket in a body tissue, comprising a shaft having an engaging member at its distal end. The engaging member is adapted to engage a detachable member connected to a suture attached to the sling.

Another aspect of the present invention is a method of stabilizing the bladder neck. A pocket or opening is formed in the tissue between the urethra and the upper vaginal wall. A sling application device is inserted into the pocket or opening. A sling is introduced into the pocket or opening with the sling application device. The sling is secured to tissue or bone to stabilize the bladder neck. In one embodiment the method further comprises providing a detachable member sling application device. The detachable member sling application device has a housing with an introduction shaft connected thereto. The introduction shaft has a lumen extending therethrough which is adapted to receive the sling having sutures attached thereto. The detachable member sling application device also has a detachable member on the distal end of the introduction shaft. The detachable member is connected to at least one of the sutures attached to the sling. In this embodiment, the step of inserting a sling application device into the pocket or opening comprises inserting the detachable member sling application device into the opening or pocket. Another step in this embodiment comprises detaching a detachable member from a distal end of the shaft of the detachable member sling application device. The detachable member is connected to the sling. Another step in this embodiment comprises introducing a shaft of a retrieval device into the opening or pocket. Yet another step in this embodiment comprises engaging the detachable member with an engaging member on the shaft of the retrieval device. Another step of this embodiment comprises withdrawing the shaft of the retrieval device from the opening or pocket, thereby introducing the sling of the detachable member sling application device into the opening or pocket. In another embodiment, the method further comprises extending an axially movable needle from a distal end of the shaft of the detachable member sling application device into the body tissue and toggling the needle to move the detachable member within the opening or pocket. In still another embodiment, the opening or pocket is in a hiatus between a urethra and an upper vaginal wall. In another embodiment, the method further comprises the step of expanding the opening or pocket in the hiatus using a balloon catheter having at least one expandable balloon with a blunt dissection tip at its distal end. In this embodiment, the blunt dissection tip has sufficient rigidity to allow it to make the opening in the body tissue when contacting the tissue.

Another aspect of the present invention is a device for expanding an opening or pocket within a body tissue. The device comprises a tube having a lumen extending therethrough, an axially movable expandable and collapsible expansion basket attached to the tube for insertion into the opening or pocket within the body tissue and expansion thereof, and an expansion and collapse control in communication with the expandable and collapsible basket for expanding and collapsing the basket. In one embodiment, the basket comprises a plurality of wires. In another embodiment, the expansion and collapse control comprises a pull wire.

Another aspect of the present invention is a grasping device adapted for insertion into a lumen of an expansion device having an expansion basket for expanding an opening or pocket within a body tissue. The grasping device comprises a catheter having a grasping member on its distal end for grasping a suture or guide member which has been advanced into the expansion basket of the expansion device. In one embodiment, the grasping member comprises a self-expanding basket. In another embodiment, the self-expanding basket is adapted to fit inside the expansion basket of the expansion device when the expansion basket of the expansion device is in an expanded configuration.

Another aspect of the present invention is a method of creating a pocket in the tissue between the urethra and the upper vaginal wall comprising hydrodissecting the tissue.

Another aspect of the present invention is a method for holding a pocket in a body tissue in an open position. A lumen is made in the body tissue. The lumen in the body tissue is expanded to create the pocket in the body tissue. An expansion device is inserted into the pocket and an expansion basket on the expansion device is expanded in the pocket, thereby holding the pocket in the open position. In one embodiment, the body tissue comprises a hiatus between a urethra and an upper vaginal wall. In another embodiment, the lumen is expanded with a balloon catheter. In another embodiment, the method further comprises inserting a suture or guide member through a suprapubic incision into the pocket, inserting a grasping device comprising a catheter having a grasping member on its distal end into a lumen of the expansion device, grasping the suture or guide member with the grasping device, and withdrawing the suture or guide member to a desired position. In one embodiment, the suture or guide member is grasped under direct vision.

Yet another aspect of the invention is a method of introducing a sling into an opening in a body tissue comprising holding a pocket or opening in a body tissue in an open position with an expansion basket as described above, grasping a suture or guidewire within the expanded opening as described above, and drawing the suture or guidewire to a desired position. The method is performed on each side of the urethra such that two sutures extend from the patient's body. The two sutures are tied together and used to guide a sling into the opening. In one embodiment, the body tissue comprises a hiatus between the urethra and the upper vaginal wall.

Yet another aspect of the invention is a method of introducing a sling into an opening in a body tissue comprising holding a pocket or opening in a body tissue in an open position with an expansion basket as described above, grasping a suture or guidewire within the expanded opening as described above, and drawing the suture or guidewire to a desired position. The method is performed on each side of the urethra such that two sutures extend from the patient's body. A sling is attached to the two sutures outside of the patient's body and introduced into the opening in the body tissue. In one embodiment, the body tissue comprises a hiatus between the urethra and the upper vaginal wall.

BRIEF DESCRIPTION OF THE DRAWINGS

FIG. 8 shows the blunt dissection tip extending into a tissue from the distal end of the shaft of a guide member placement device having a male connector to create an opening in the tissue.

FIG. 16 is an enlarged view of the distal end of the sling application catheter taken along line 16—16 of FIG. 15.

FIG. 17 is a cross-sectional view taken along line 17—17 of the sling application catheter of FIG. 16.

FIG. 18 is an enlarged view of the distal end of a sling application catheter having a reinforcing stiffener within the pouch.

FIG. 19 is a cross-sectional view taken along line 19—19 of the sling application catheter of FIG. 18.

FIG. 20 is an enlarged view of the distal end of a sling application catheter having a pouch made of a porous material.

FIG. 24 is a plan view of a tissue dissector/dilator in which the spring return button is at the most proximal point and the blunt dissection tip and the expandable balloon are retracted within the shaft.

FIG. 25 is a plan view of the tissue dissector/dilator in which the spring return button has been advanced to the locked position and the expandable balloon and blunt dissection tip are fully extended from the shaft.

FIG. 27 is a plan view of a tissue dissector/dilator in which the spring return button has been advanced towards the distal end of the slide and the blunt dissection tip extends from the shaft.

FIG. 28 is a plan view a tissue dissector/dilator in which the trigger has been squeezed, causing the balloon to inflate.

FIG. 47A is a plan view of the first shaft taken along line 47A—47A of the sling application device of FIG. 47.

FIG. 47B is a plan view of the second shaft taken along line 47B—47B of the sling application device of FIG. 47.

FIG. 70 shows the sharpened point of the needle of the detachable member sling application device extending through the upper vaginal wall.

DETAILED DESCRIPTION OF THE PREFERRED EMBODIMENTS

Figure 1:
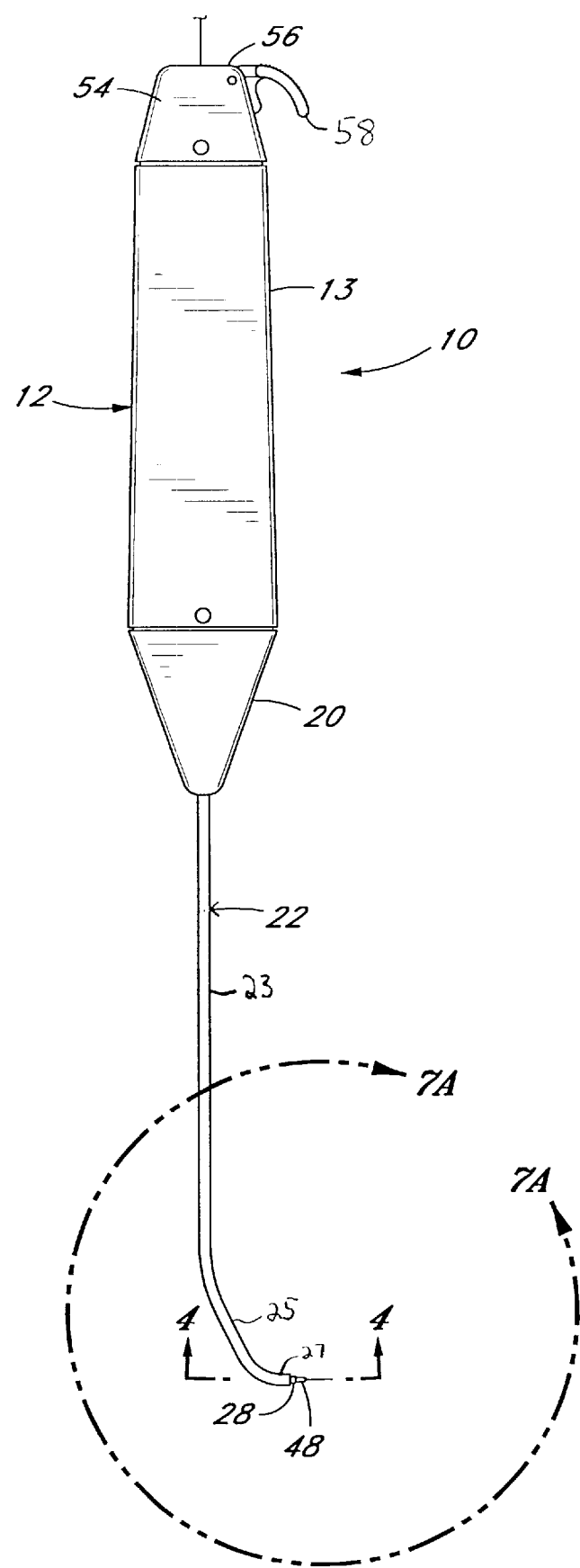
FIG. 1 is a side view of an embodiment of a guide member placement device having a male connector at the distal end of the shaft.

The present invention relates to methods and devices for creating openings or pockets in body tissues and/or dilating body tissues. The guide member placement devices, sling application catheters, tissue dissector/dilators, sling application devices, sling application systems, detachable member sling application devices, retrieval devices, and balloon catheters of the present invention may be used percutaneously or in conjunction with laparoscopic techniques. In such laparoscopic procedures, trocars are placed in the abdomen and the abdomen is insufflated with $CO_2$, causing it to distend. The devices are introduced into the patient's body via the trocars, and the procedure is visualized with a laparoscope.

The devices of the present invention may be used in a wide variety of medical procedures, but are particularly well suited for urethral floor reconstruction procedures such as bladder neck stabilization or suspension procedures in which a sling is used to maintain or improve urinary continence by stabilizing and/or slightly compressing the urethra or by creating a non-moveable pelvic floor. Slings suitable for use in bladder neck stabilization procedures and methods for implanting them are disclosed in the copending U.S. patent application entitled "Stabilization Sling for Use in Minimally Invasive Pelvic Surgery" (VESITEC.023A), filed simultaneously herewith, and the identically titled U.S. Provisional Patent Application Serial No. 60/038,379, filed Feb. 13, 1997, the disclosures of which are incorporated herein by reference.

The present invention is particularly well suited for bladder neck stabilization procedures for treating urinary incontinence in females. The bladder neck stabilization procedures for which the present invention is especially well suited involve the creation of an opening or pocket in the tissue between the urethra and the upper vaginal wall, which is called the hiatus. The sling is then inserted in the opening or pocket. Sutures or integral attachment members at the ends of the sling are attached to the pubic bone or surrounding tissue and the tension is adjusted to slightly compress or stabilize the urethra by providing a platform to reduce distension resulting from internal pressures, thereby maintaining or improving urinary continence. Suitable methods and devices for adjusting the tension on the sutures are disclosed in U.S. Pat. No. 5,611,515, issued Mar. 18, 1997 to Benderev et al., the disclosure of which is incorporated herein by reference.

The opening or pocket may be created in a variety of ways. In one approach, the opening or pocket is created by introducing an expandable balloon into the tissue between the urethra and the upper vaginal wall. When the balloon is expanded, the surrounding tissue is dilated or torn, generating an opening or pocket of sufficient size to receive the sling.

In an alternative approach, the opening or pocket is created by hydrodissection. In this approach, a bolus of saline or other sterile solution is injected into the tissue between the urethra and the upper vaginal wall, resulting in an opening or pocket sized to receive the sling. The bolus of saline may be administered by positioning a syringe inside the vagina and piercing the vaginal wall with the needle of the syringe such that the tip of the needle is in the tissue between the urethra and the upper vaginal wall. Alternatively, the bolus of saline may be administered directly into the hiatal tissue without piercing the vaginal wall.

The volume of saline injected into the tissue in the hydrodissection procedure is too large to be rapidly absorbed such that the tissue must separate to accommodate the saline bolus. Preferably, the volume of saline introduced into the tissue is from about 4 cc to about 10 cc. More preferably, the volume of saline is about 4 to about 5 cc.

In yet another approach, the opening or pocket is created by dissecting the tissue between the urethra and the upper vaginal wall with a combination of blunt dissectors and sharp cutters.

The opening or pocket may be created and the sling may be introduced by taking a variety of routes through the patient's body. In one approach, called the percutaneous approach, the opening or pocket is created by making suprapubic incisions into which a device for introducing an opening or pocket in a body tissue or dilating a body tissue is inserted. The device is advanced through the patient's body tissue into the tissue between the urethra and the upper vaginal wall where the opening or pocket is to be created. In some instances, the device for introducing an opening or pocket in a body tissue or dilating a body tissue may also introduce the sling into the opening.

In another approach, called the hiatal approach, the opening or pocket is created and the sling is introduced by directly accessing the tissue between the urethra and the upper vaginal wall. In this procedure the opening or pocket can be created without making suprapubic or vaginal incisions.

In other approaches, the opening or pocket is created directly in the tissue between the urethra and the upper vaginal wall and the sling is introduced with a device advanced into the opening or pocket from a suprapubic or vaginal incision.

The devices and procedures described briefly above are discussed in greater detail in the following sections. It will be appreciated by those of skill in the art that any of the disclosed devices and methods for creating an opening or pocket can be combined with any of the disclosed devices and methods for introducing a sling into the opening or pocket.

Guide Member Placement Device

One aspect of the present invention relates to methods in which the sling is introduced over a guide member and devices for use in such methods. The guide member may be a suture, guidewire, or other structure suitable for guiding a sling to a desired location.

In one embodiment, the opening or pocket in which the sling is introduced is created first and the guide member is then passed through the opening or pocket. In this embodiment, the opening or pocket may be created using any of the techniques disclosed herein, including expandable balloons and hydrodissection.

Alternatively, the opening or pocket may be created during guide member placement by extending and retracting a blunt dissector on a guide member placement device.

In yet another embodiment, the opening or pocket in which the sling is introduced is created by the sling application catheter disclosed herein after the guide member is positioned.

Devices and methods for using a guide member to introduce a sling in the tissue between the urethra and the upper vaginal wall will now be discussed in greater detail.

One aspect of the present invention relates to guide member placement devices for applying a guide member under the urethra in a less invasive manner without puncturing the vaginal wall.

In general, the guide member placement device comprises a shaft having a proximal end, a distal end, and a lumen extending therethrough. The lumen is adapted for receiving a guide member.

Preferably, the shaft is rigid. It is also preferred that the proximal end of the shaft is attached to a handle having a lumen extending therethrough. Preferably, the guide member placement device has a blunt dissection tip with a lumen extending therethrough. The blunt dissection tip is preferably located at the distal end of the shaft. It is also preferred that the blunt dissection tip is on a blunt dissector which is within the shaft and is extendable from and retractable in the shaft.

Preferably, the lumen in the blunt dissector is in fluid communication with the lumen in the handle. Preferably, the blunt dissector is axially movable and can be extended from and retracted in the shaft. Preferably, the blunt dissector is made of rigid plastic or flexible metal. For example, the blunt dissector may be a coil of stainless steel. The blunt dissector may be solid and may be made of metals such as stainless steel, spring steel, Elgiloy, Nitinol, or other generally elastic metals. The blunt dissector may also be a rigid plastic such as nylon or Acrylonitrile Butadiene Styrene (ABS).

The guide member placement device has an engaging member at the distal end of the shaft which is complementary to or otherwise adapted to be attached to an engaging member at the distal end of the shaft of a second guide member placement device, such that the shafts of the two guide member placement devices can be attached to one another with the lumens of the blunt dissectors in each shaft in fluid communication with one another.

Figure 2:
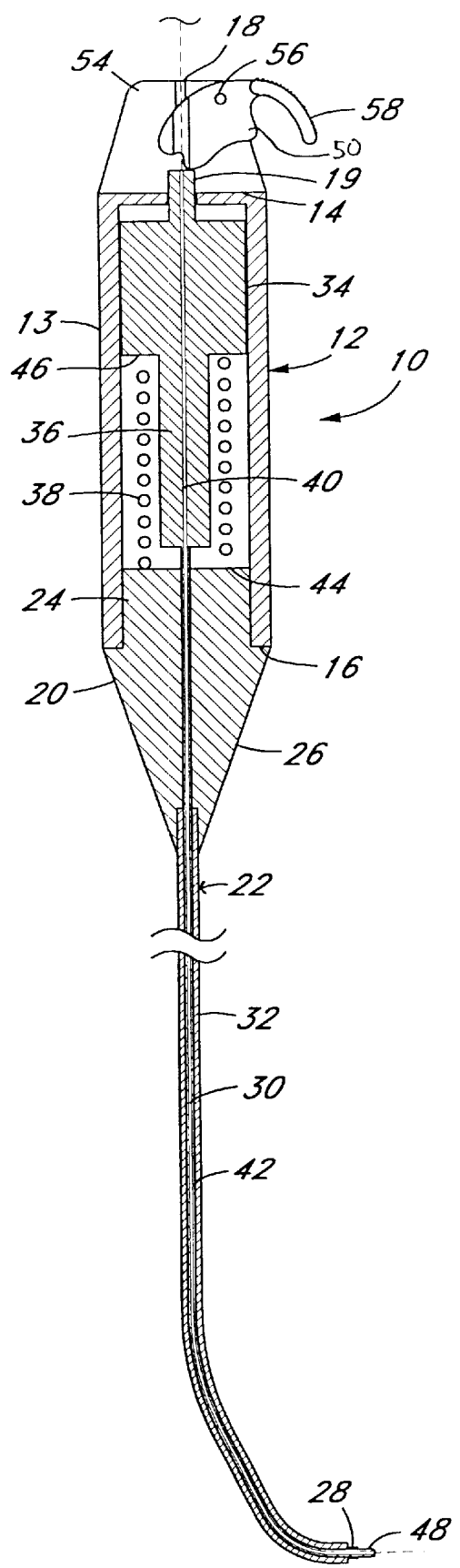
FIG. 2 is an assembled cross-sectional view of the guide member placement device of FIG. 1 showing the internal structure of the device.
Figure 3:
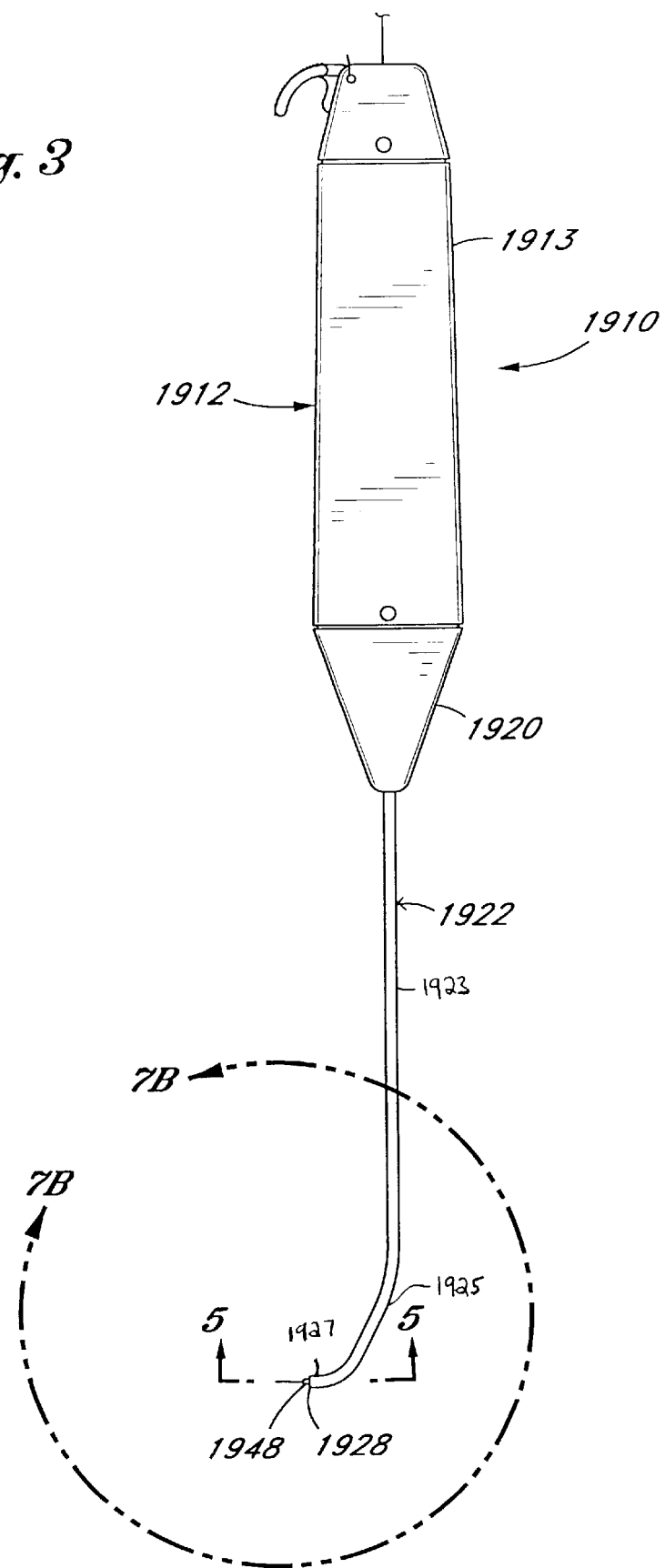
FIG. 3 is a side view of an embodiment of a guide member placement device having a female connector at the distal end of the shaft.

Referring to FIGS. 1, 2 and 3, there are disclosed guide member placement devices 10, 1910 in accordance with one aspect of the present invention. Handle 12, 1912 serves both as a gripping area for the physician and as a support structure for the guide member placement device. Handle 12, 1912 preferably comprises a hollow tubular body 13, 1913. The handle 12, 1912 is preferably of such a size to be easily gripped by a user. For instance, in one embodiment, the handle is approximately 0.75 inches (20 mm) in diameter and approximately 4 inches (110 mm) in length. Preferably, handle 12, 1912 is provided with knurling or other surface texturing to produce a high friction gripping surface.

A support 20, 1920 is preferably mounted such that it extends from the distal end of the handle 12, 1912 to provide a mounting support for the shaft 22, 1922. The support 20, 1920 acts as a transition member from the handle 12, 1912 to support the shaft 22, 1922.

The shaft 22, 1922 is an elongate member with its proximal end inserted within or secured to the support 20, 1920. The shaft 22, 1922 may be attached to the support 20, 1920 in any variety of manners, including brazing, threading or other means well known to those of skill in the art.

The shaft 22, 1922 extends distally from the support 20, 1920 and is preferably within the range of from about 6 inches to about 10 inches in length.

Figure 7A:
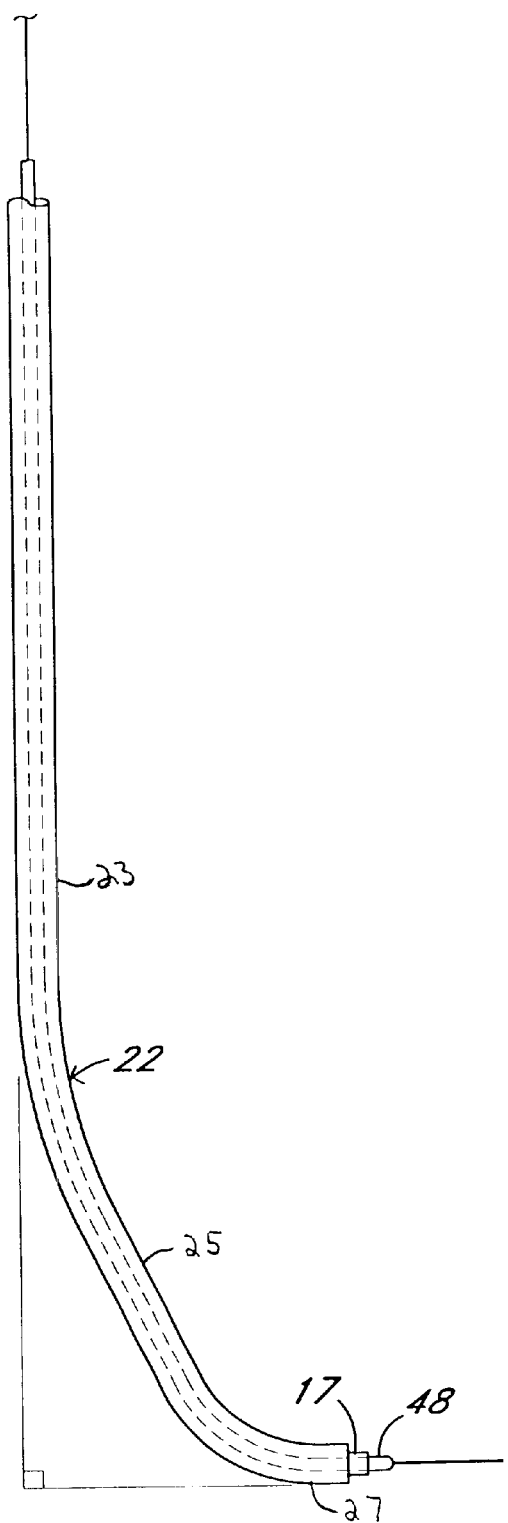
FIG. 7A is an enlarged view of the distal portion of the shaft of the guide member placement device taken along line 7A—7A of FIG. 1.
Figure 7B:
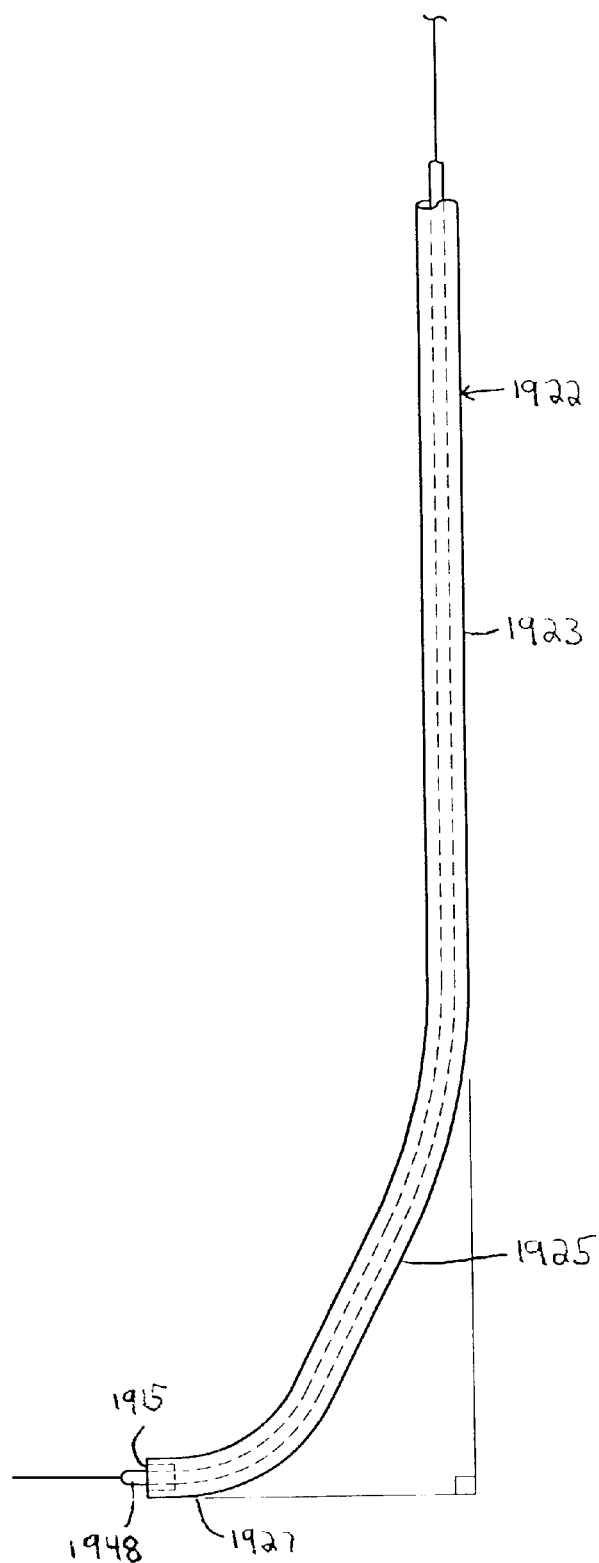
FIG. 7B is an enlarged view of the distal portion of the shaft of the guide member placement device taken along line 7B—7B of FIG. 3.
Figure 7C:
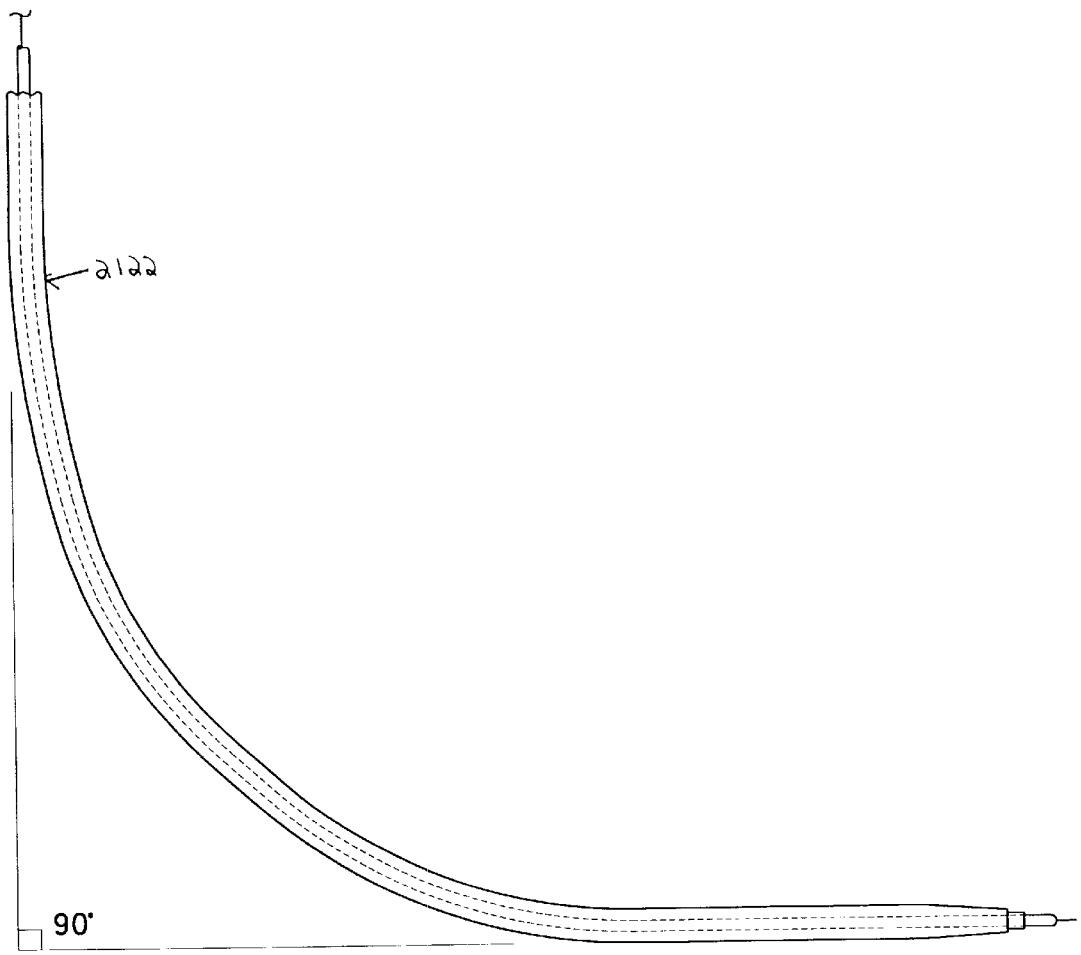
FIG. 7C is an enlarged view of the distal portion of the shaft of a guide member placement device having an alternate shaft configuration in which the curve is smoothly curved.
Figure 7D:
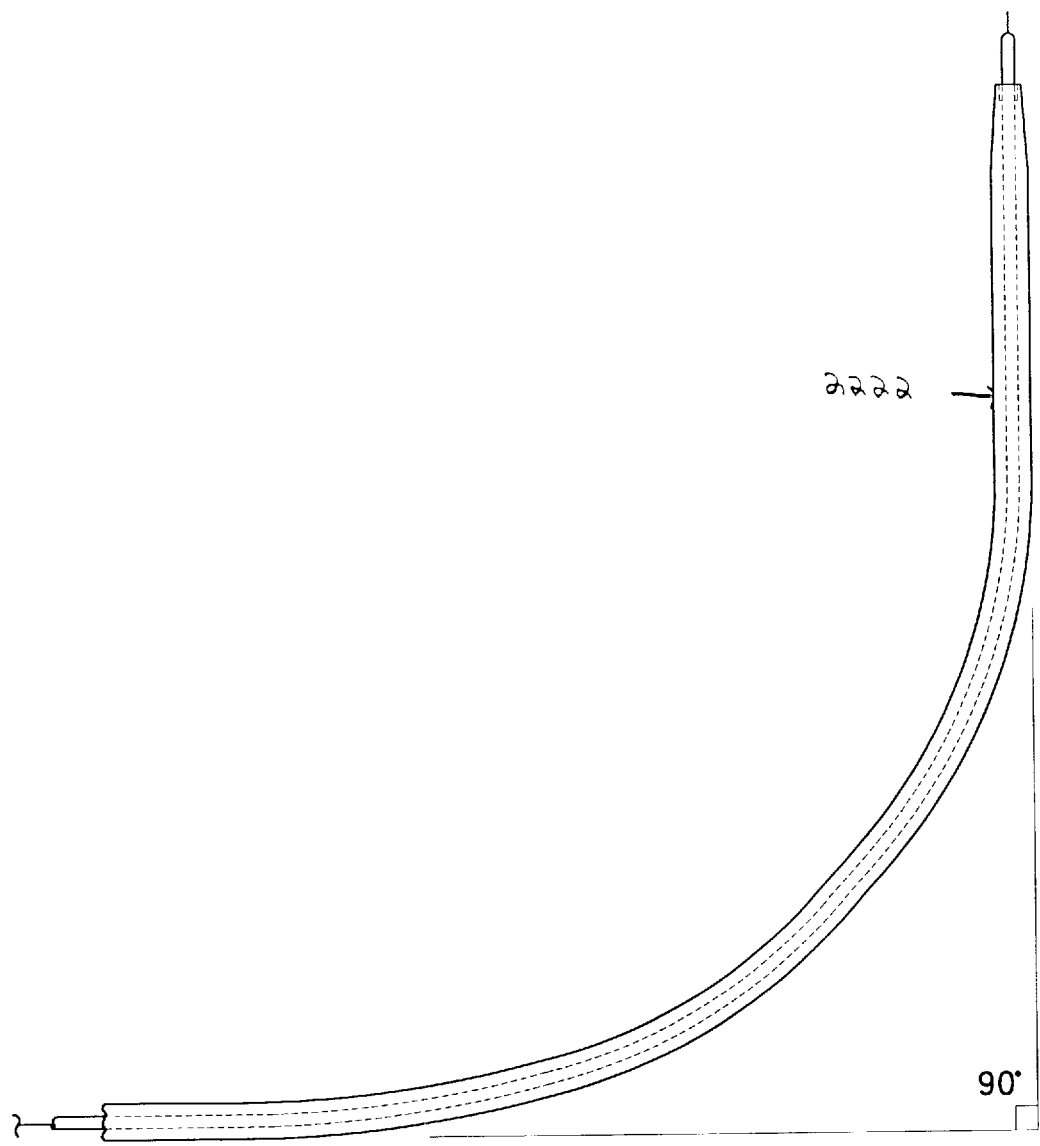
FIG. 7D is an enlarged view of the distal end of the shaft of a guide member placement device having an alternate shaft configuration in which the curve is smoothly curved.

The shaft 22, 1922 has a lumen 30 extending therethrough. A preferred embodiment of the distal end of the shaft is shown in FIGS. 7A and 7B. In this embodiment, the shaft 22, 1922 has a straight proximal section 23, 1923, a bent intermediate section 25, 1925, and a distal end 27, 1927. In an alternate embodiment, the shaft 2122, 2222 may be smoothly curved as shown in FIGS. 7C and 7D. In the embodiments of FIGS. 7A–7D, the distal end of the shaft is preferably oriented at an angle of 90° relative to the straight proximal section of the shaft. Preferably, the curve of the shaft is smooth to facilitate movement of the blunt dissector 32 within the shaft.

As will be understood by one of skill in the art, the dimensions and curvature of the shaft 22, 1922 may vary depending on anatomical considerations and the type of procedure in which it is intended to be used.

Figure 4:
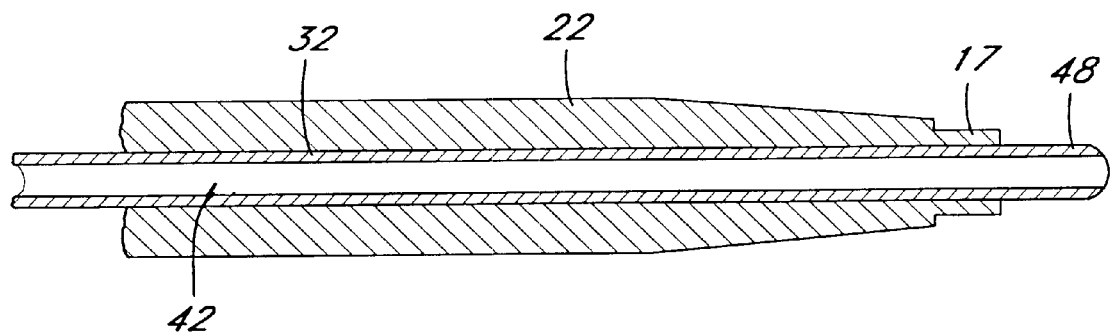
FIG. 4 is an enlarged cross-sectional view taken along line 4—4 of the distal end of the shaft of a guide member placement device of FIG. 1.
Figure 5:
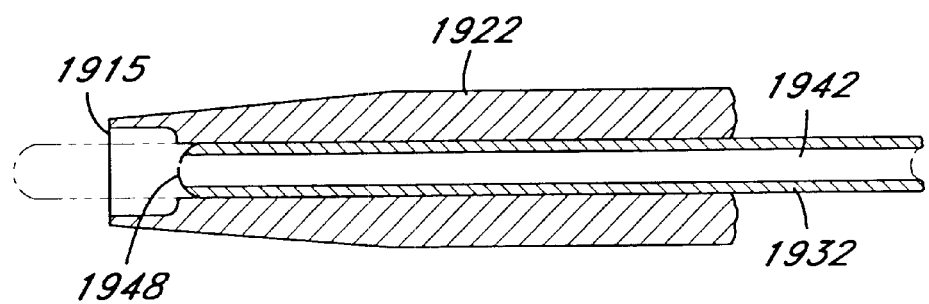
FIG. 5 is an enlarged cross-sectional view taken along line 5—5 of the distal end of the shaft of the guide member placement device of FIG. 3.

The distal ends 27, 1927 of the shafts 22, 1922 of the guide member placement devices 10, 1910 are provided with engaging members 28, 1928 which are complementary to each other, such that the shafts 22, 1922 of the two guide member placement devices 10, 1910 are adapted to be attached to one another. In one embodiment of the guide member placement device 10, depicted in FIGS. 1 and 2, the engaging member comprises a male connector 17 as illustrated in the enlarged cross-sectional view of FIG. 4. The male connector 17 on the guide member placement device 10 shown in FIGS. 1 and 2 is complementary to the female connector 1915 on the guide member placement device 1910 shown in FIG. 3 and shown in the enlarged cross-sectional view in FIG. 5. As shown in the enlarged cross-sectional view of FIG. 6, the male connector 17 on the guide member placement device 10 of FIGS. 1, 2 and 4 engages the female connector 1915 on the guide member placement device 1910 of FIGS. 3 and 5 and attaches the two guide member placement devices 10, 1910 together such that the lumens 42, 1942 of the blunt dissectors 32, 1932 of each of the two devices are in fluid communication with one another. When desired, the male connector 17 disengages from the female connector 1915, permitting the two guide member placement devices 10, 1910 to be separated.

While the complementary engaging members 28, 1928 of the embodiments shown in FIGS. 1–5 are male and female connectors, those skilled in the art will appreciate that a number of alternative configurations can be employed for the engaging members, and the present invention contemplates such alternative configurations.

FIG. 2 is a cross-sectional view showing the internal structure of the guide member placement device 10 having a male connecter at the distal end of the shaft. The internal structure of the embodiment of the guide member placement device 1910 having a female connector at the end of the shaft is similar to that shown in FIG. 2. Thus, the internal structure will only be described with respect to the device having a male connector.

As shown in FIG. 2, the handle 12 has a proximal end wall 14 and a distal end wall 16. The support 20 as illustrated is provided with a generally cylindrical proximal section 24 for engagement within the distal end of the handle 12 and a tapered distal section 26 for securing the shaft.

The shaft 22 is preferably no more than about 0.1 inches (2.5 mm) in diameter and is provided with at least one central lumen 30 for acceptance of an axially movable blunt dissector 32. The blunt dissector 32 is mounted within the handle 12 and extends through the support 20 and the shaft 22. The blunt dissector 32 is preferably provided at its proximal end with a relatively large diameter body portion 34 adapted for reciprocal motion within tubular handle 12. Body portion 34 is preferably provided with a slightly smaller diameter recessed portion 36 for receiving a return spring 38 which biases the blunt dissector 32 in the proximal direction and has a lumen 40 extending therethrough which is in fluid communication with the lumen 42 of the narrow portion of the blunt dissector. Alternatively, any of a variety of well known means can be utilized to provide a proximal bias on the blunt dissector 32.

The length of body portion 34 is less than the axial length of the cavity within handle portion so that the body portion 34 has an axial range of motion within the range of from about 2 mm to about 10 mm, and preferably about 0.12 inch (3 mm). The proximal end wall 44 of the support 20 which extends into the handle 12 acts as one limiting stop for distal travel of body portion 34. The distal surface of the end wall 14 of the handle limits proximal travel of body portion 34. Spring 38 pushes against an annular shoulder 46 on body portion 34, biasing the blunt dissector 32 proximally.

The distal end of blunt dissector 32 is provided with a blunt dissection tip 48 having a lumen therethrough. Spring 38 normally biases the blunt dissector 32 towards a first retracted position within the distal end of shaft 22 such that the blunt dissection tip 48 does not extend from the shaft 22. Axial distal force on body portion 34 extends the blunt dissection tip 48 into a second position in which it extends from the shaft 22. Although the blunt dissection tip 48 may be extended and retracted in any number of ways, such as by use of a knob or button, it is preferred that a rotatable cam 50 be used.

The cam 50 is attached to a post 54 extending proximally from the handle 12 and having a lumen 18 therein which is in fluid communication with the lumen 40 in the recessed position of the blunt dissector and the lumen 42 in the narrow portion of the blunt dissector. The cam 50 is rotatably mounted about a pin 56 which extends along an axis perpendicular to the longitudinal axis of the shaft 22. The proximal end of the body portion has a rod 19 which extends proximally through an opening in the proximal end wall 14 of the handle.

The cam 50 has at least a two position engaging surface which, when rotated into position, engages the rod 19 of the body portion. In a first position, the cam 50 is biased by the return spring 38 to a position in which the blunt dissection tip 48 is fully retracted within the shaft 22. In a second position, the bias imposed by return spring 38 is overcome and engaging surface of the cam 50 engages the rod 19 such that the blunt dissection tip 48 is extended outwardly from the shaft 22. The cam 50 is preferably provided with an actuator portion 58 which extends radially outwardly and which may be used by the operator for rotating the cam.

Alternatively, other means such as pneumatic force generating means, hydraulic force generating means, piezoelectric force generating means, and electric force generating means may be used to overcome the bias of the spring and extend the blunt dissection tip 48.

It is preferred that this instrument be manufactured from a sterilizable material having sufficient rigidity for its intended purpose. Many acceptable materials are well known in the art, such as stainless steel for the shaft 22, and stainless steel or a plastic for the handle portion 12.

Alternatively, the guide member placement device may be made in a disposable form. In this embodiment, the components preferably are made of a suitable thermoplastic. In particular, the thermoplastic Cycolac 2679F made by General Electric Plastics has been found suitable, which is Acrylonitrile Butadiene Styrene (ABS). Preferably, the shaft 22, blunt dissector 32, and return spring 38 are made of stainless steel.

The use of the guide member placement devices of FIGS. 1–7D in a representative bladder neck stabilization procedure employing a sling is described below and depicted in FIGS. 8–14. However, those skilled in the art will appreciate that the guide member placement device may also be used in a number of other surgical procedures requiring introduction of a guide member.

Figure 11:
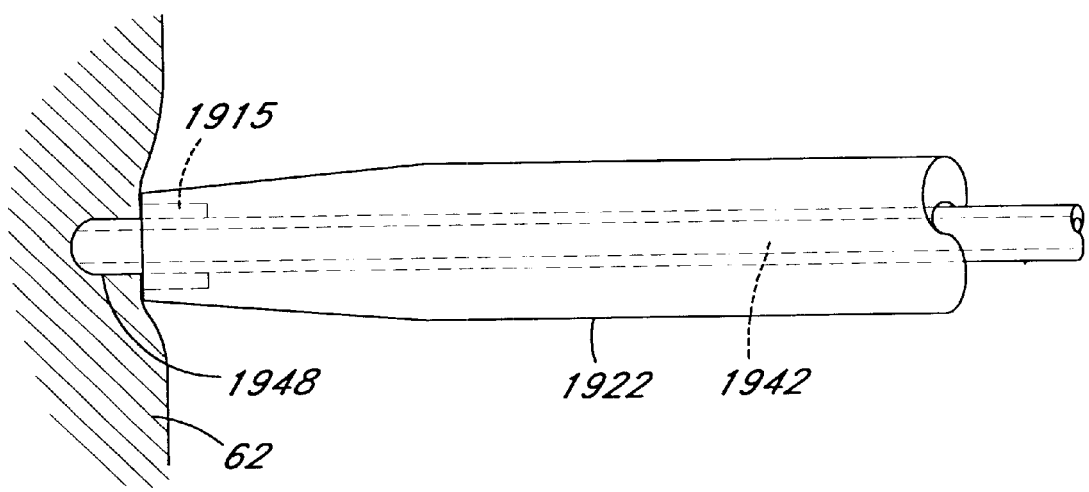
FIG. 11 shows the blunt dissection tip extending into a tissue from the distal end of the shaft of a guide member placement device having a female connector to create an opening in the tissue.

The following procedure is intended to place a guide member in the tissue between the urethra and the vaginal wall without puncturing the vaginal wall. A Foley catheter is placed in the bladder to identify the bladder neck. The guide member placement device is percutaneously inserted into the body. For example, a pair of approximately one inch suprapubic incisions 60 and 61, shown schematically in FIG. 9, may be made over the pubic tubercles and dissection may be carried down to the area of the rectus fascia. A first guide member placement device 10 is placed within one of the incisions and advanced along the back side of the pubic bone so that the distal tip of the shaft 22 is in contact with the bone/fascial surface to decrease the risk of puncturing the bladder. As resistance is felt, the cam 50 is pressed to extend the blunt dissection tip 48 from the distal end of the shaft 22, thereby creating an opening in the body tissue 62 as shown in FIGS. 8 and 11. The cam 50 is then released, retracting the blunt dissection tip 48 into the shaft 22, and the device 10 is advanced through the opening in the body tissue. This process results in the creation of a first opening in the body tissue.

Figure 9:
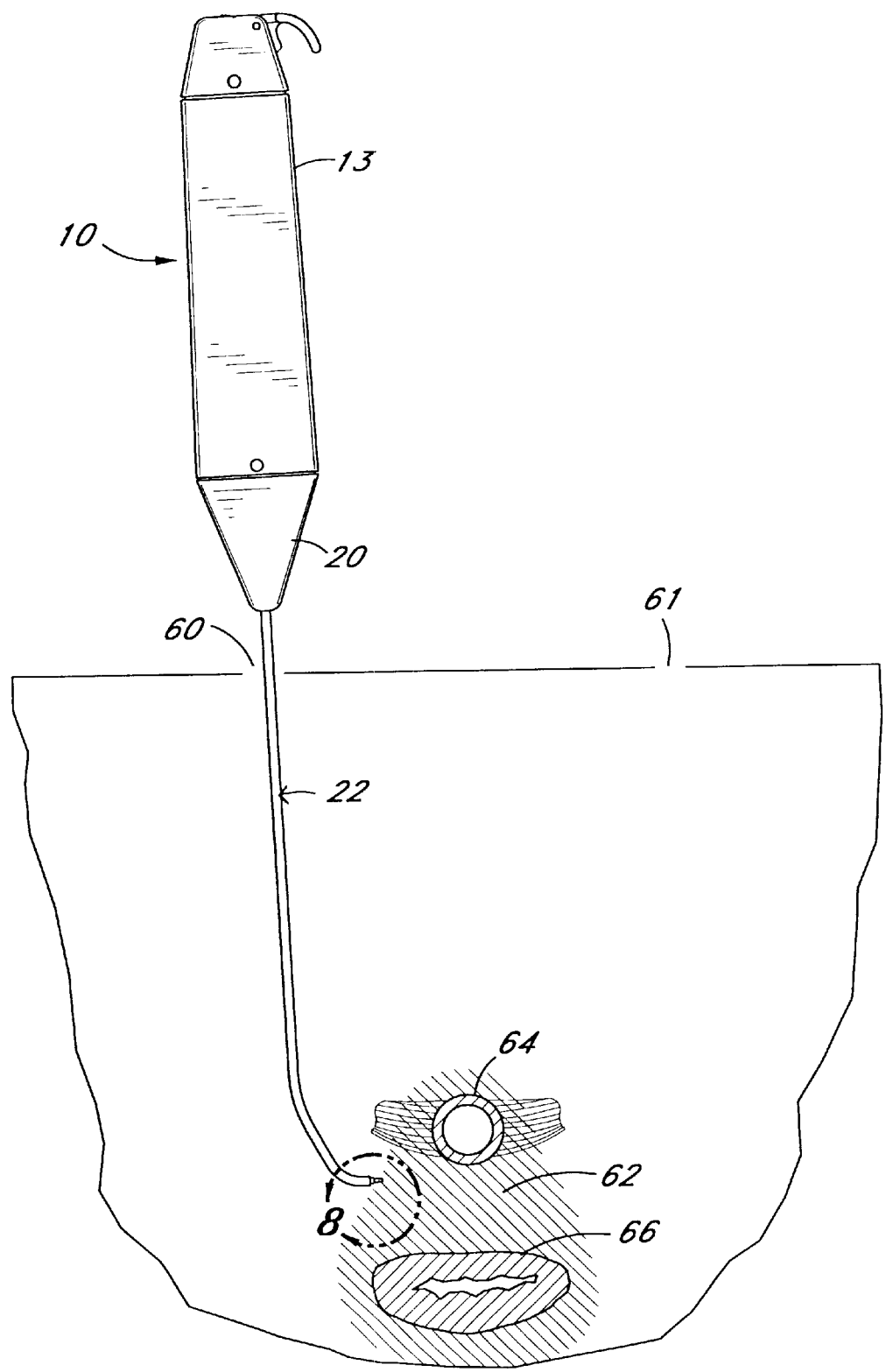
FIG. 9 shows a first guide member placement device that has been inserted into a first suprapubic incision and advanced into the body tissue.
Figure 10:
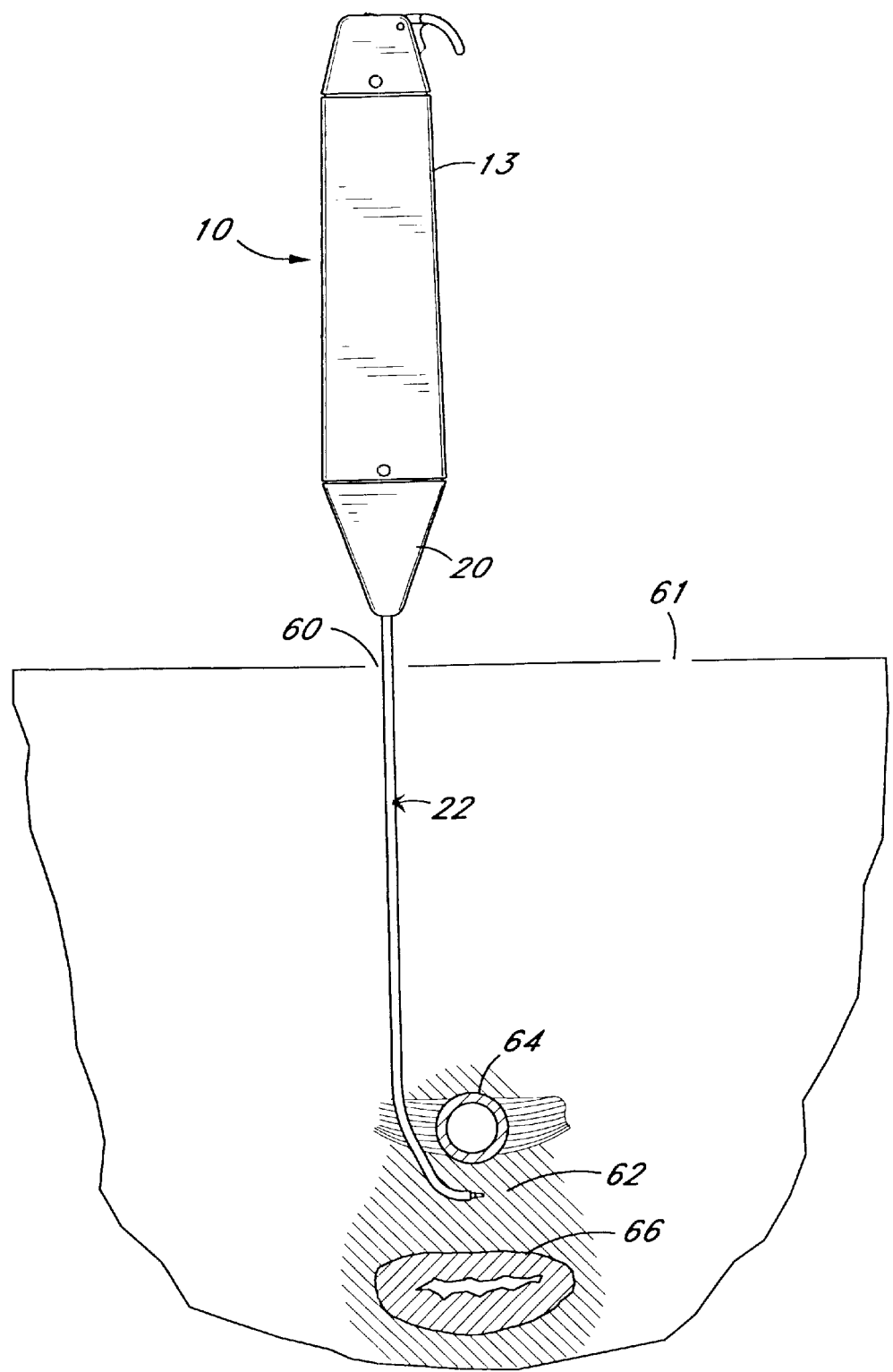
FIG. 10 shows a guide member placement device that has been advanced into the tissue between the urethra and the upper vaginal wall such that the distal end of the shaft extends transversely between the urethra and the upper vaginal wall in the plane defined by the longitudinal axes of the urethra and the vagina.

The first guide member placement device 10 is advanced until it is positioned under the urethra 64 within the tissue 62 lying between the urethra 64 and the upper vaginal wall 66 as shown in FIG. 9. The blunt dissection tip 48 is extended and retracted during advancement of the guide member placement device 10 so as to create an opening in the tissue. Advancement of the guide member placement 10 device with extension and retraction of the blunt dissection tip 48 is continued until the distal end of the shaft 22 is positioned approximately midline to the urethra 64 as shown in FIG. 10 such that the distal end of the shaft 22 extends transversely between the urethra 64 and the upper vaginal wall 66 in the plane defined by the longitudinal axes of the urethra and the vagina.

Alternatively, a pocket or opening in the tissue between the urethra and the vagina may be created beneath the bladder neck prior to insertion of the first guide member placement device using the devices and methods described below. In this embodiment, the first guide member placement device 10 is advanced such that the distal end of the shaft is in the pocket or opening and the device is positioned as described above.

As the guide member placement device 10 is advanced, the elastic upper vaginal wall tents. This tenting can be utilized to determine the position of the guide member placement device 10. The guide member placement device is advanced until tenting is apparent at the desired location.

Figure 6:
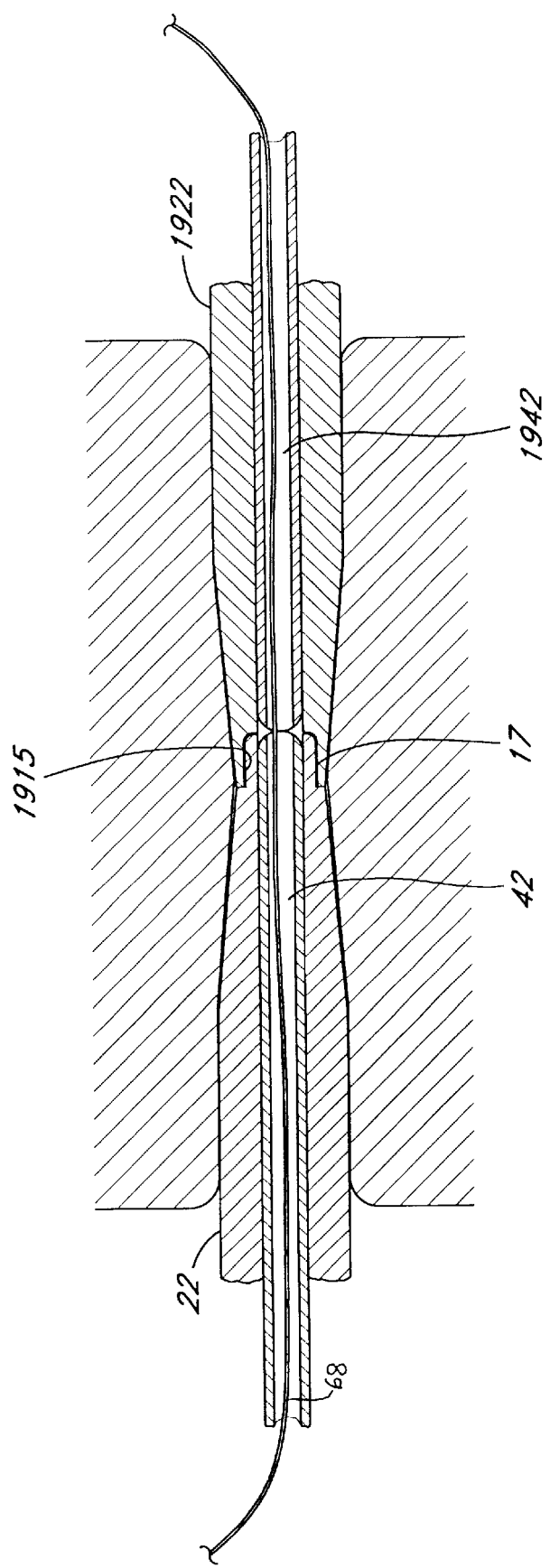
FIG. 6 is a cross-sectional view showing the distal ends of the shafts of the guide member placement devices of FIGS. 1 and 3 coupled through their male and female connectors.
Figure 12:
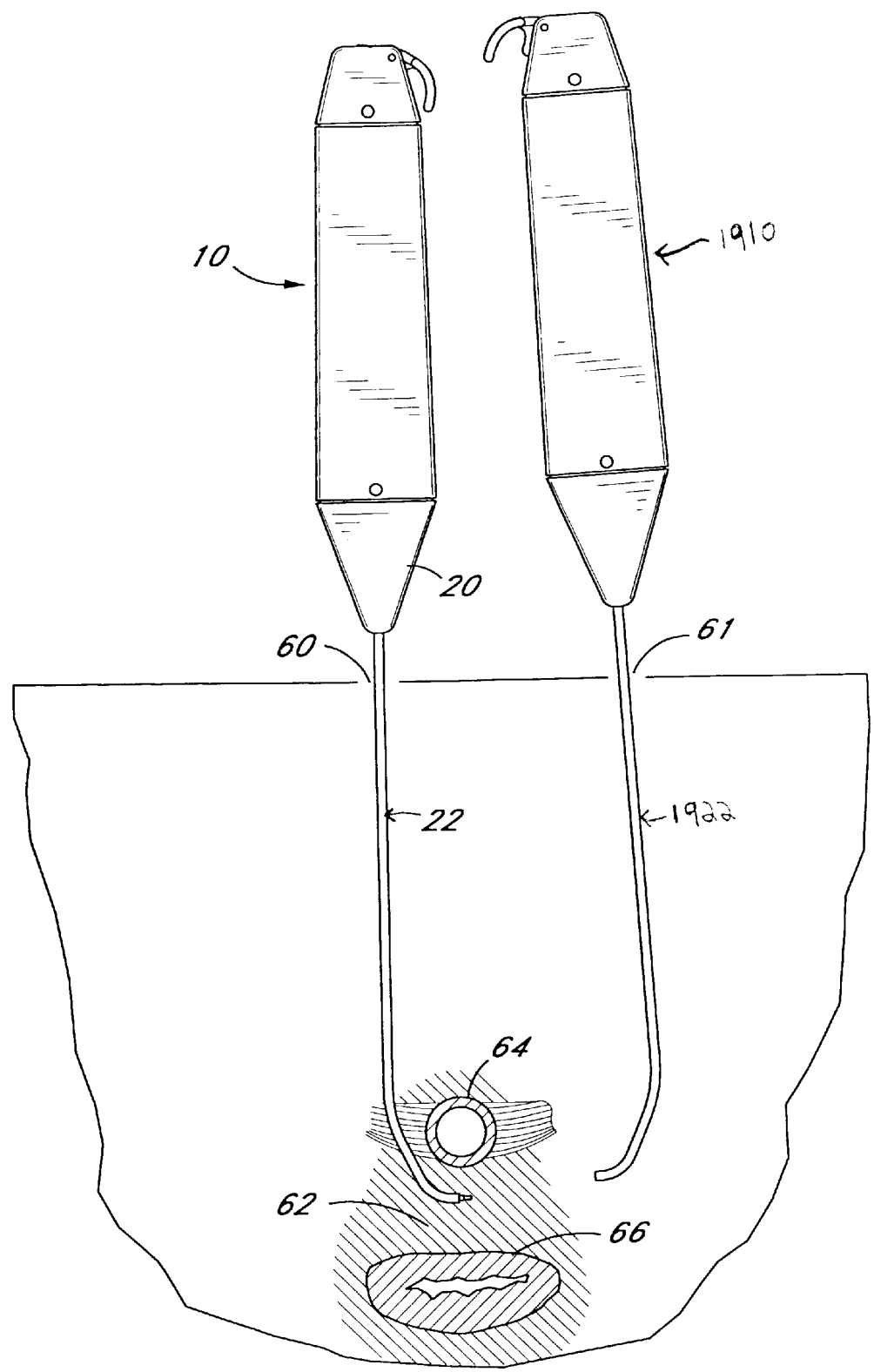
FIG. 12 shows a second guide member placement device that has been inserted into a second suprapubic incision and advanced into a body tissue.

The above process is repeated with a second guide member placement device 1910 as shown in FIG. 12. The second guide member placement device 1910 has an engaging member 1928 complementary to that of the first guide member placement device 10 as shown in FIG. 6. The blunt dissection tip 1948 of the second guide member placement device 1910 is extended and retracted to create a second opening in the body tissue as described above and shown in FIG. 11.

The second guide member placement device 1910 is advanced to a position approximately midline to the urethra 64 such that the distal end of the shaft 1922 extends transversely between the urethra 64 and the upper vaginal wall 66 in the plane defined by the longitudinal axes of the urethra and the vagina.

Alternatively, in the embodiment in which the pocket or opening in the tissue between the urethra and the vagina is created prior to insertion of the first guide member placement device, the second guide member placement device is advanced into the pocket or opening.

The second guide member placement device 1910 is then aligned with the first guide member placement device 10.

Figure 13:
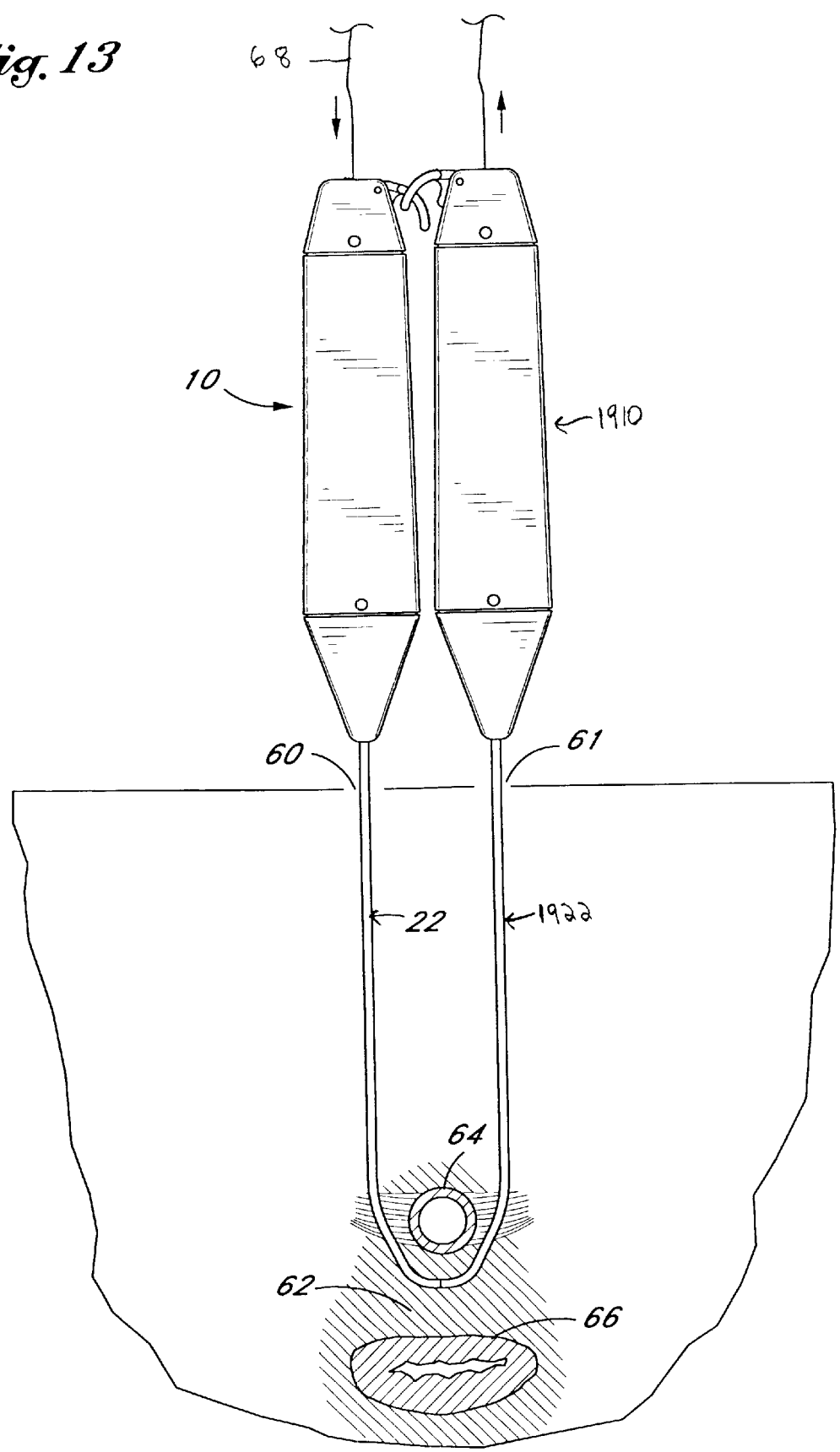
FIG. 13 shows the first and second guide member placement devices in the tissue between the urethra and the upper vaginal wall with the distal ends of their shafts connected to one another.

The first and second guide member placement devices 10 and 1910 are then joined through their engaging members 28, 1928, creating a continuous opening in the tissue 62 between the urethra 64 and the upper vaginal wall 66, as shown in FIG. 13. In an alternative embodiment, in addition to joining the two shafts, the two handles may also be coupled together and secured to one another.

After joining of the two guide member placement devices 10, 1910, the lumens 42, 1942 of the blunt dissectors are in fluid communication with one another, as shown in FIG. 6. As shown in FIGS. 13 and 2, a guide member 68 is then inserted into the lumen 18 in the handle 12 of the first guide member placement device 10 and advanced through the lumens 40, 1940, 42, 1942 of the blunt dissectors of the first and second guide member placement devices 10, 1910 until it exits from the handle 1912 of the second guide member placement device.

Figure 14:
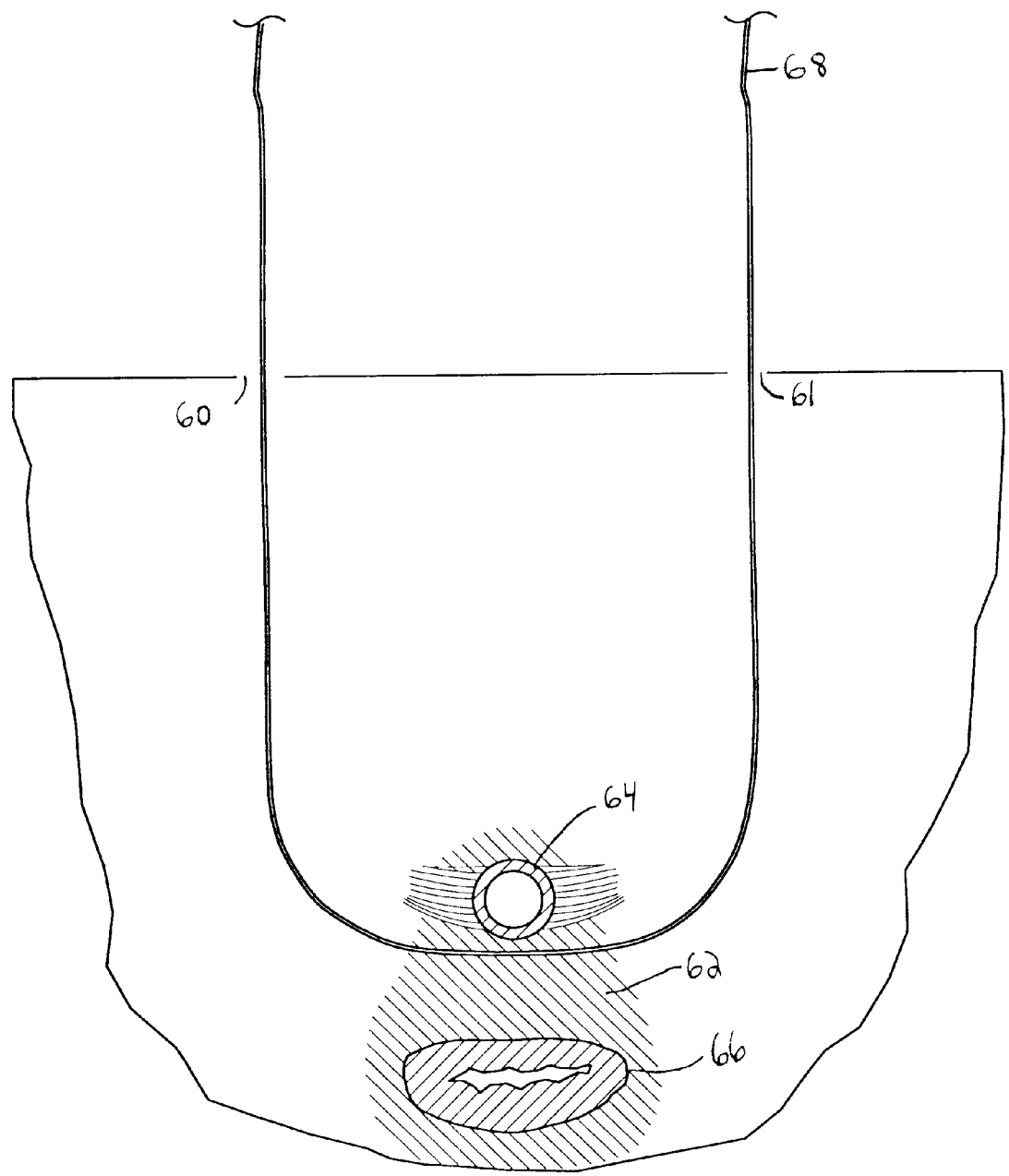
FIG. 14 shows a guide member extending between the two suprapubic incisions after removal of the first and second guide member placement devices.

The engaging members 28, 1928 of the two guide member placement devices 10, 1910 are then disengaged from one another and the devices 10, 1910 are removed from the patient's body, leaving the guide member 68 in place, as shown in FIG. 14.

The guide member 68 may then be used to introduce a sling attached to a sling application catheter in order to stabilize the bladder neck or stabilize the urethral floor as described in the following sections.

In alternative embodiments of the method, rather than using the blunt dissection tips 48 of the guide member placement devices to create the continuous opening in the tissue, the guide member placement device may be inserted to a pre-formed opening in the tissue between the urethra and the upper vaginal wall. The pre-formed opening may be created by hydrodissection or with balloon catheters as described below. The steps of this embodiment of the method are similar or identical to the method described above. However, if desired, this embodiment of the method can be practiced with guide member placement devices having a blunt dissector which is fixed in a position in which it is extended from the shaft.

In an alternative embodiment of the method, the guide member placement device may be advanced through a trocar into the tissue between the urethra and the upper vaginal wall. In another embodiment, the guide member placement device may be viewed laparoscopically during the procedure to ensure proper positioning and assist in the alignment of the first and second guide member placement devices.

Sling Application Catheter

Another aspect of the present invention is a sling application catheter for introducing a sling into an opening or pocket in the patient's body tissue. In particular, the sling application catheter of the present invention can be used in urethral floor reconstruction procedures, such as bladder neck stabilization procedures, to introduce a sling into the tissue between the urethra and the upper vaginal wall in a less invasive manner than the techniques currently in use.

Generally, the sling application catheter comprises a catheter having a sling therein which is releasably engaged with the catheter. Preferably, the sling is releasably engaged by a pouch in the catheter. Preferably, the sling application catheter is adapted to be guided along a guide member. The guide member may be a suture, guidewire, or other structure suitable for guiding the sling application catheter to a desired location.

The sling application catheter may be attached to the guide member, suture, or other guiding device in numerous ways. For example, the catheter may have a lumen extending therethrough through which the guide member passes. The guide member may pass along the full length of the lumen, thereby extending entirely through the catheter. Alternatively, the guide member may extend partially through the lumen but exit the catheter along its length through an opening in the wall of the catheter.

In yet another embodiment, a loop with an aperture therein may be attached to the catheter. In this embodiment, the guide member passes through the loop to guide the catheter along the length of the guide member. Those skilled in the art will appreciate that there are a variety of other ways to permit the sling application catheter to travel along the guide member, and the present invention contemplates such additional approaches.

Preferably, the sling application catheter is long enough to span between an insertion site in the patient's body and an exit site in the patient's body. The insertion site and exit site are positioned on either side of the location to which the sling is to be delivered.

The catheter may be a continuous cylinder with a lumen extending therethrough. Alternatively, the surface of the catheter may be partially open with a slot therein which is narrower than the width of the guide member, suture or other guiding device. Preferably, the distal end of the catheter has a tapered tip to facilitate its passage through the body tissue.

The pouch permits the sling to be handled without damage, maintains a barrier preventing microorganisms from contacting the sling, provides handling flexibility, and ensures that the sling is introduced into the opening or pocket in the patient's body tissue in the desired orientation. The pouch may be made of a variety of materials such as polyethylene terephthalate (PET), polyethylene (PE), vinyl, polyester and ethylene vinyl acetate (EVA). Preferably, the pouch is made of PET.

Preferably, the pouch is flat to facilitate delivery of the sling in a flat orientation. However, the pouch may also be conical, or rolled conical, and be provided with means for flattening the sling after delivery. Alternatively, the sling application catheter may be used in conjunction with slings made from materials which adopt a flat configuration after delivery.

Preferably, the pouch is clear or translucent to permit visualization of the sling within. In some embodiments, the pouch is made of a porous material such as polyethylene, polyethylene terephthalate or vinyl. In one embodiment, the pouch is adapted to receive a sling long enough to pass between a first suprapubic incision on one side of the urethra and a second suprapubic incision on the opposite side of the urethra.

In an alternative embodiment, the pouch may be adapted to receive a sling having a shorter length than the slings used with the embodiment described above. Such slings are attached to the pubic bone by sutures.

Long and short slings suitable for use with the present invention are described in the copending U.S. patent application entitled "Stabilization Sling for Use in Minimally Invasive Pelvic Surgery" (VESITEC.023A), filed simultaneously herewith, and the identically titled U.S. Provisional Patent Application Serial No. 60/038,379, filed Feb. 13, 1997, the disclosures of which are incorporated herein by reference.

The length of the pouch may be varied depending upon the length of the sling with which the sling application catheter is to be used.

Figure 15:
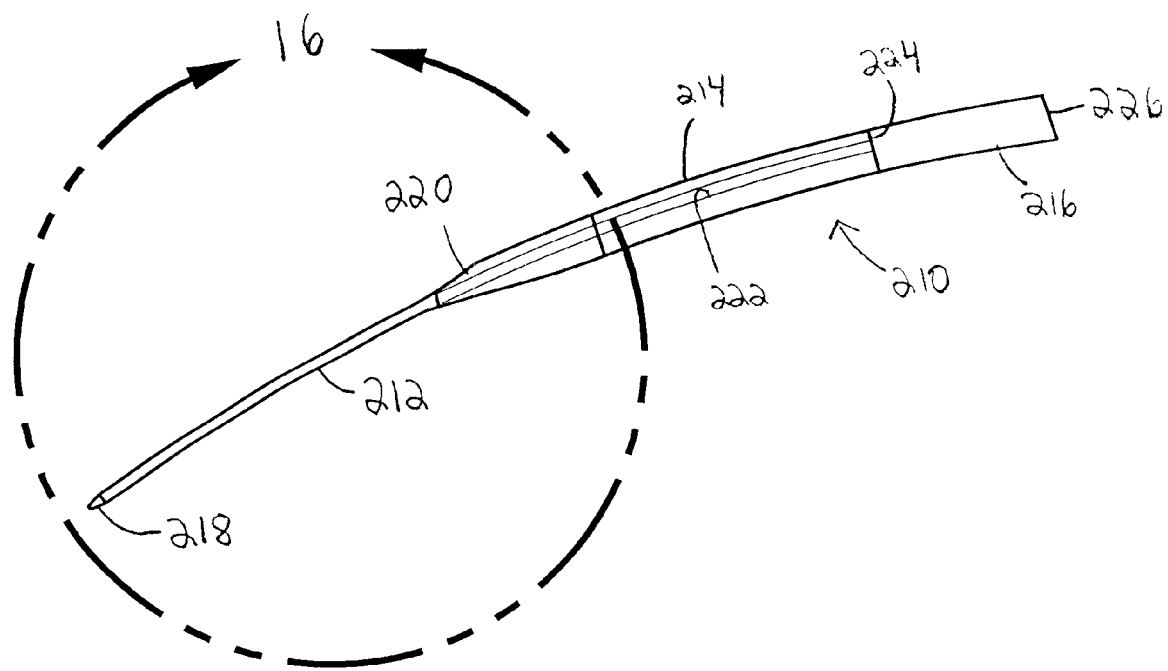
FIG. 15 is a plan view of a sling application catheter.

One embodiment of a sling application catheter 210 according to the present invention is shown in FIGS. 15 and 16. The sling application catheter of FIG. 15 comprises a catheter 212 and a pouch 214 adapted to releasably engage a sling 216 attached thereto. The distal end 218 of the catheter is tapered and extends beyond the distal end 220 of the pouch. The distal end 220 of the pouch is also tapered to facilitate its passage through the patient's body tissue. A lumen 222 extends through the catheter.

A cross section of the sling application catheter 210 of FIG. 15 with a sling 216 inside the pouch 214 is shown in FIG. 17. The sling 216 depicted in FIG. 15 is sufficiently long to pass between two suprapubic incisions on opposite sides of the urethra. Preferably, the sling 216 extends beyond the proximal end 224 of the pouch of the sling application catheter to permit the proximal end 226 of the sling to be grasped or secured.

Alternatively, shorter slings which are attached to the pubic bone via sutures may be used. The sling 216 may have sutures or integral attachment members extending bilaterally therefrom. Long and short slings suitable for use with the present invention are disclosed in the copending U.S. patent application entitled "Stabilization Sling for Use in Minimally Invasive Pelvic Surgery" (VESITEC.023A), filed simultaneously herewith, and the identically titled U.S. Provisional Patent Application Serial No. 60/038,379, filed Feb. 13, 1997, the disclosures of which are incorporated herein by reference. In such an arrangement, a suture or integral attachment member extends beyond the proximal end 224 of the pouch and can be grasped or secured by the physician to withdraw the sling from the pouch.

As illustrated in FIGS. 18 and 19, in alternative embodiments of the sling application catheter 310, the pouch 314 has a reinforcing stiffener 328. The reinforcing stiffener 328 may be on the interior or the exterior of the pouch 314. The stiffener 328 provides rigidity and prevents distortion of the sling 316 during passage through the patient's body tissue, as well as permitting the sling application catheter 310 to dilate or tear an opening in the patient's body tissue as it passes therethrough. In this manner, the sling application catheter 310 may be used to create an opening in the tissue between the urethra and the upper vaginal wall in which the sling is introduced. The stiffener 328 may also provide a bending effect which permits the sling to follow an axial bend along its width. Finally, the stiffener 328 reduces damage to the sling material during handling.

The stiffener 328 may be made of any of a variety of materials compatible with the above described considerations such as polyethylene, polypropylene, or acrylic. Preferably, the stiffener 328 provides approximately a 1 cm radius of bending.

In some embodiments, the stiffener 328 is made of a porous material such as polyethylene or polyethylene terephthalate having pores which permit a solution to access the sling during a soak as described below.

Preferably, the sling 216 introduced into the opening in the patient's body is sterile. In this regard, FIG. 20 depicts a further embodiment of the sling application catheter 410, in which the pouch 414 has pores 411 to permit rehydration of slings made of natural materials and antibiotic or saline soaks of the sling in the pouch prior to introduction of the sling into the patient. In this embodiment, the pouch 414 may be made of a variety of materials, such as PE, PET or vinyl. Preferably, the porous material has pore sizes ranging from about 100 microns to about 0.25 inches. Preferably, the pouch 414 is made of vinyl having a pore size of 0.125 inches.

The sling application catheters described above may be used in a variety of procedures in which delivery of a sling to an opening or pocket in the patient's body tissue is desired. A representative method in which the sling application catheter of FIGS. 15–20 are used to deliver a sling in a bladder neck stabilization procedure is described below and depicted in FIGS. 21–23. While the procedure is described with particular reference to the sling application catheter 210 of FIG. 15, those skilled in the art will appreciate that the sling application catheters 310, 410 of FIGS. 18 and 20 may also be used in the procedure.

Figure 21:
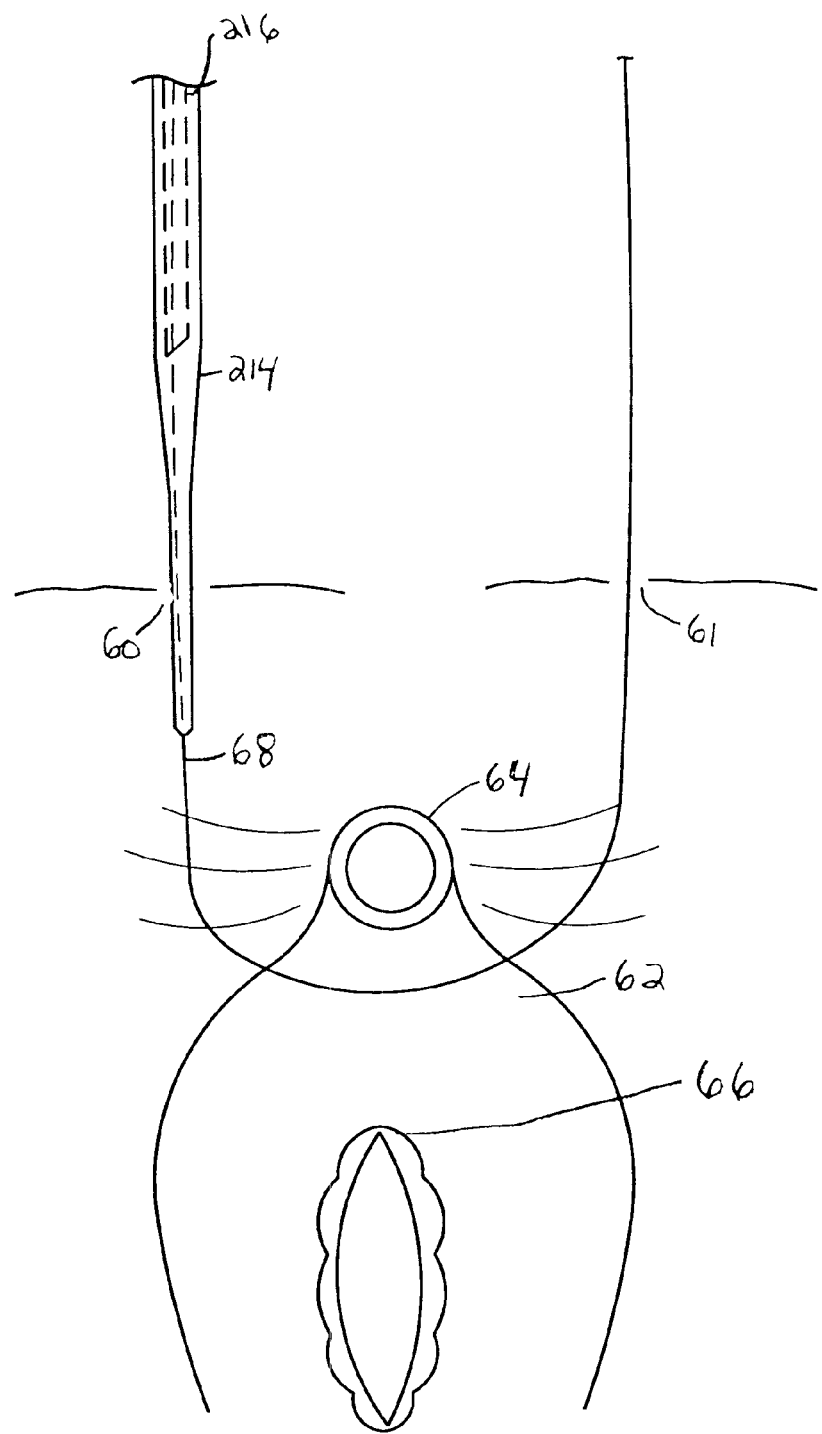
FIG. 21 shows a sling application catheter being inserted into a first suprapubic incision with a guide member extending through the lumen of the catheter.

A guide member 68 is introduced into the tissue between the urethra and the upper vaginal wall using a device such as the guide member placement devices 10, 1910 described above. As illustrated in FIG. 21, the guide member extends between two suprapubic incisions 61 and 62 on opposite sides of the urethra 64. As shown in FIG. 21, the end of the guide member 68 extending from the first suprapubic incision 60 in the patient's body is inserted into the lumen 222 of the catheter 212 such that the guide member passes 68 entirely through the catheter 212. A sling 216 capable of passing beneath the urethra and through the abdominal tissue on opposite sides of the urethra 64 is inserted into the pouch 214 such that the proximal end 226 of the sling extends from the proximal end 224 of the pouch.

Alternatively, a shorter sling 216 may be used. Such shorter slings may be attached to the pubic bone by sutures. In this embodiment, the sling may have sutures or integral attachment members extending bilaterally and may be inserted into the pouch so that a suture or integral attachment member extends from the proximal end of the pouch.

Long and short slings suitable for use with the sling application catheter are described in the copending U.S. patent application entitled "Stabilization Sling for Use in Minimally Invasive Pelvic Surgery" (VESITEC.023A), filed simultaneously herewith, and the identically titled U.S. Provisional Patent Application Serial No. 60/038,379, filed Feb. 13, 1997, the disclosures of which are incorporated herein by reference.

Figure 22:
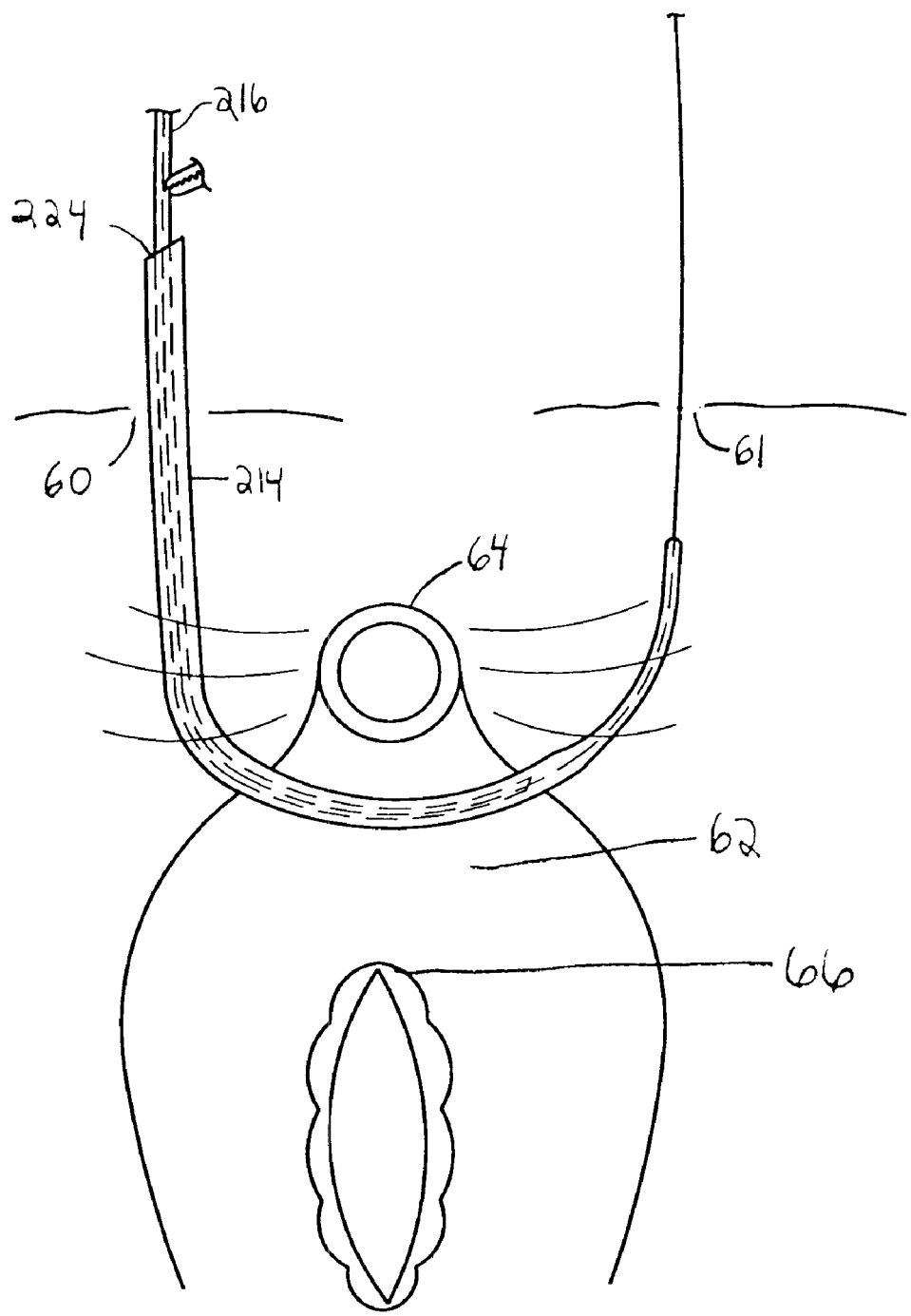
FIG. 22 shows the sling being withdrawn from the pouch of a sling application catheter that has been advanced into the tissue between the urethra and the upper vaginal wall.
Figure 23:
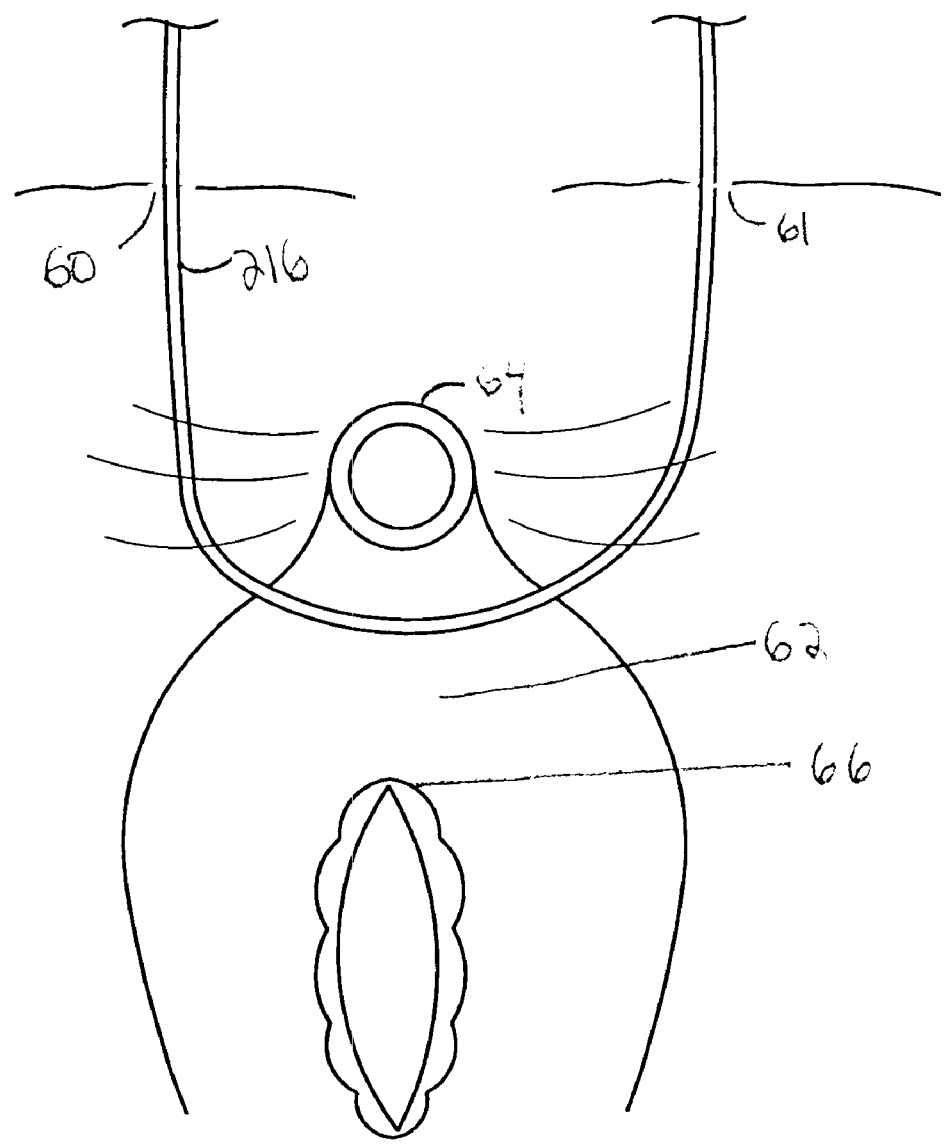
FIG. 23 shows the sling extending between the first and second suprapubic incisions and passing through the tissue between the urethra and the upper vaginal wall.

The physician percutaneously inserts the sling application catheter and advances it along the guide member. For example, the sling application catheter may be inserted through a first suprapubic incision 60. As the pouch 214 passes beneath the urethra 64, the physician grasps the portion of the sling or the suture or integral attachment member extending from the proximal end of the pouch while continuing to advance the sling application catheter 210, causing the sling 216 to be withdrawn from the pouch 214 as illustrated in FIG. 22. The sling application catheter is advanced until it exits the patient's body at a second suprapubic incision 61, leaving the sling extending between the first 60 and second 61 incisions as shown in FIG. 23.

Alternatively, when the shorter slings are used, the sutures or integral attachment members extend from the first and second incisions.

Following the completion of the preceding procedures, the sling 216 is located in the tissue 62 between the urethra and the upper vaginal wall.

Following implantation, the sling or sutures or integral attachment members extending therefrom may be sewn, stapled, riveted, or anchored to any of a variety of structures, such as the pubic bone, Cooper's ligament or rectus fascia to stabilize or stabilize the bladder neck or to stabilize the pelvic floor. For example, the long sling may be attached directly to the pubic periosteum using staples, clips, or sutures or may be attached to the pubic bone with short sutures attached to a bone anchor implanted in the pubic bone or fastened to the pubic bone with a headed nail or screw-like anchoring device.

The slings may be used to stabilize the bladder neck as described in the copending U.S. patent application entitled "Stabilization Sling for Use in Minimally Invasive Pelvic Surgery" (VESITEC.023A), filed simultaneously herewith, and the identically titled U.S. Provisional Patent Application Serial No. 60/038,379, filed Feb. 13, 1997. The tension on the sling may be adjusted as appropriate, using approaches such as those described in U.S. Pat. No. 5,611,515, issued Mar. 18, 1997 to Benderev et al., the disclosure of which is incorporated herein by reference, to support the bladder neck or stabilize the urethral floor, thereby maintaining or improving urinary continence.

Tissue Dissector/Dilator

Another aspect of the present invention is a tissue dissector/dilator 510 for creating an opening or pocket in a body tissue and dilating the opening or pocket with an expandable dilator. The tissue dissector/dilator finds particular application in urethral floor reconstruction procedures, such as bladder neck stabilization procedures in which the tissue between the female urethra and the upper vaginal wall is dissected and dilated to facilitate placement of a therapeutic sling device designed to alleviate incontinence.

The tissue dissector/dilator can be used in percutaneous approaches in which the sling is introduced into an opening or pocket in the tissue between the urethra and the upper vaginal wall without entry of the vaginal canal. Such procedures are described in detail below.

The tissue dissector/dilator generally comprises a body with a non-compliant shaft attached thereto. Preferably, the shaft has at least one lumen extending therethrough.

A dissector for creating an opening or pocket in the body tissue is carried on the shaft. The dissector may be on the exterior of the shaft or in the interior. Preferably, the dissector is within the lumen of the shaft and is axially movable such that it is capable of being extended from and retracted in the shaft to create an opening in the body tissue.

A dilator for dilating the opening or pocket is also carried on the shaft. The dilator may be on the exterior of the shaft or in the interior. Preferably, the dilator is within the lumen of the shaft and is axially movable such that it is capable of being extended from and retracted in the shaft. Preferably, the dilator is expandable and collapsible.

Preferably, the dissector and the dilator are integral. Alternatively, the movable dissector and the dilator can be separate elements of the tissue dissector/dilator. Preferably, both the dissector and the dilator are axially movable.

In yet another embodiment, the dissector and the dilator are not integral parts of the tissue dissector/dilator. In this embodiment, the dissector and the dilator are distinct devices which can be inserted into the shaft of the tissue dissector/dilator at the point in the surgical procedure in which tissue dissection or dilation is required.

A representative embodiment of the tissue dissector/dilator 510 is shown in FIG. 24. As shown in FIG. 24 the body 512 comprises a trigger 514, a locking wheel 516, and a spring return button 518. In the embodiment of FIG. 24, the trigger 514 and the upper section 520 of the body each have a slot 522 and 524 therein which together define an aperture 526 adapted to receive a syringe 528 therein. However, those skilled in the art will appreciate that the body 512 can have a number of configurations compatible with the intended use of the tissue dissector/dilator and the present invention encompasses such additional configurations.

The spring return button 518 can slide along a slot in a vertical face of the body. As shown in FIG. 24, the spring return button 518 is biased towards a first position at the proximal end of the slot by a spring. As shown in FIG. 25, the spring return button 518 can slide to a second position in which it is locked in place. As illustrated in FIG. 25, in the locked position, the spring return button 518 fits into a groove on the body 512 and is located on a face of the body perpendicular to the face on which the spring return button 518 is located in the unlocked state.

The spring return button 518 may have an internal extension inside the body which has a proximal section adapted to receive a syringe tip.

As illustrated in FIG. 24, the shaft 530 is attached to the bottom portion 532 of the body 512 and has a lumen extending therethrough. The shaft 530 may be fabricated from a number of non-compliant materials sturdy enough to resist torque applied while the device is advanced through the body tissue. Preferably the shaft 530 is made of stainless steel.

Preferably, the shaft 530 curves towards its distal end 534. Preferably, the curve is a small radius curve. Preferably, the distal end 534 of the shaft is at an angle of about 90° relative to the proximal portion of the shaft. However, those skilled in the art will appreciate that the curve in the shaft 530 may vary depending on anatomical considerations and the type of procedure in which the tissue dissector/dilator is to be used.

Figure 26:
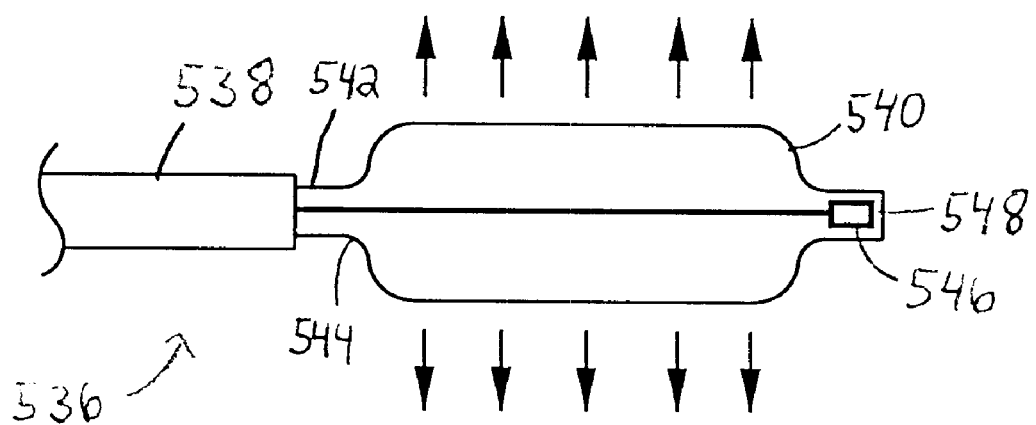
FIG. 26 is a side view of a balloon catheter with a blunt dissection tip at its distal end.

As shown in FIG. 25, a balloon catheter 536 is located within the lumen of the shaft 530 and is engaged by the spring return button 518. As illustrated in FIG. 26, the balloon catheter 536 comprises an outer tube 538 having a lumen extending therethrough and an expandable balloon 540 in the lumen of the outer tube 538. An inflation tube 542 with a lumen therein is located at the proximal end 544 of the expandable balloon and is in fluid communication with the interior of the balloon 540. Preferably, the expandable balloon 540 has a blunt dissection tip 546 at its distal end 548.

The inflation tube 542 may be made of any of a number of materials, such as PE or PET. Preferably, the inflation tube 542 is made of a non-compliant or minimally compliant material.

In the embodiment of FIG. 26, the expandable balloon 540 has a cylindrical shape when expanded. Preferably, the dimensions of the balloon are adapted for dilating an opening or pocket in the tissue between the urethra and the upper vaginal wall. The length of the balloon is dependent upon the direction in which it is oriented relative to the urethra in the procedure being used to create the pocket or opening. When the balloon is oriented perpendicular to the urethra the balloon is preferably 4–6 cm in length, with an effective width of 2 cm to create a pocket or opening of approximately 5 cm in length and 2 cm in width.

When used in procedures in which the balloon is oriented parallel to the urethra the balloon may be shorter than those used in procedures in which the balloon is perpendicular to the urethra. Balloons used in such procedures may also have a larger diameter than those used in procedures in which the balloon is perpendicular to the urethra. Balloon catheters having a plurality of balloons side by side or flat profile balloons, such as those described in more detail below, are also well suited for such procedures.

Preferably, the balloon expands radially but does not increase in length when expanded.

The blunt dissection tip 546 is preferably cylindrical in shape. Preferably, the blunt dissection tip 546 is about ¼ inch in length.

The blunt dissection tip 546 may be fabricated from a variety of materials which are rigid enough to facilitate their use in blunt dissection of a body tissue. The tip of the balloon may be formed into a solid tip which functions as the blunt dissection tip. Alternatively, the blunt dissection tip 546 may comprise the same material as the inflation tube 542. In yet another embodiment, the blunt dissection tip may be stainless steel.

The balloon catheter may also have a second lumen therein for receiving a guide member. In this embodiment, a guide member may be placed through the aperture in the body, pass through the shaft, and extend out of the distal tip of the shaft, permitting the tissue dissector/dilator to be used to place a guide member in the opening or pocket created in the body tissue. The guide member may be a suture, guidewire, or other structure suitable for guiding a sling to a desired location.

In another embodiment, the balloon catheter may have a third lumen therein for irrigation or for receiving diagnostics, such as an ultrasound catheter. The third lumen may also be used for passage of an implant, such as fibrin glue or a bladder neck suspension or stabilization sling, such as those described in the copending U.S. patent application entitled "Stabilization Sling for Use in Minimally Invasive Pelvic Surgery" (VESITEC.023A), filed simultaneously herewith, and the identically titled U.S. Provisional Patent Application Serial No. 60/038,379, filed Feb. 13, 1997, the disclosures of which are incorporated herein by reference.

As shown in FIG. 24, when the spring return button 518 is positioned at the most proximal point of its path in the vertical face of the body 512, the balloon catheter 536, including the blunt tip 546 and the expandable balloon 540, is retracted within inside the shaft 530. As illustrated in FIG. 27, when the spring return button 518 is moved towards the distal end of the slot, force is communicated to the balloon catheter 536 causing it to move axially towards the distal end 534 of the shaft, such that the blunt dissection tip 546 extends out of the shaft 530. If the spring return button 518 is then released, the bias from the spring will cause the spring return button 518 to return to the most proximal point of the slot, thereby returning the blunt dissection tip 546 to a fully retracted position within the shaft 530. Preferably, the spring return button 518 provides a one to one stroke motion to the blunt dissection tip 546. When the spring return button 518 is locked at its most distal position, the expandable balloon 540 and the blunt dissection tip 546 protrude from the distal end 534 of the shaft, as shown in FIG. 25.

As shown in FIG. 24, the proximal end of the body is adapted to receive a syringe 528 therein. The syringe 528 comprises a plunger 550, a reservoir, and a tip. The tip of the syringe engages the proximal section of an internal extension of the spring return button 518. As illustrated in FIG. 25, when the spring return button 518 is placed in the locked position, the syringe 528 moves into the body 512 and is positioned so as to permit the plunger 550 to engage the trigger 514. The tip of the syringe contacts the locking wheel 516 and engages a luer connection thereon. When the locking wheel 516 is tightened, the syringe 528 is firmly fixed in place such that the reservoir of the syringe is in fluid communication with the lumen of the balloon catheter.

With the spring return button 518 in the locked position, the plunger 550 of the syringe engages the trigger 514, such that squeezing the trigger 514 causes the plunger 550 of the syringe to be depressed. When the reservoir of the syringe is filled with a fluid, such as sterile saline or sterile water, squeezing the trigger 514 causes the fluid to be dispensed from the syringe 528 into the lumen of the inflation tube 542, thereby inflating the expandable balloon as illustrated in FIG. 28. The trigger 514 contains a return spring, such that when the trigger 514 is released from the squeezed position, the trigger returns to its original position, drawing the plunger 550 of the syringe upward and thereby creating a vacuum in the syringe reservoir which draws the fluid from the expandable balloon 540 and deflates the balloon. The plunger 550 and the trigger 514 may be interconnected through a variety of structures familiar to those skilled in the art. For example, they may be interconnected through a rack and pinion gear.

Figure 29:
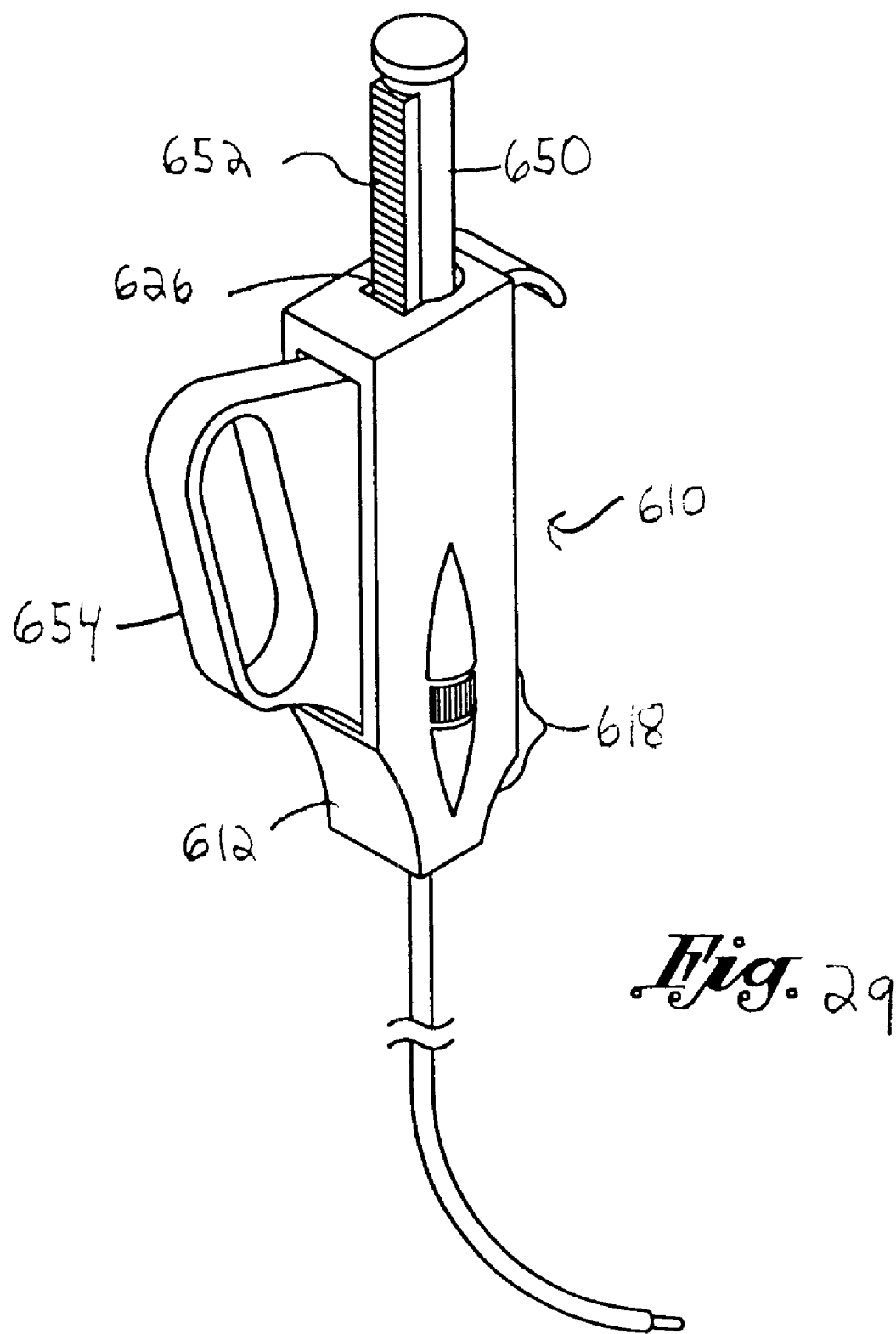
FIG. 29 is a plan view of an alternate embodiment of the tissue dissector/dilator.

An alternative embodiment of the tissue dissector/dilator 610 is shown in FIG. 29. In this device, the trigger 654 has an alternate shape as shown in FIG. 29 and engages a set of teeth 652 on the plunger 650 of the syringe. The body has a central aperture 626 therein which receives the syringe. Additionally, in this embodiment the locked position of the spring return button 618 is close to the bottom of the body 612 and the spring return button 618 is on the same face of the body in its locked and unlocked states.

While several embodiments of the tissue dissector/dilator have been described above, those skilled in the art will appreciate that alternative configurations are compatible with the function of the device. Such additional configurations are within the scope of this invention.

The following section describes the use of the tissue dissector/dilator in the context of a percutaneous bladder neck stabilization or suspension procedure in which a sling is utilized for treating urinary incontinence in females. However, those skilled in the art will recognize that the tissue dissector/dilator may also find application in a variety of other procedures in which it is necessary to introduce an opening into a body tissue and subsequently dilate that opening. While the procedure is described with particular reference to the tissue dissector/dilator 510 shown in FIGS. 24, 25, 27 and 28, those skilled in the art will appreciate that the tissue dissector/dilator 610 shown in FIG. 29 may also be used in the procedure.

The shaft of the tissue dissector/dilator is inserted percutaneously. For example, percutaneous insertion may be through a one inch transverse incision made over a pubic tubercle with dissection is carried down to the area of the rectus fascia. The tissue dissector/dilator 510, 610 is guided through the patient's body tissue along the back side of the pubic bone while maintaining the distal end of the shaft in contact with the pubic bone. If resistance is encountered while advancing the tissue dissector/dilator through tissue, the spring return button 518 may be repetitively partially depressed and allowed to return to its most proximal position through the action of the biasing spring. This process results in repetitive extension of the blunt dissection tip 546 out of the shaft 530 and retraction of the blunt dissection tip 546 back into the shaft 530, thereby dissecting an opening in the body tissue through which the device is passing.

Figure 30:
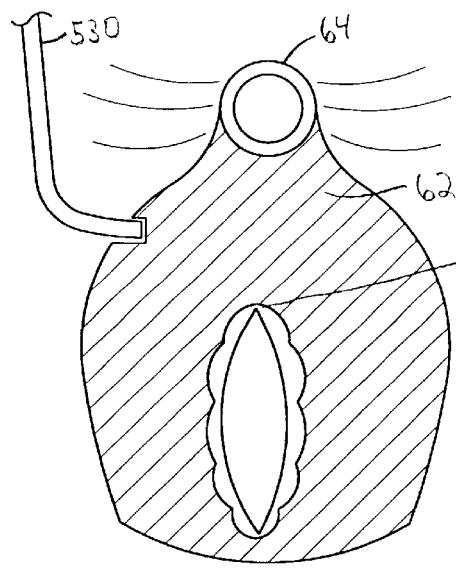
FIG. 30 shows the distal end of the shaft of a tissue dissector/dilator being advanced until it intersects the tissue between the urethra and the upper vaginal wall at approximately mid-thickness and in a direction which would permit the expandable balloon to advance perpendicular to the axial direction of the urethra.

The tissue dissector/dilator 510 is advanced until tenting is observed on the upper vaginal wall. As shown in FIG. 30, the user then manipulates the distal end of the shaft 534 until it intersects the tissue 62 between the urethra 64 and the upper vaginal wall 66 at approximately mid-thickness and in a direction which would permit the expandable balloon to advance perpendicular to the axial direction of the urethra.

Figure 31:
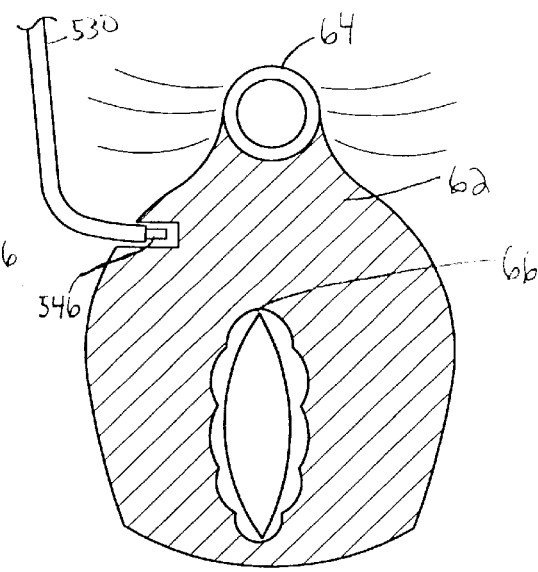
FIG. 31 shows the blunt dissection tip being extended from the distal end of the shaft into the tissue between the urethra and the upper vaginal wall thereby dissecting a first opening in the tissue.

As illustrated in FIG. 31, the tissue 62 between the urethra 64 and the upper vaginal wall 66 is then blunt dissected by repetitively extending and retracting the blunt dissection tip 546 using the spring return button 518 as described above, thereby creating an opening in the tissue. The dissection process is repeated until an opening is created in the tissue 62 which is large enough to permit the expandable balloon 540 to be fully extended from the shaft 530 such that the distal end of the shaft extends transversely between the urethra 64 and the upper vaginal wall 66 in the plane defined by the longitudinal axes of the urethra and the vagina, as shown in FIG. 32.

Figure 32:
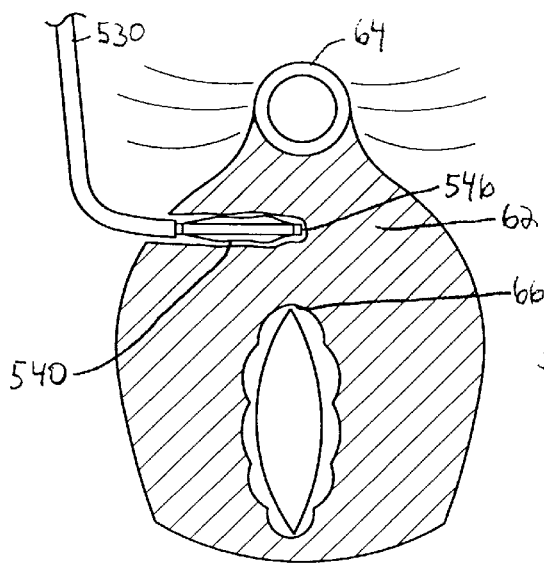
FIG. 32 shows the expandable balloon extended into the first opening in the tissue between the urethra and the upper vaginal wall which was created with the blunt dissection tip.
Figure 33:
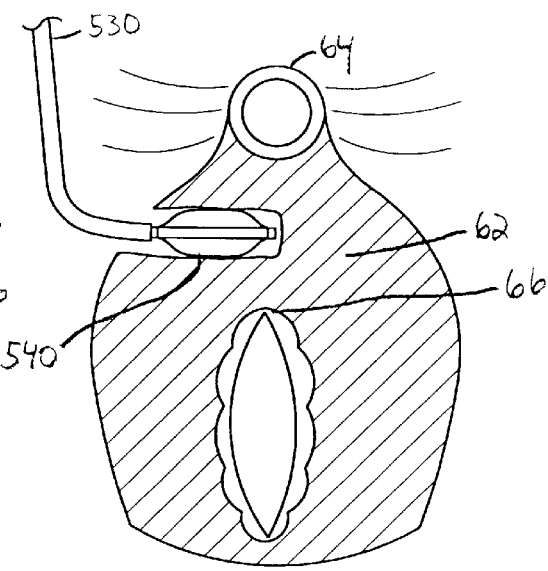
FIG. 33 shows the balloon being expanded in the first opening in the tissue thereby dilating the first opening.

The spring return button 518 is advanced to its locked position in which the expandable balloon 540 is fully extended into the opening in the body tissue, as shown in FIG. 32. The syringe 528 is locked in place such that its reservoir is in fluid communication with the lumen of the inflation tube 542 of the balloon catheter 536 and its plunger 550 engages the trigger 514. The trigger 514 is squeezed to dispense the saline solution inside the reservoir of the syringe through the inflation tube 542 of the balloon catheter 536 and into the expandable balloon 540, causing the balloon 540 to expand. Expansion of the balloon 540 dilates the body tissue, creating a first opening therein as shown in FIG. 33.

The trigger 514 is then released and is returned to its original position through the action of the return spring. As the trigger returns to its original position, a vacuum is created in the reservoir of the syringe 528, thereby drawing the fluid out of the expandable balloon 540 and causing the balloon 540 to deflate.

The trigger 514 can be squeezed and released multiple times, if necessary, until the opening in the body tissue expands. The expandable balloon 540 and blunt dissection tip 546 are then retracted into the shaft 530.

Figure 34:
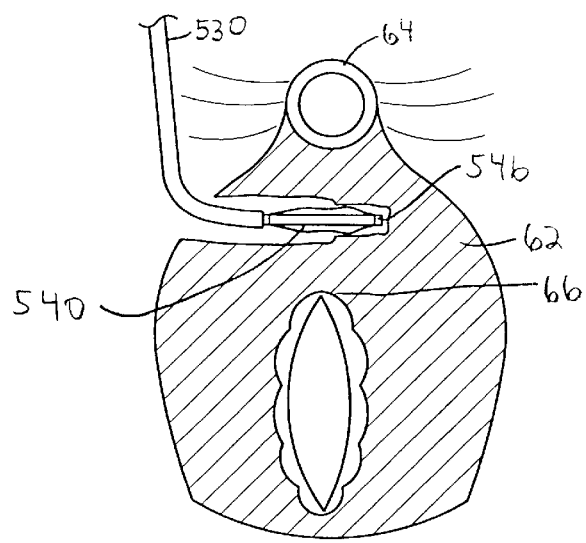
FIG. 34 shows a second tissue dissector/dilator with its blunt tip dissecting a second opening in the tissue between the urethra and the upper vaginal wall which is aligned with the first opening in the tissue.
Figure 35:
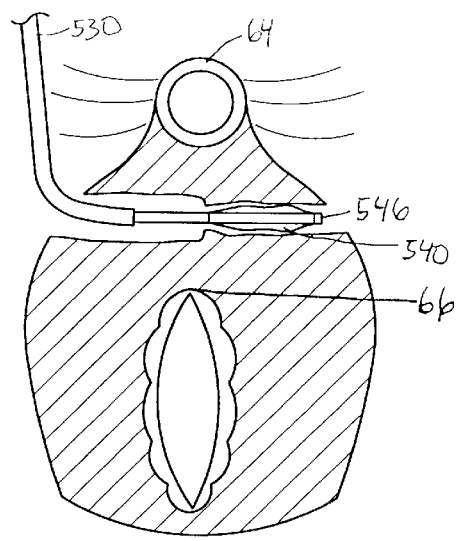
FIG. 35 shows the expandable balloon extended into the second opening.
Figure 36:
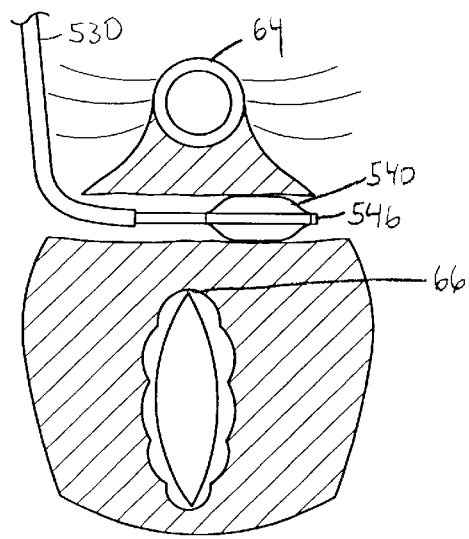
FIG. 36 shows the expandable balloon expanded within the second opening thereby dilating the body tissue.
Figure 37:
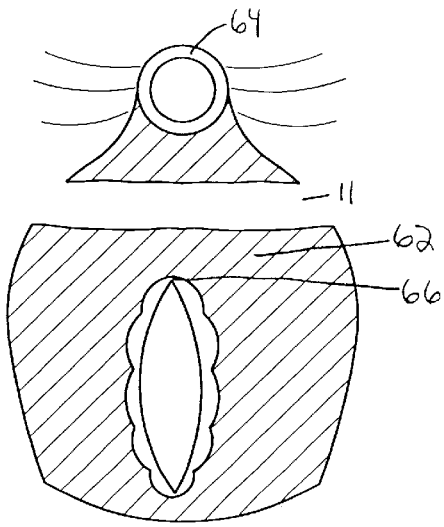
FIG. 37 shows a continuous opening in the tissue between the urethra and the upper vaginal wall.

The above dissection and expansion steps can be repeated while advancing the tissue dissector/dilator through the tissue between the urethra and the upper vaginal wall, as shown in FIGS. 34–36. The dissection and expansion steps may be repeated until a continuous dilated opening or pocket 11 exists in the tissue 62, as shown in FIG. 37. Following the creation of the continuous dilated opening or pocket, the tissue dissector/dilator is removed from the patient's body.

Alternatively, the continuous dilated opening or pocket 11 can be created from both sides of the urethra. In this procedure, a first tissue dissector/dilator is advanced approximately to the midline of the urethra while dissecting and expanding the tissue 62 as described above to create a first opening in the body tissue. The first tissue dissector/dilator may be removed from the body, or, in the embodiments described below in which two tissue dissector/dilators are interconnected to pass a guide member or suture through the patient's body, the first tissue dissector/dilator may remain in the patient's body.

A second tissue dissector is percutaneously inserted. This may be accomplished through a second suprapubic incision made on the opposite side of the urethra from the first suprapubic incision. A second tissue dissector/dilator 510 is inserted into the second incision and advanced through the body tissue until it is aligned with the first opening in the body tissue. Correct alignment of the second tissue dissector/dilator with the first opening in the body tissue is determined through visualization of tenting of the vaginal wall and through tactile sensation. The blunt dissector tip 546 of the second tissue dissector/dilator 510 is extended and retracted from the shaft 530, thereby creating a second opening in the body tissue which is joined to the first opening in the body tissue. The expandable balloon 540 is extended into the second opening and expanded within the second opening, thereby dilating the body tissue. When the second tissue dissector/dilator 510 is removed from the patient's body a continuous dilated opening or pocket 11 exists in the tissue 62, as shown in FIG. 37.

In both of the above methods, a sling may be introduced into the opening or pocket using the sling application devices described herein to suspend or stabilize the pelvic floor.

In the embodiment in which the balloon catheter has a second lumen for receiving a guide member, the tissue dissector/dilator may be used to introduce a guide member as follows. After creation of the first opening or pocket but before removal of the first tissue dissector/dilator from the body, a guide member, suture, guide catheter, or webbing is introduced into the second lumen of the catheter. When the first tissue dissector/dilator is removed from the body, the guide member is left in place.

After creation of the continuous pocket but before removal of the second tissue dissector/dilator from the body, the guide member in the first pocket is introduced into the second lumen of the catheter of the second tissue dissection/dilator and advanced therethrough. When the second tissue dissector/dilator is removed from the body after creation of the continuous pocket, the guide member remains in place and extends between both suprapubic incisions, passing under the urethra and through the continuous pocket. Alternatively, the tissue dissector/dilator may have an engaging member at the distal end of the shaft, permitting two devices to be interconnected with their lumens in fluid communication as described above for the guide member placement device. In this embodiment, the guide member, suture, guide catheter, or webbing is passed through the interconnected lumens of the first and second tissue dissector/dilators as described above in regard to the guide member placement device. Thus the guide member, suture, guide catheter or webbing extends between the two suprapubic incisions and passes through the tissue between the urethra and the upper vaginal wall.

The guide member can then be used to introduce a sling into the opening or pocket as described above.

In yet another embodiment, the tissue dissector/dilator may be used in transvaginal procedures. For example, the tissue dissector/dilator may be inserted through the upper vaginal wall rather than through suprapubic incisions. In this embodiment the device is advanced into the tissue 62 between the urethra and the upper vaginal wall and the balloon is expanded to create an opening or pocket as described above.

Sling Application Device and Sling Application System

Another aspect of the present invention is a sling application device for inserting a sling into an opening or pocket in a body tissue. The sling application device provides access to the tissue between the urethra and the upper vaginal wall and introduces a sling into a pocket or opening in that tissue. In some embodiments, the sling application device creates the pocket or opening into which the sling is inserted. In other embodiments, the sling application device introduces the sling into a pre-formed pocket or opening. The device may be used in percutaneous methods alone or in laparoscopic procedures.

Another sling application device for introducing a sling into the tissue between the urethra and the upper vaginal wall is currently available. This device comprises two shafts, each having a central lumen, which can be clamped together via horizontally extending tabs present at the proximal end of each shaft. Rotation of a lever on one of the horizontal tabs clamps the two tabs together, thereby locking the two shafts to one another.

The currently available device is used to introduce a sling into the tissue between the urethra and the upper vaginal wall as follows. The two shafts are introduced into incisions on opposite sides of the urethra in the unlocked configuration. The shafts are advanced through the patient's tissue until they are located underneath the urethra with the lumens of the two shafts aligned. The lever is then rotated to the locked position, fixing the two shafts together. A sharp blade is inserted through the lumen of one of the two shafts such that it contacts the tissue between the distal ends of the shafts. As the blade is advanced through the tissue between the distal ends of the shafts, the tissue is dissected. Eventually, the blade enters the lumen of the second shaft, thereby creating a continuous opening in the tissue between the urethra and the upper vaginal wall.

The two shafts are unlocked and one of them is removed from the patient's body. A suture is inserted into the eye of the blade and the blade is advanced into the opening in the tissue between the urethra and the upper vaginal wall. A right angle clamp is then used to grasp and follow the suture into the tissue between the urethra and the upper vaginal wall. When the jaws of the right angle clamp are spread, an enlarged opening sized to receive a sling is created. The sling is then guided along the suture and introduced into the enlarged opening.

As will be apparent from the following description, the present sling application device provides several advantages over the currently available device. For example, the present device eliminates the use of a right angle clamp to create the sling receiving opening which is required with the currently available device. Moreover, the sling introducer permits the sling application device to introduce the sling without the use of a guiding suture as required with the currently available device. A further advantage of the present device and methods for using the device is that when the pocket or opening is created by hydrodissection the procedure can be performed without cutting the tissue between the two shafts of the sling application device. Furthermore, with the present device, it is not necessary to seat the distal ends of the shaft together before locking the two halves of the device to one another.

The present sling application device generally comprises a first and a second shaft. The first and second shafts have a central lumen which is sized to allow a sling to advance therethrough. The lumens of the first and second shafts may also be sized to allow a sling introducer to pass therethrough. Preferably, the shafts of the present sling application device are sufficiently wide to create or maintain an opening in the tissue capable of receiving the sling.

Preferably, the sling application device further comprises a first handle attached to the first shaft and a second handle attached to the second shaft. The first and second handles have openings therein which are in fluid communication with the lumens in the shafts to which the handles are attached. Preferably, the first and second handles are adapted to be connected to one another.

The present sling application device includes an adjuster for incrementally adjusting the distance between the distal ends of the first and second shafts. The adjuster allows the distance between the distal ends of the shafts to be slowly decreased while monitoring the patient to ensure that the urethra is not pinched during the procedure. This feature is absent from the currently available device, which has only two configurations, the locked and unlocked configurations described above. Preferably, the adjuster engages the first and second handles.

Preferably, the upper portions of the distal ends of the first and second shafts are indented relative to the lower portions of the distal ends to reduce the possibility of pinching of the urethra during the sling implantation procedure. This feature is absent from the currently available device, increasing the risk of damage to the urethra when that device is used.

The shafts of the present sling application devices are adapted to receive several components during the sling application procedure such that the sling application device can be used as part of a sling introduction system. The sling introduction system generally comprises the sling application device, a blunt dissector and a sling introducer. In some embodiments, the sling introduction system may further comprise a sharp tissue cutter.

Figure 38:
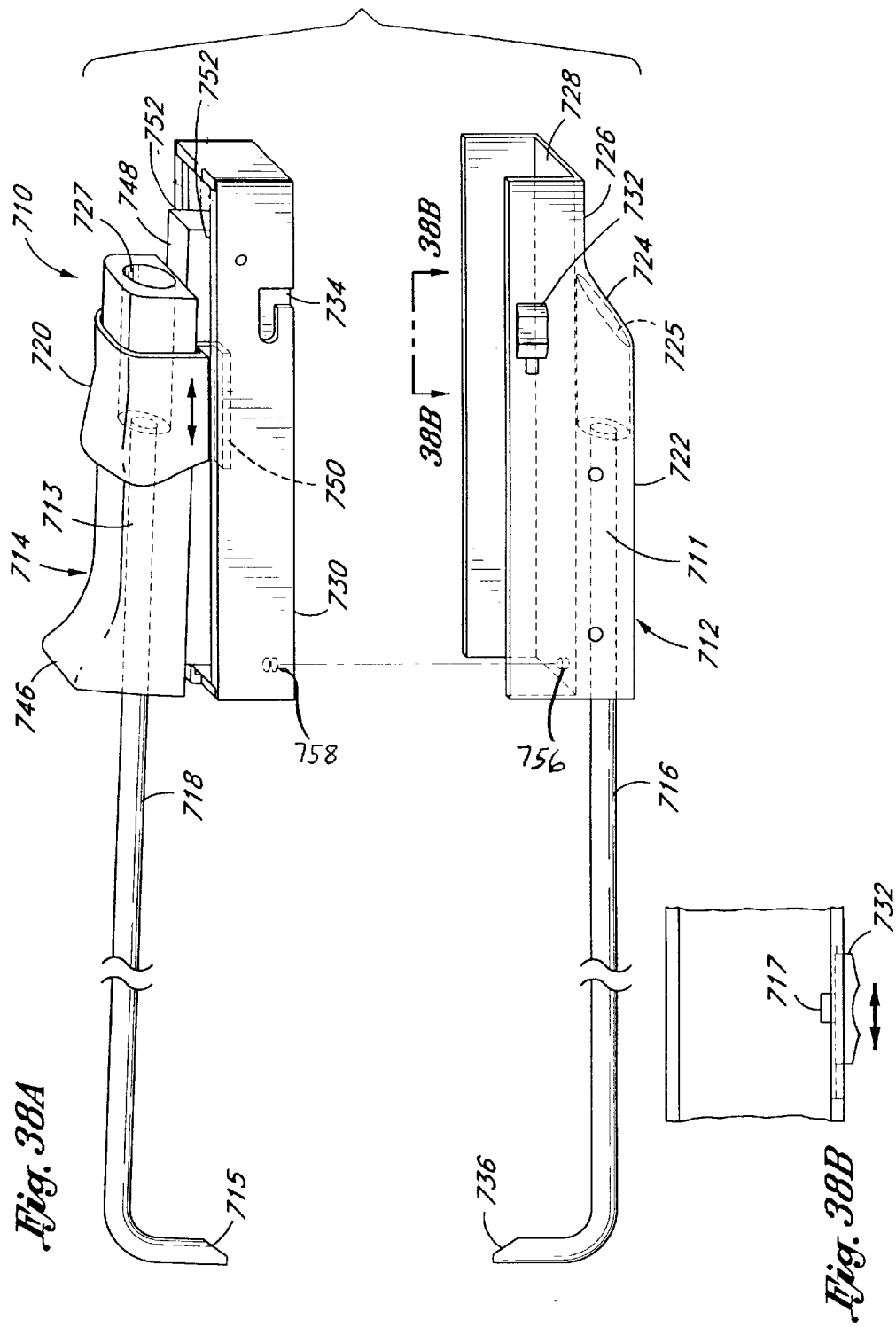
FIG. 38A is a perspective view of a sling application device.
FIG. 38B is a plan view taken along line 38B—38B of the sling application device of FIG. 38A showing the tab on the locking button.

A representative embodiment of the sling application device 710 is shown in FIG. 38A. As shown in FIG. 38A, the sling application device 710 comprises a first handle 712 and a second handle 714, having first 716 and second 718 shafts, respectively, attached thereto. The first and second handles have openings 725, 727 and therein which are adapted to receive a sling or sling introducer. The first and second shafts 716, 718 are adapted for insertion into a body tissue and have central lumens 711 and 713, respectively, which extend therethrough. The lumens of first and second shafts are in fluid communication with the openings in the first and second handles and are adapted to receive a sling or sling introducer. The first and second shafts 716, 718 have dimensions adapted for creating or maintaining a pocket or opening in the body tissue and for receiving a sling introducer. The sling application device also comprises an adjuster 720 for adjusting the distance between the first shaft 716 and the second shaft 718. Preferably, the adjuster 720 is an articulating lock.

As shown in FIG. 38A, the first handle 712 has a generally rectangular distal portion 722, an indented region 724, and a generally rectangular proximal portion 726 having a width less than the width of the generally rectangular distal portion 722. One face of the first handle 712 has a rectangular recess 728 open at each end for receiving an extension 730 on the second handle.

As shown in FIG. 38B, the first handle has a locking button 732 with a tab 717 thereon which is adapted to engage a groove 734 in the extension 730 section which is disposed between the first handle 712 and the second handle 714, thereby locking the two handles together. Alignment of the first handle 712 with the second handle 714 during locking is achieved by placing alignment pin 756 in alignment hole 758. However, those skilled in the art will appreciate that other means for aligning the handles and locking them together may also be used.

Figure 39:
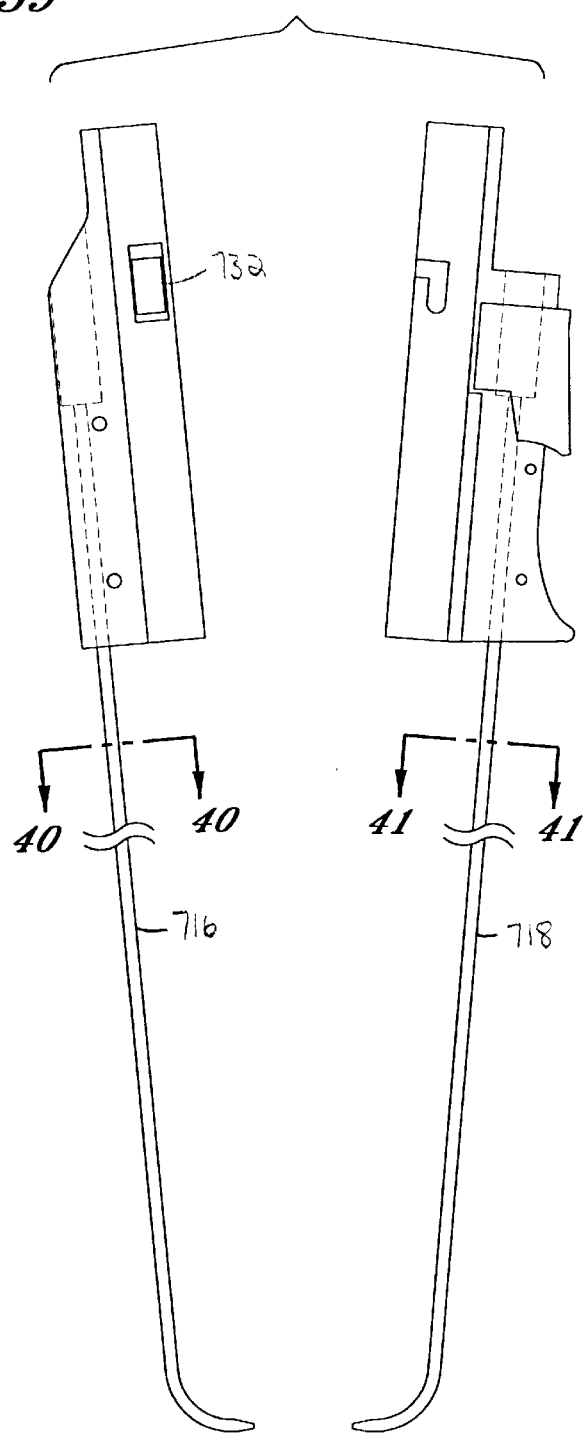
FIG. 39 is a side-view of the sling application device.
Figure 40:
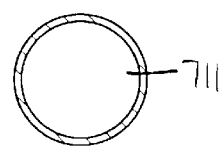
FIG. 40 is a cross-sectional view taken along line 40—40 of the first shaft of the sling application device of FIG. 39.
Figure 41:
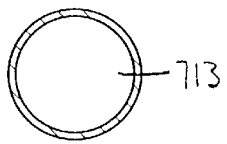
FIG. 41 is a cross-sectional view taken along line 41—41 of the second shaft of the sling application device of FIG. 40.

A first shaft 716 with a central lumen therethrough extends through the first handle 712. As shown in FIGS. 39,

40 and 41, the first shaft 716 is cylindrical and curves toward its distal end 736. The first shaft 716 may be from about 3 inches to about 10 inches in length, with an outer diameter from about 3/16 inch to about 5/8 inch with a wall thickness from about 0.010 inch to about 0.020 inch. Preferably, the first shaft 716 is from about 6 inches to about 8 inches in length, with an outer diameter from about 0.187 inch to about 0.275 inch. However, those skilled in the art will appreciate that the preceding dimensions may vary depending on anatomical considerations and the type of procedure being performed.

The first shaft 716 may be made of a variety of materials, including stainless steel and aluminum. Preferably, the first shaft 716 is made from stainless steel.

The first shaft 716 is curved near its distal end. Preferably, the first shaft 716 curves through an arc from about 80° to about 90°. More preferably, the first shaft 716 curves through an arc of about 90°.

Figure 42:
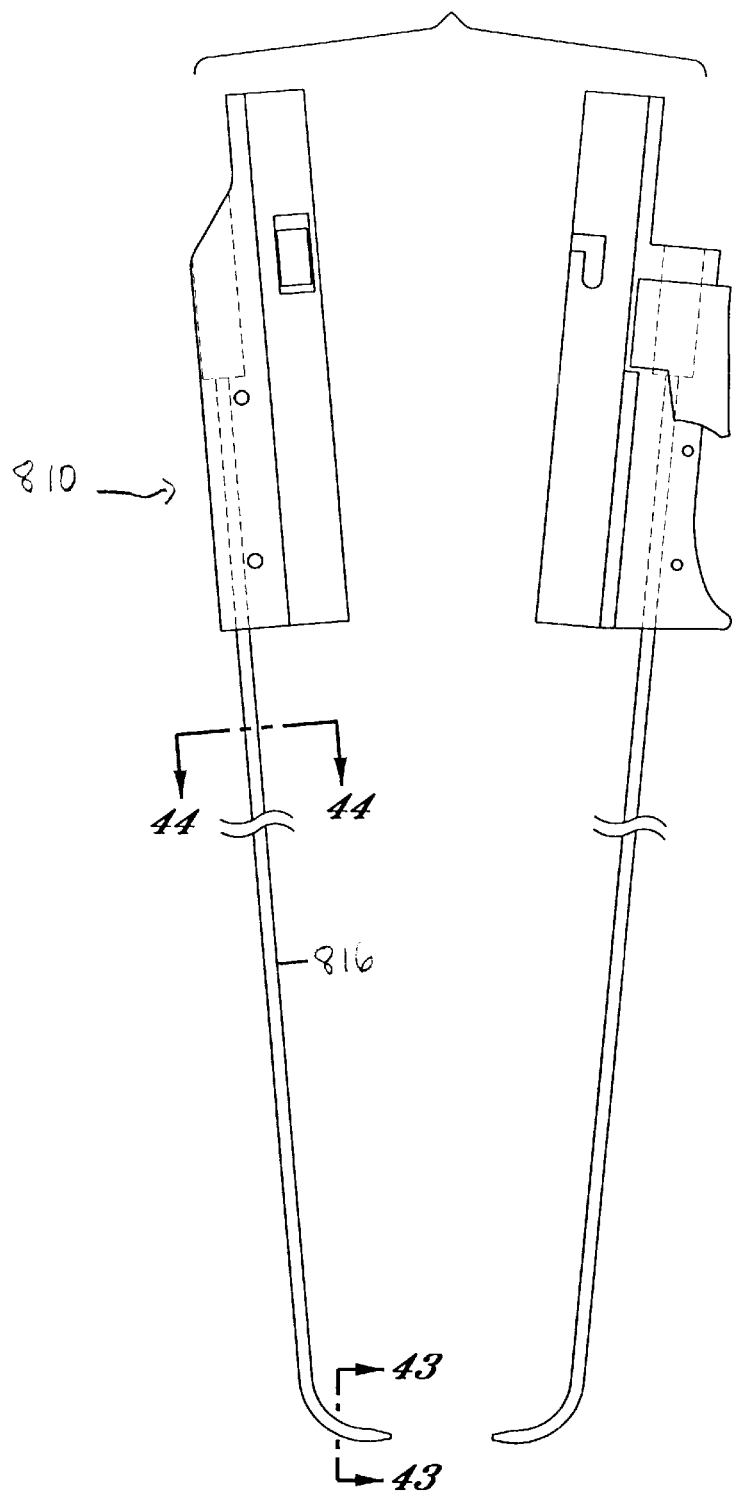
FIG. 42 is a side view of an alternate embodiment of the sling application device in which the portion of the shafts proximal to the bend is cylindrical and the portion of the shafts distal to the bend is a flat tube.
Figure 43:
FIG. 43 is a cross-sectional view taken along line 43—43 of the portion of the first shaft distal to the bend of the sling application device of FIG. 42.
Figure 44:
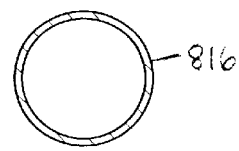
FIG. 44 is a cross-sectional view taken along line 44—44 of the portion of the first shaft proximal to the bend of the sling application device of FIG. 42.

In an alternate embodiment of the sling application device 810, shown in FIGS. 42, 43 and 44, the portion of the first shaft 816 proximal to the curve is cylindrical and the portion of the first shaft 816 distal to the curve is a flat tube. The flat tube may have a variety of cross sectional shapes such as rectangular, hexagonal or oval. The first shaft 816 is curved as described above for the embodiment in which the shaft is cylindrical.

Figure 45:
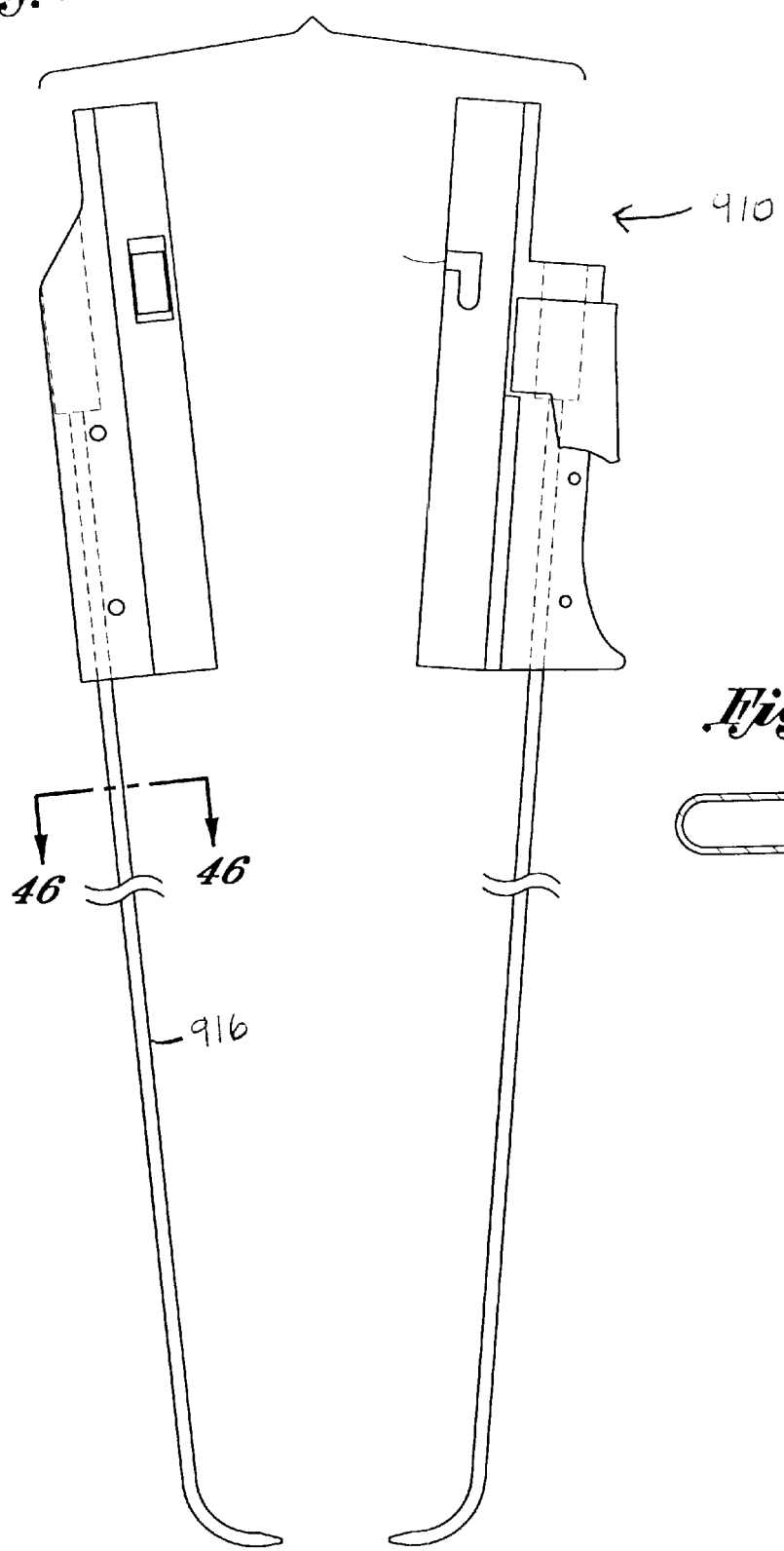
FIG. 45 is a side view of an alternate embodiment of the sling application in which the shafts are flat along their entire length.
Figure 46:
FIG. 46 is a cross-sectional view taken along line 46—46 of the first shaft of the sling application device of FIG. 45.

In a further embodiment of the sling application device 910, the first shaft 916 comprises a tube which is flat along its entire length as shown in FIGS. 45 and 46. The first shaft 916 is curved towards its distal end as described above for the embodiment in which the shaft is cylindrical.

Preferably, the first shaft has a side bend. In accordance with this embodiment, the first shaft can be flat, cylindrical, or flat in some portions and cylindrical in others as described above with respect to the sling application devices 710, 810, 910 discussed above.

Figure 47:
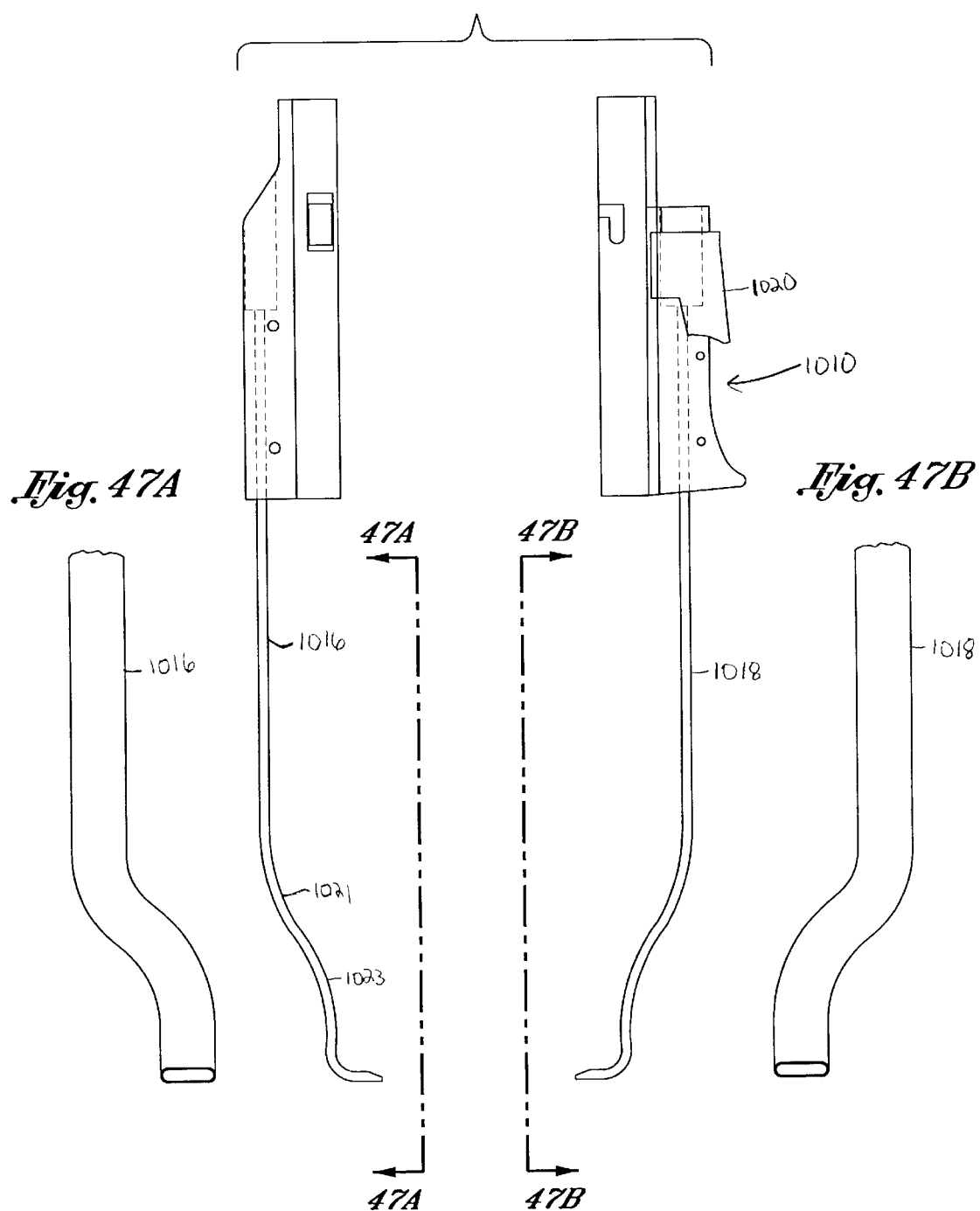
FIG. 47 is a side view of an alternate embodiment of the sling application device in which the shafts have a side bend.

FIGS. 47, 47A and 47B show a sling application device 1010 in which the shafts have a side bend. In this embodiment, the first shaft 1016 is flat and has a first curved section 1021 and a second curved 1023 section along its length. Preferably, the portion maximum offset between the first curved section 1021 and the second curved section 1023 is from about 1 inch to about 3 inches. As shown in FIGS. 47 and 47B, the second shaft 1018 has the same structure as the first shaft 1016. Preferably, the first and second shafts 1016, 1018 undergo a smooth transition from cylindrical to elliptical or flat. More preferably, the portion of the shaft proximal to the first curved section 1021 is cylindrical and the portion of the shaft distal to the first curved section is flat. Preferably, the radius of curvature of the second curve is not planar with the axial plane of the portion of the shaft. The adjuster 1020 in this embodiment may be the same as the adjuster described above.

Figure 48:
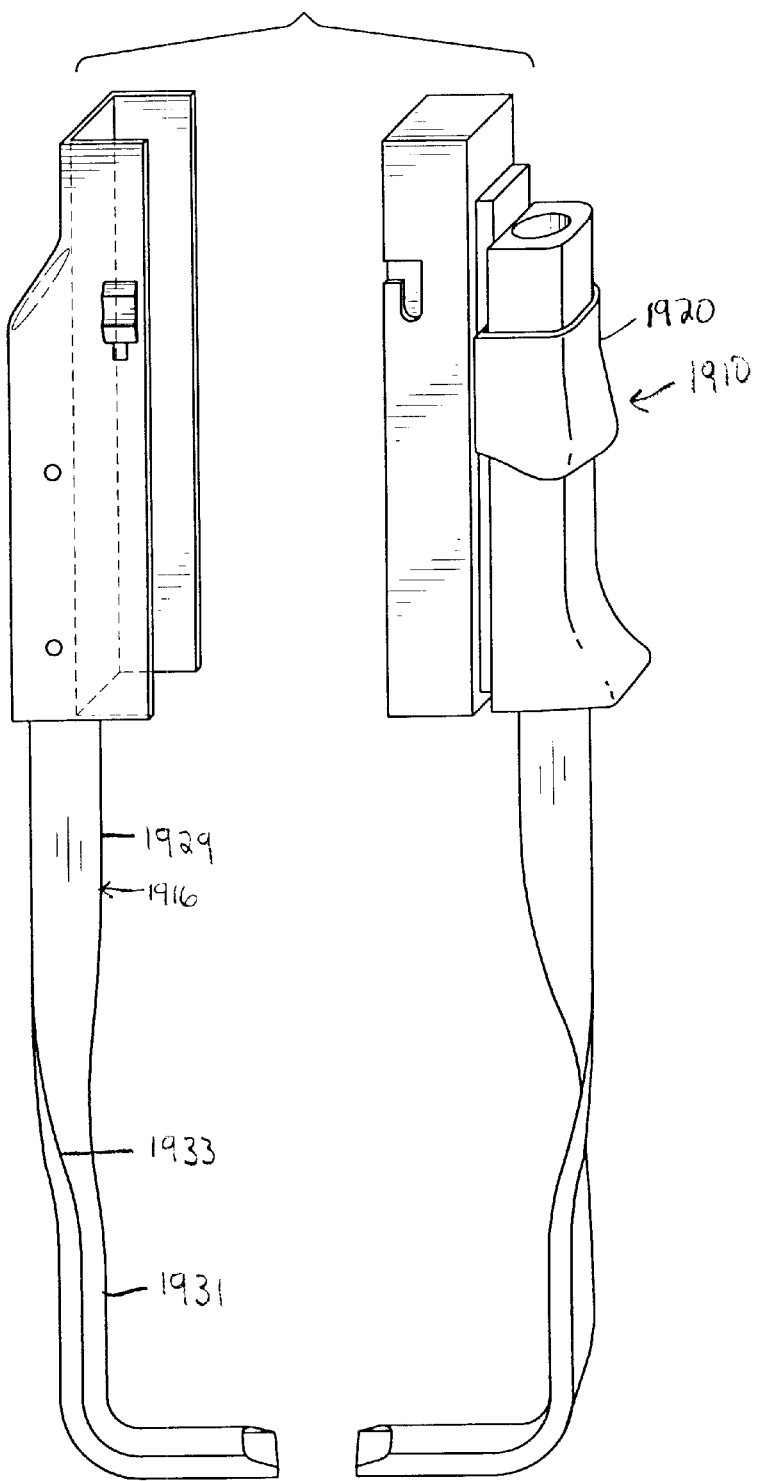
FIG. 48 is a side view of a sling application device in which the shafts have a 90° twist.

Alternatively, the shaft may have a 90° twist as shown in FIG. 48. In this embodiment of the sling application device 1910, the proximal portion 1929 of the first shaft 1916 is oriented at an angle of 90° relative to the distal portion 1931 of the first shaft, with a transitional section 1933 disposed between the proximal section of the first shaft 1929 and the distal section of the first shaft 1931. The adjuster 1920 in this embodiment may be the same as the adjuster described above.

Figure 56:
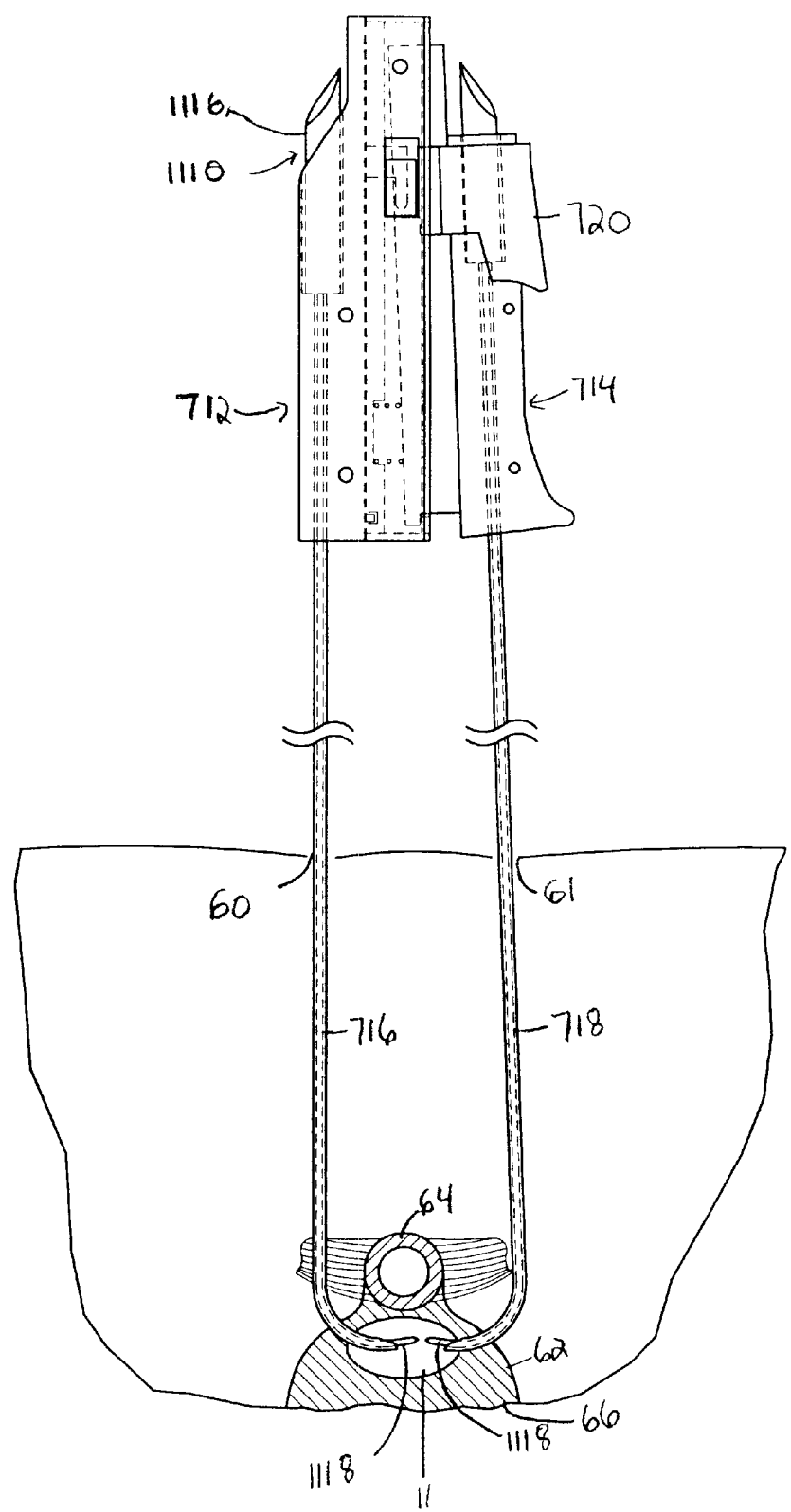
FIG. 56 shows the first and second handles of the sling application device locked together.
Figure 57:
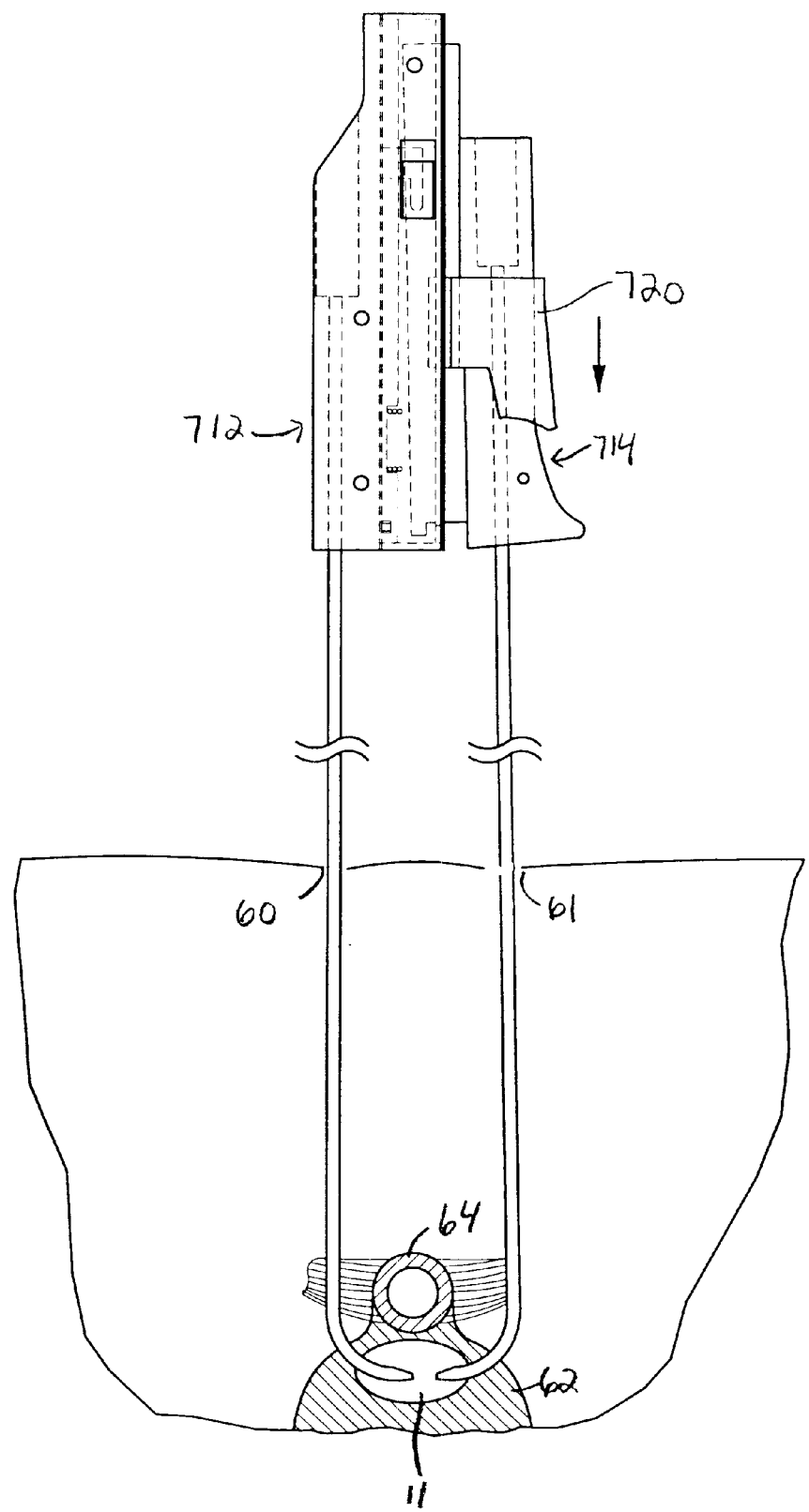
FIG. 57 shows the distance between the distal ends of the first and second shafts of the sling application device being decreased as the adjuster is advanced to a position in between the proximal point and the distal point of the guide.
Figure 58:
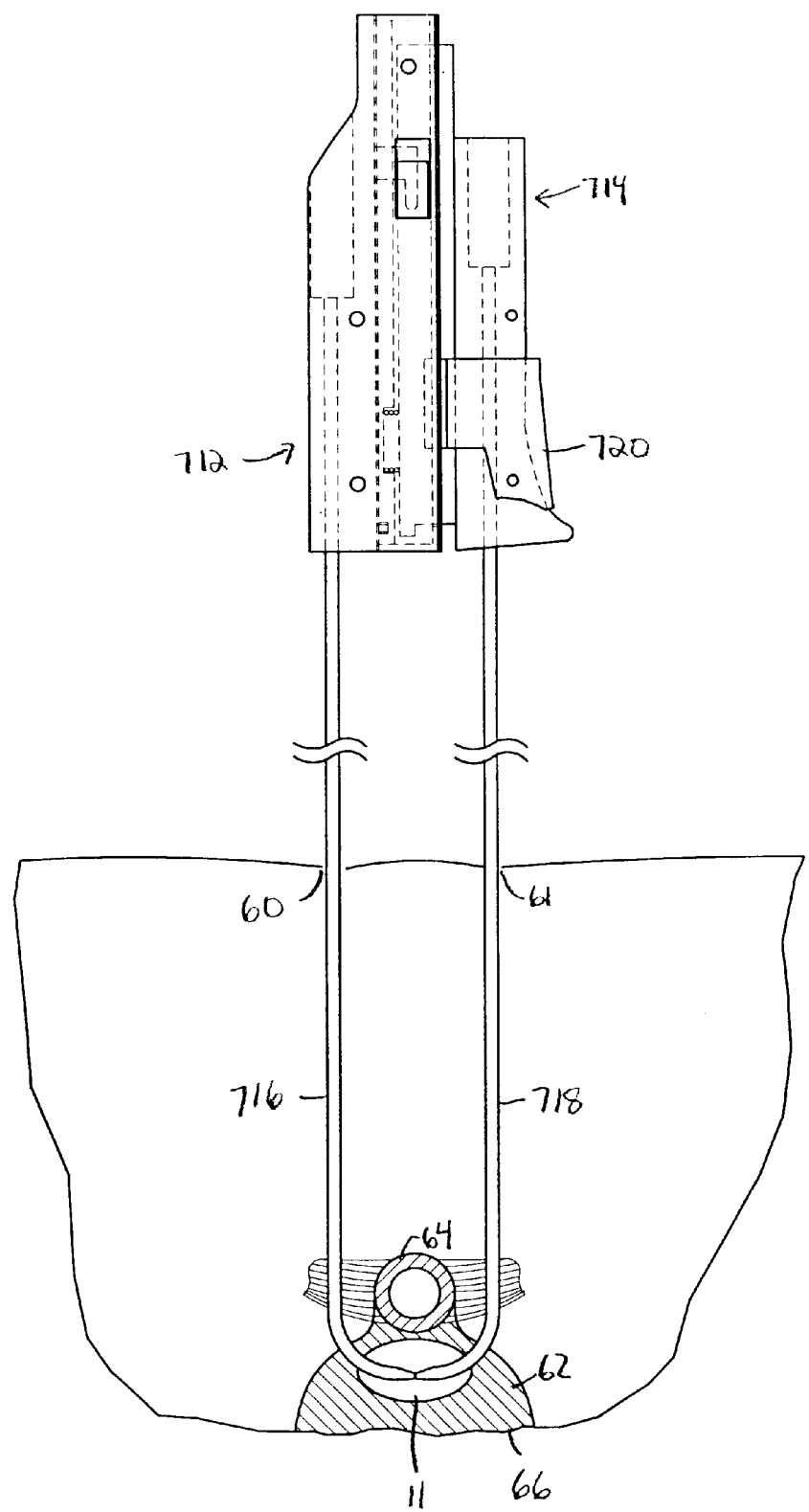
FIG. 58 shows the tissue between the distal ends of the first and second shafts of the sling application device being compressed when the adjuster is advanced to the distal end of the guide.

Referring to FIG. 38A, one face 746 of the second handle is adapted to enable the physician to firmly grasp it when advancing the device through tissue. An adjuster 720 is slidably mounted on face 746. The adjuster 720 slidably engages a guide 748 on the bottom of the first handle 712. The guide 748 is hingedly connected to the extension 730 and is biased away from the extension 730 by a biasing means such as a spring 754 (indicated in FIG. 56) disposed between the guide 748 and the extension 730. Tabs 750 on the adjuster 720 fit into grooves 752 between the sides of the extension 730 and the sides of the guide 748 such that the adjuster 720 moves along the guide 748 between a proximal end and a distal end. When the two handles have been locked together, moving the adjuster 720 along the guide 748 adjusts the distance between the distal ends of the first and second shafts 716, 718 as depicted in FIGS. 56–58, which are discussed in greater detail below. However, those skilled in the art will appreciate that there are other adjuster designs compatible with the operation of the present device, and such designs are specifically contemplated in the present invention.

As the adjuster 720 is moved towards the distal extreme of the guide 748, the resistance of the spring biasing the guide away from the extension 730 is overcome and the distance between the distal ends of the first and second shafts 716, 718 decreases. As the adjuster 720 is moved towards the proximal extreme of the guide 748, the spring pushes the guide 748 away from the extension 730 and the distance between the distal ends of the first and second shafts 716, 718 increases.

The second handle 714 has a second shaft 718 extending therethrough. The second shaft 718 may have the same configurations and be made of the same materials as described above with regard to the first shaft 716. Preferably, the second shaft of the second handle has the same configuration as the first shaft of the first handle with which it is to be used, as illustrated in FIGS. 38–48.

Figure 49:
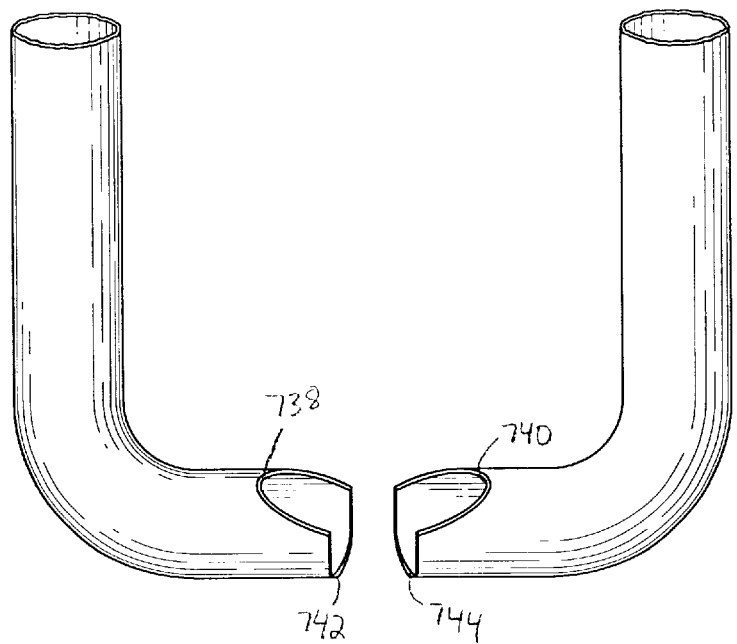
FIG. 49 is a perspective view of the distal ends of the first and second shafts of a sling application device in which the upper edges of the distal ends of the shafts are slightly indented relative to the lower edges.

Preferably, as shown in FIG. 49, the upper edges 738 and 740 of the distal ends of the first and second shafts 736, 715 are slightly indented relative to the lower edges 742 and 744 to reduce the possibility of the urethra being pinched during the sling implantation procedure.

A further aspect of the present invention is a blunt dissector for dissecting the body tissue without scoring or creasing the tissue or bone with which it comes in contact. The blunt dissector is adapted for insertion into the first and second shafts of the sling application device and protrudes from the distal ends of the shafts. The blunt dissector can be used as a component in the sling application system.

Figure 50:
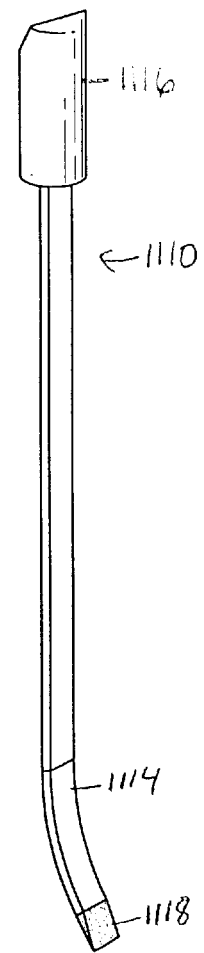
FIG. 50 is a side view of an obturator for use with the sling application device.

The blunt dissector may be an obturator 1110 as shown in FIG. 50. The obturator comprises an elongate, flat shaft 1112 interposed between a flexible section 1114 located at the distal end of the shaft and a handle 1116 located at the proximal end of the shaft 1112. When the obturator 1110 is inserted into the first and second shafts 716 and 718 of the sling application device, the flexible section 1114 bends to permit the obturator 1110 to conform to the curves near the distal ends of the shafts 716 and 718. The flexible section 1114 has a generally rigid tip 1118 at its distal end which extends from the distal ends of the first and second shafts 716 and 718 when the obturator 1110 is inserted therein. The generally rigid tip 1118 prevents scoring of the tissue or bone with which it comes in contact when the first and second shafts 716, 718 are advanced through tissue. In an alternate embodiment, the flexible section may have an opening near its distal end to increase flexibility.

The shaft 1112 of the obturator may be made of a variety of materials such as polycarbonate, nylon, polypropylene, and Acrylonitrile Butadiene Styrene (ABS). A preferred material is ABS.

The flexible section 1114 of the obturator may be made of any of a number of materials, including polycarbonate, nylon, polypropylene, and ABS. Preferably, the flexible section 1114 is made of ABS.

The generally rigid tip 1118 of the obturator may be made of materials such as polycarbonate, nylon, polypropylene, and ABS. Preferably, the generally rigid tip 1118 is made of ABS.

When the obturator 1110 is inserted into the first and second shafts 716, 718, the generally rigid tip of the obturator 1118 protrudes from the distal ends of the shafts 716, 718. Preferably, the generally rigid tip 1118 protrudes a distance of from about 0.1 inch to about 0.25 inch from the lower edges 742, 744 of the distal end of the shafts 716, 718. More preferably, the generally rigid tip 1118 protrudes a distance of about 0.20 inch from the lower edges 742, 744 of the distal end of the shafts 716, 718.

Yet another aspect of the present invention is a sling introducer 1210 adapted for releasably engaging a sling 1211 and introducing the sling 1211 into the body tissue without the use of sutures. The sling introducer 1210 can be used as a component in the sling application system and is adapted for insertion into and advancement through the first and second shafts 716, 718 of the sling application device 710. Alternatively, the sling introducer can be used in conjunction with laparoscopic trocars.

Figure 51:
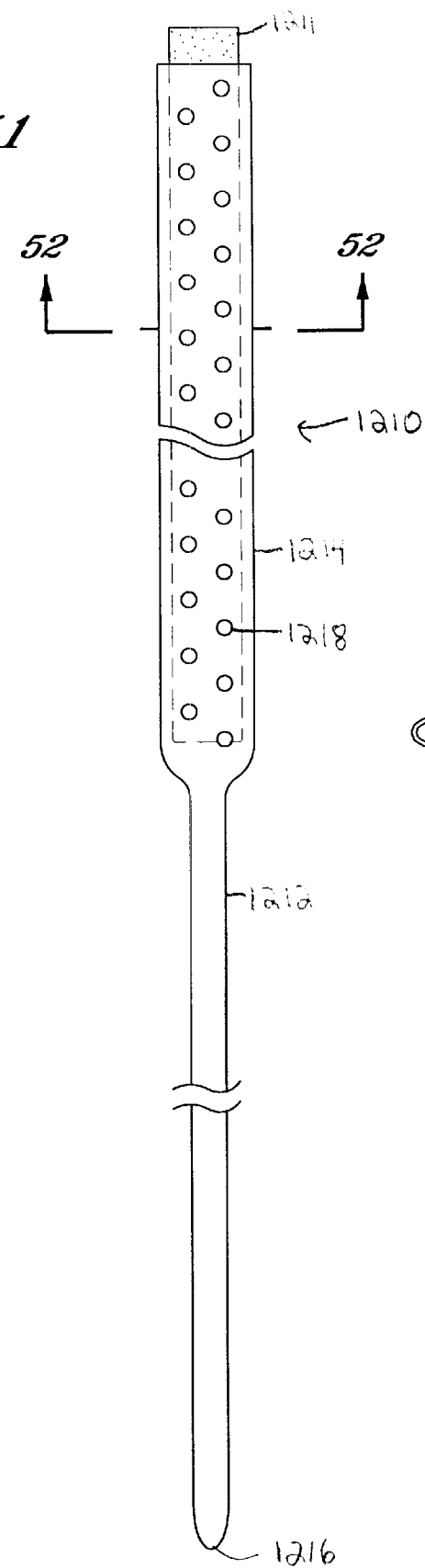
FIG. 51 is a plan-view of a sling introducer.
Figure 52:
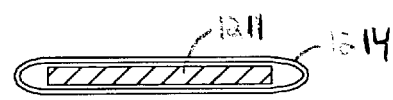
FIG. 52 is a cross-sectional view taken along line 52—52 of the sling introducer of FIG. 51.

A representative sling introducer 1210 is shown in FIGS. 51 and 52. The sling introducer 1210 can be made of any of a number of materials such as polyethylene, PET or vinyl. Preferably, the sling introducer 1210 is made of generally rigid vinyl.

The sling introducer 1210 of FIG. 51 has a narrow elongate distal tip 1212 and a pouch 1214 at the proximal end. The elongate distal tip 1212 of the sling introducer of the sling introducer is configured to pass through the first and second shafts 716, 178 of the sling application device. The sling introducer 1210 is sufficiently long to permit the distal tip 1216 of the sling introducer to protrude from the proximal end of the opening 725 in the first handle of the sling application device 710 while the sling 1211 protrudes from the proximal end of the opening 727 in the second handle of the sling application device 710.

The pouch 1214 of the sling introducer is sized to receive a sling 1211 therein. The slings 1211 introduced with the sling introducer 1210 can be long enough to extend between two suprapubic incisions or may be shorter slings designed to be attached to the pubic bone with sutures. Long and short slings suitable for use with the present invention are disclosed in the copending U.S. patent application entitled "Stabilization Sling for Use in Minimally Invasive Pelvic Surgery" (VESITEC.023A), filed simultaneously herewith, and the identically titled U.S. Provisional Patent Application Serial No. 60/038,379, filed Feb. 13, 1997, the disclosures of which are incorporated herein by reference.

The pouch 1214 is relatively flexible, and is preferably made of a soft, pliable plastic such as polyethylene, PET or vinyl. In some embodiments, the pouch 1214 may be reinforced by a stiffener to provide some rigidity along the edges as discussed above. The proximal end of the pouch 1214 may be sufficiently wide to maintain the sling 1211 in a flat orientation. Alternatively, the pouch of the sling introducer 1210 may be rolled up such that the sling is also in a rolled configuration. During introduction of the sling into the opening or pocket in the body tissue, the sling 1211 may be converted to a flat configuration.

In one embodiment, the pouch 1214 has pores 1218 therein as shown in FIG. 51 to facilitate re-hydration or soaking treatments of the sling materials. In particular, the porous pouch 1214 permits solutions in which the pouch is placed to contact the sling inside the pouch. Such solutions include saline solutions and antibiotic solutions. In this way, the pores facilitate treatments in which the sling is soaked in antibiotics to prevent the growth of microorganisms on the surface of the sling after the sling 1211 is introduced into the body. The pores also permit gas sterilization of the sling while it is inside the pouch.

In this embodiment, the pouch 1214 may be made of a variety of materials, such as PE, PET, or vinyl. Preferably, the pouch is made of clear material to permit visualization of the sling when it is inside the pouch. Preferably, the pouch has pore sizes from about 0.10 inch to about 0.25 inch. Preferably, the pouch 1214 is made of vinyl having a pore size of about 0.125 inch.

In alternate embodiments, the pouch 1214 may be non-porous. Such pouches may be made of the same materials as described above for the porous pouches. However, the nonporous pouches do not have pores formed therein.

Figure 53:
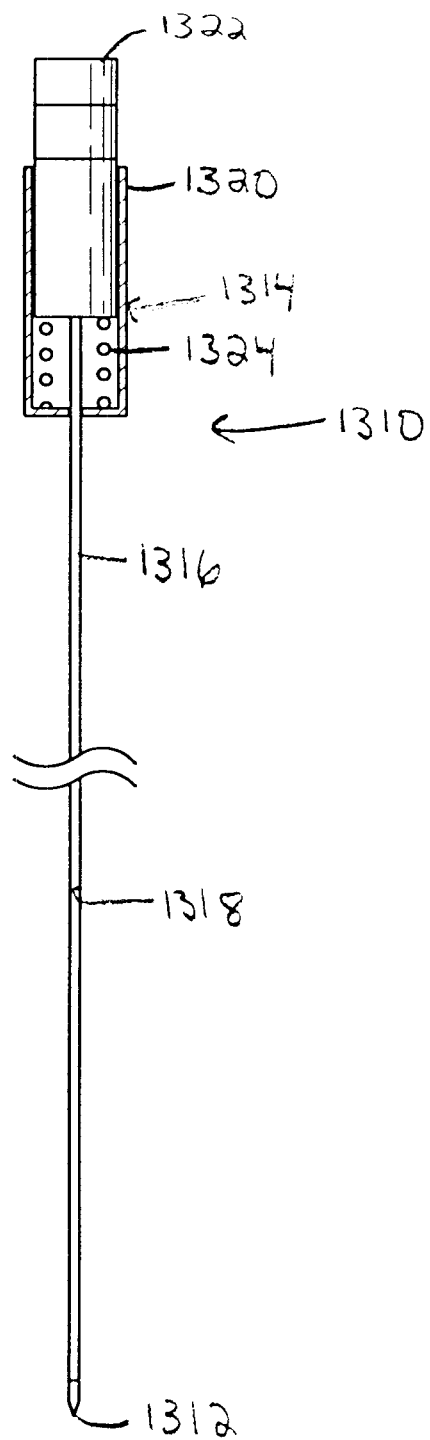
FIG. 53 is a cross-sectional view of a cutter showing the internal structure of the device.

Yet another aspect of the present invention is a tissue cutter 1310, 1312 for cutting tissue disposed between the distal ends of the first shaft and the second shaft. As shown in FIG. 53, the tissue cutter 1310 comprises a razor 1312 housed in a razor assembly 1314. A flexible catheter 1316 extends from the distal portion of the razor assembly 1314. A lumen 1318 extends through the catheter 1316. The width of catheter 1316 of the tissue cutter is slightly smaller than the width of the second shaft 718 of the sling application device 710, such that the catheter 1316 can be inserted inside the second shaft 718. The tissue cutter 1310 can be used as a component of the sling application system.

In the tissue cutter shown in FIG. 53, the razor assembly 1314 comprises a handle 1320 having a thumb button 1322 at its proximal end and an elongate catheter 1316 adapted to receive the razor 1312 therein. The thumb button 1322 is movable between a proximal position and a distal position and is biased towards the proximal position by a spring 1324 inside the handle. When the thumb button 1322 is depressed, the resistance of the spring 1324 is overcome, and the thumb button 1322 engages the razor 1312, moving the razor 1312 to a position in which it protrudes from the distal end of the catheter 1316. When the thumb button 1322 is released, the razor retracts inside the catheter.

The razor 1312 is slightly smaller in width than the lumen of the catheter 1316. The width of the razor 1312 is generally the same as the desired width of the sling 1211 which will be inserted according to the procedure described below. In addition, as shown in FIG. 53, the razor 1312 is slightly tapered at its distal end.

Although several embodiments of the sling application device and the components of the sling application system have been described above, those skilled in the art will appreciate that other configurations are compatible with the operation of the device and the system. For example, a spring biased trigger on the first handle of the sling application device may substitute for the articulating lock for adjusting the distance between the distal ends of the first and second shafts. Such additional configurations are also contemplated by the present invention.

The sling application device is used as follows. The method is performed with the patient in the dorsal lithotomy position. In some methods a pocket or opening 11 is created in the tissue between the urethra and the upper vaginal wall using any of the methods and devices disclosed herein. In such methods, the first and second shafts 716 and 718 maintain the opening or pocket in a configuration in which the sling can be introduced.

Alternatively, the sling application device can be used to create the opening or pocket 11 in the tissue between the urethra and the upper vaginal wall.

Both the methods in which the sling application device maintains the opening or pocket and the methods in which the sling application device creates the opening or pocket are described below.

Each of the above described embodiments of the sling application device can be used according to the method described below and shown in FIGS. 54–65.

Figure 54:
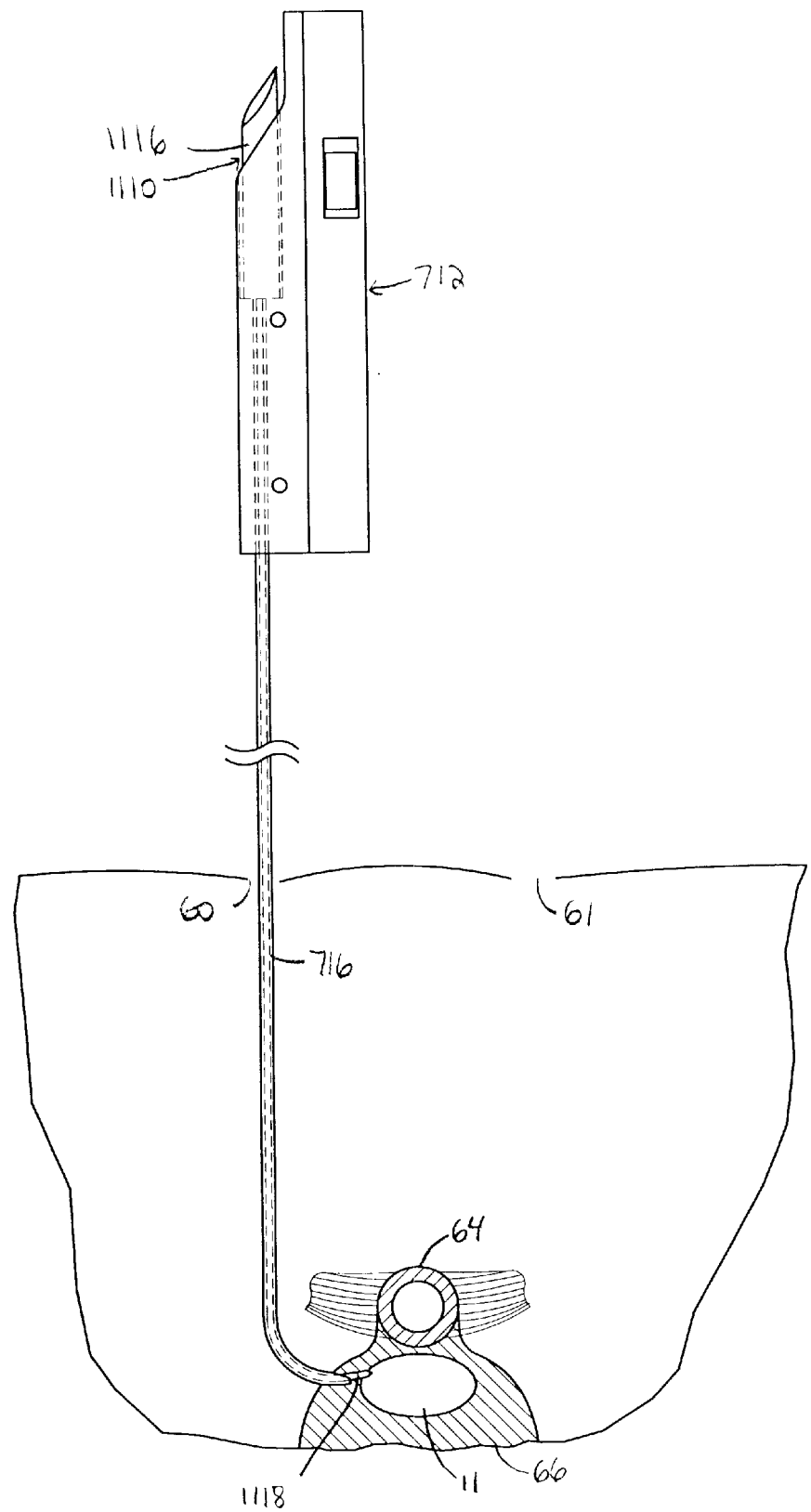
FIG. 54 shows the first shaft of the sling application device being advanced into a pre-formed opening in the tissue between the urethra and the upper vaginal wall.

After inserting an obturator 1110 into the lumen 711 of the first shaft such that the generally rigid tip 1118 extends from the distal end of the first shaft, the first shaft 716 is inserted percutaneously. For example, the first shaft 716 may be inserted into a first suprapubic incision 60, which is preferably approximately 1 to 1.5 inches in length, and is located above a pubic tubercle. The first shaft 716 is advanced into the patient's body and guided along the back side of the pubic bone to the upper vaginal wall. Once the vaginal wall is tented, placement is visually realized and lateral placement can then be adjusted. As shown in FIG. 54, the sling application device is then rotated 90° such that the distal end of the first shaft 716 is directed perpendicular to the urethra 64 facing the tissue 62 between the urethra 64 and the upper vaginal wall 66, creating and/or maintaining an opening or pocket in the tissue between the urethra and the upper vaginal wall. With the embodiments shown in FIGS. 47 and 48, the sling application device will rotate 90° as the device passes along the back of the pubic bone.

Figure 55:
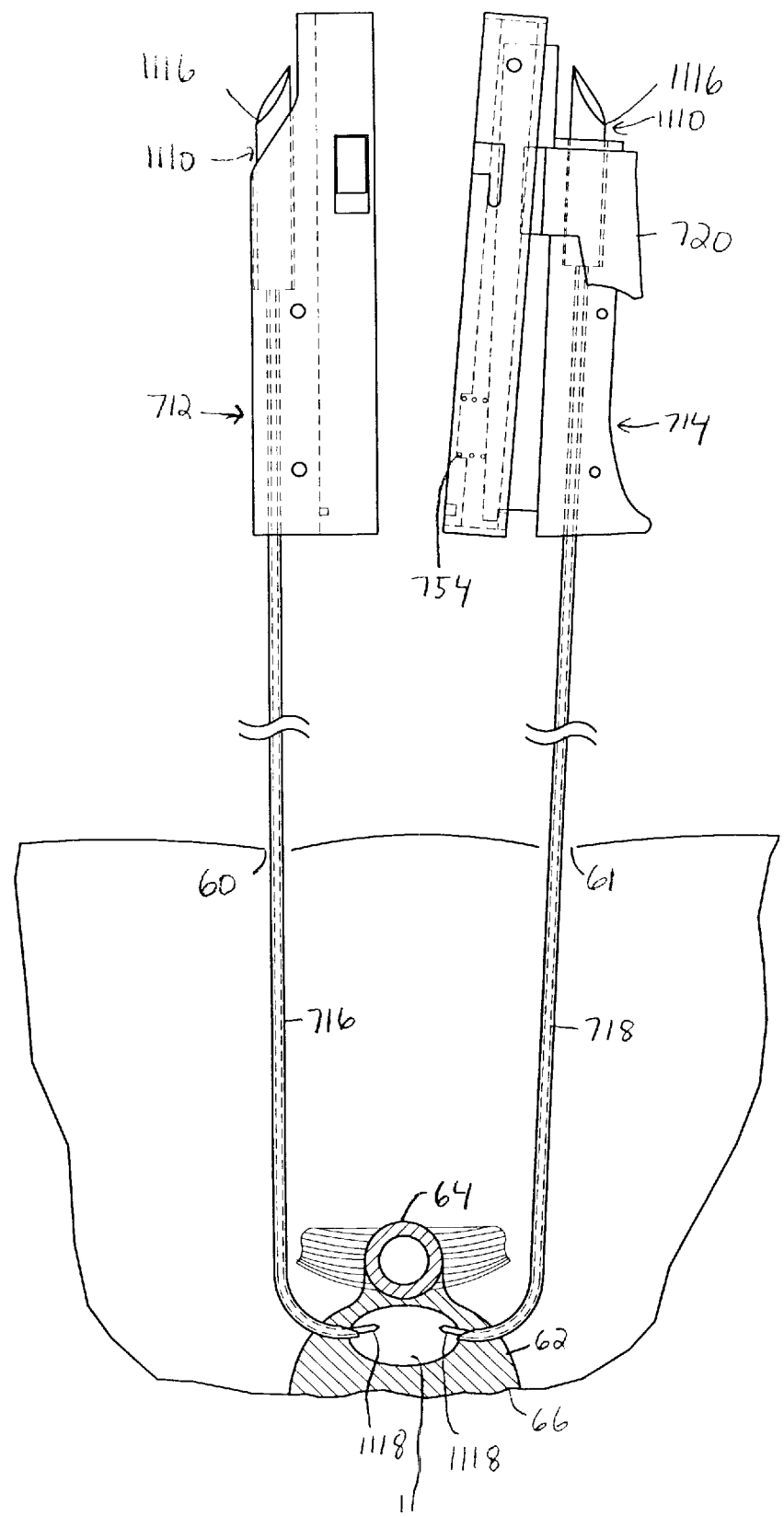
FIG. 55 shows the distal ends of the first and second shafts of the sling application device opposing each other in the opening in tissue between the urethra and the upper vaginal wall.

After inserting an obturator 1110 into the lumen 713 of the second shaft such that the generally rigid tip 1118 extends from the distal end of the second shaft 718, the second shaft 718 is inserted percutaneously. For example, the second shaft may be inserted into a second suprapubic incision 60, which is preferably approximately 1 to 1.5 inches in length, and is located above a pubic tubercle. The second shaft 718 is advanced into position as described above such that the distal end of the second shaft 718 is perpendicular to the urethra 64 facing the tissue 62 between the urethra 64 and the upper vaginal wall 66, thereby creating and/or maintaining an opening in the tissue between the urethra and the upper vaginal wall. As shown in FIG. 55, at the completion of this step, the distal ends of the first and second shafts 716, 718 oppose each other in the tissue 62 between the urethra 64 and the upper vaginal wall 66.

After the sling application device is in position, the obturators 1110 are removed from the first and second shafts 716, 718 and the first 712 and second 714 handles are locked together with the adjuster 720 at its most proximal point, as shown in FIG. 56. The adjuster 720 is advanced towards the distal extreme of the guide 748, progressively decreasing the distance between the distal ends of the first and second shafts 716, 718 as shown in FIGS. 57 and 58. During this process, the physician may observe the inner wall surface of the urethra 64 with a cystoscope to avoid pinching the urethra. The physician also observes the upper vaginal wall 66 to avoid pinching. When the first and second shafts 716, 718 have been properly positioned, no pinching is observed at either the inner wall of the urethra or the upper vaginal wall. Correct placement is confirmed through touch and by visualizing a bulge in the upper vaginal wall at the desired positions.

Once correct placement has been obtained, the adjuster 720 is advanced to the distal extreme of the guide 748, compressing the tissue 62 between the distal ends of the first and second shafts 716, 718, as shown in FIG. 58.

Figure 59:
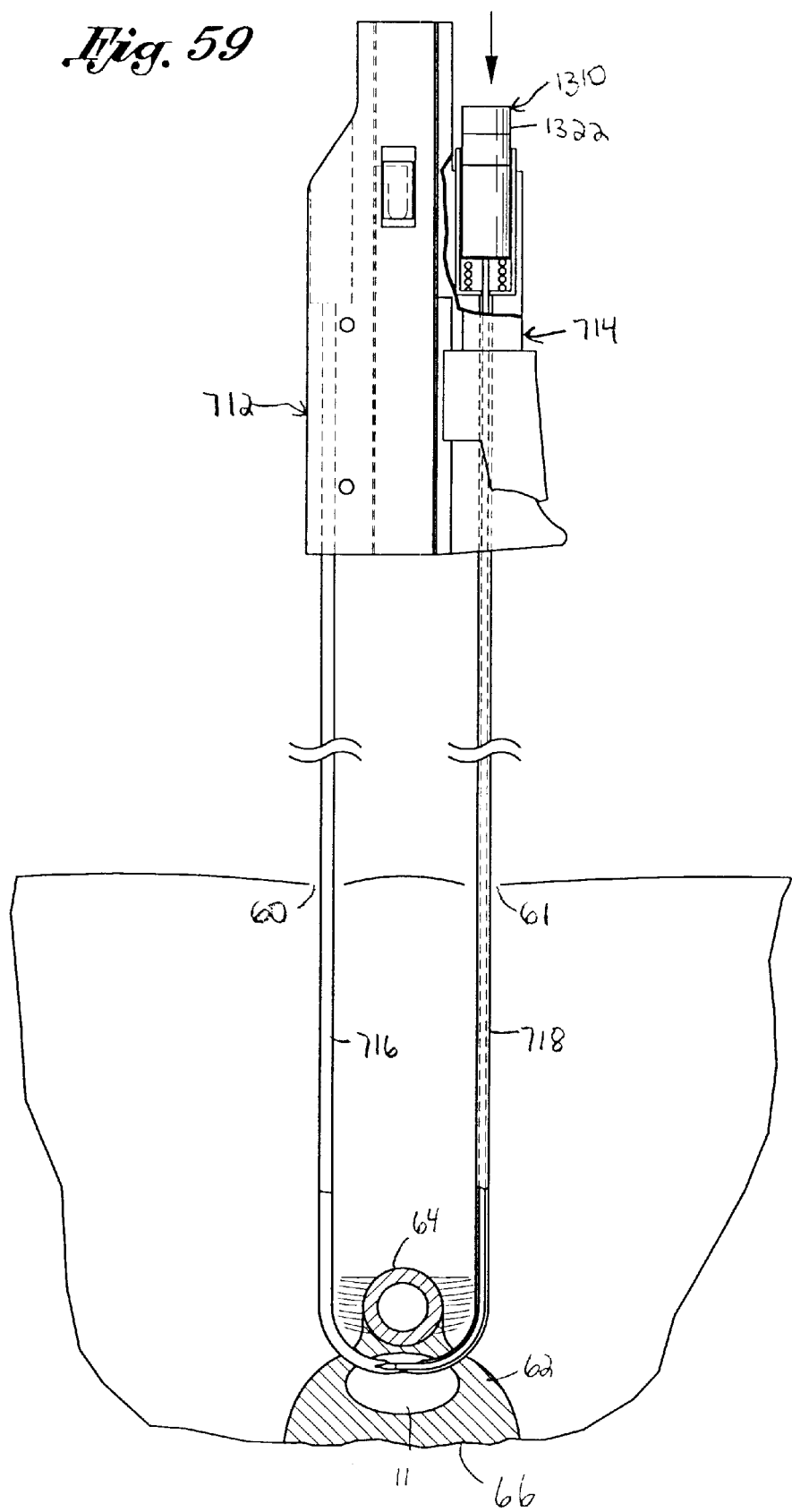
FIG. 59 shows an opening in the tissue between the urethra and the upper vaginal wall being created by a cutter dissecting the tissue between the distal ends of the first and second shafts of the sling application device.

In the methods in which the sling application device 710 creates the pocket or opening in the tissue between the urethra and the upper vaginal wall, the tissue cutter 1310 is then inserted into the second shaft 718 as shown in FIG. 59. When the thumb button 1322 of the razor assembly 1314 is depressed, the razor 1312 extends out of the distal end of the second shaft 718 and cuts the tissue 62 disposed between the distal ends of the first and second shafts 716, 718, creating a continuous opening 11 or pocket sized to receive the sling. The thumb button 1322 of the razor assembly 1314 is then released, causing the razor 1312 to retract within the second shaft 718. The razor assembly 1314 is then removed from the second shaft 718.

Figure 60:
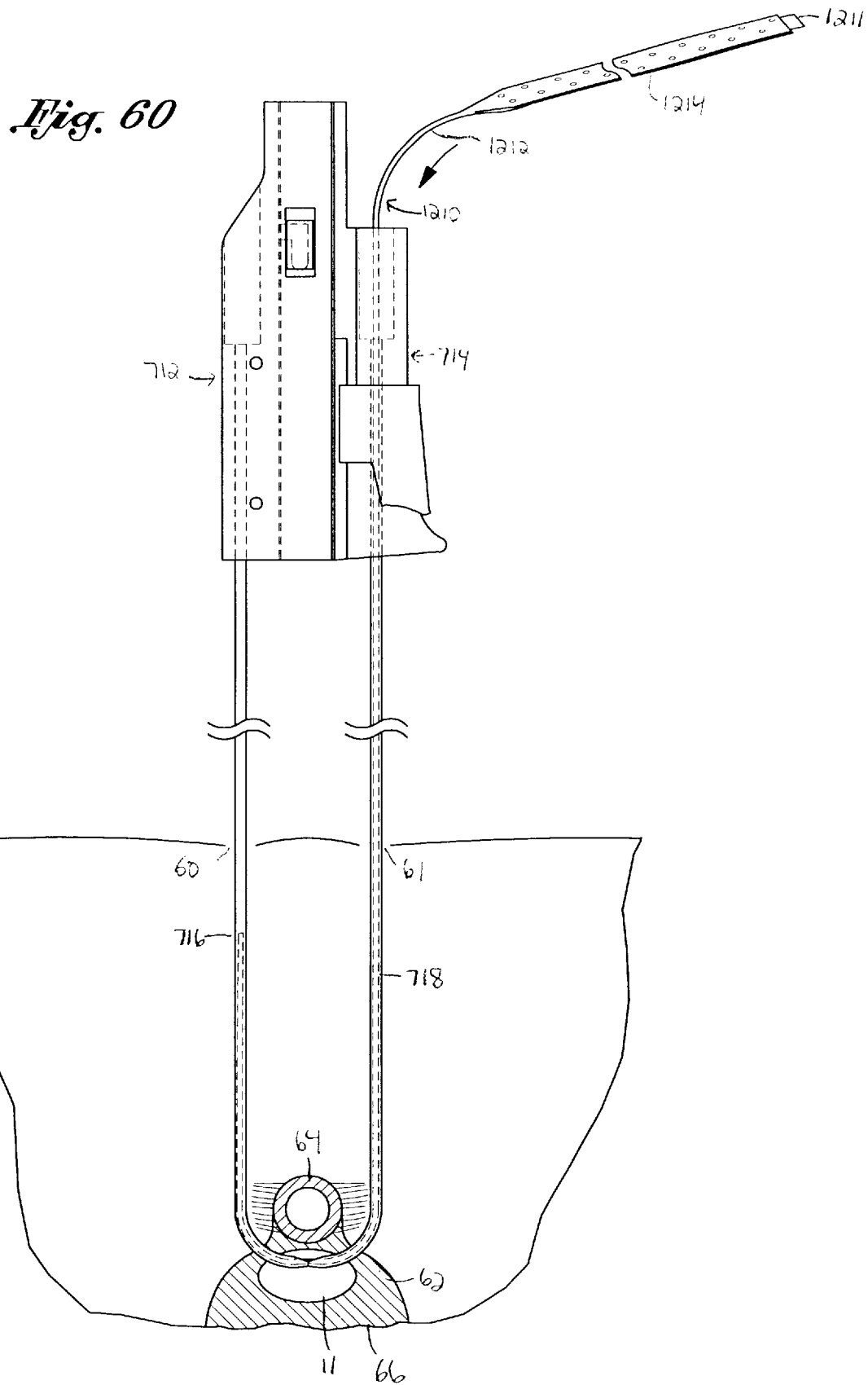
FIG. 60 shows the sling introducer being inserted into the second shaft of the sling application device.

In both the methods in which the sling application device maintains the pocket or opening and the methods in which the sling application device creates the pocket or opening, a sling or a sling introducer 1210 having a releasably engaged sling 1211 attached thereto is inserted through the opening 727 of the second handle and into the lumen of the second shaft 718, as shown in FIG. 60. The proximal end of the sling 1211 extends beyond the proximal end of the sling introducer 1210. Long and short slings suitable for use with the present invention are disclosed in the copending U.S. patent application entitled "Stabilization Sling for Use in Minimally Invasive Pelvic Surgery" (VESITEC.023A), filed simultaneously herewith, and the identically titled U.S. Provisional Patent Application Serial No. 60/038,379, filed Feb. 13, 1997, the disclosures of which are incorporated herein by reference.

Preferably, a porous sling introducer 1210 is used and the porous sling introducer 1210 with the sling 1211 attached thereto is soaked in a wetting and/or antibiotic solution as described above prior to insertion into the first shaft.

Figure 61:
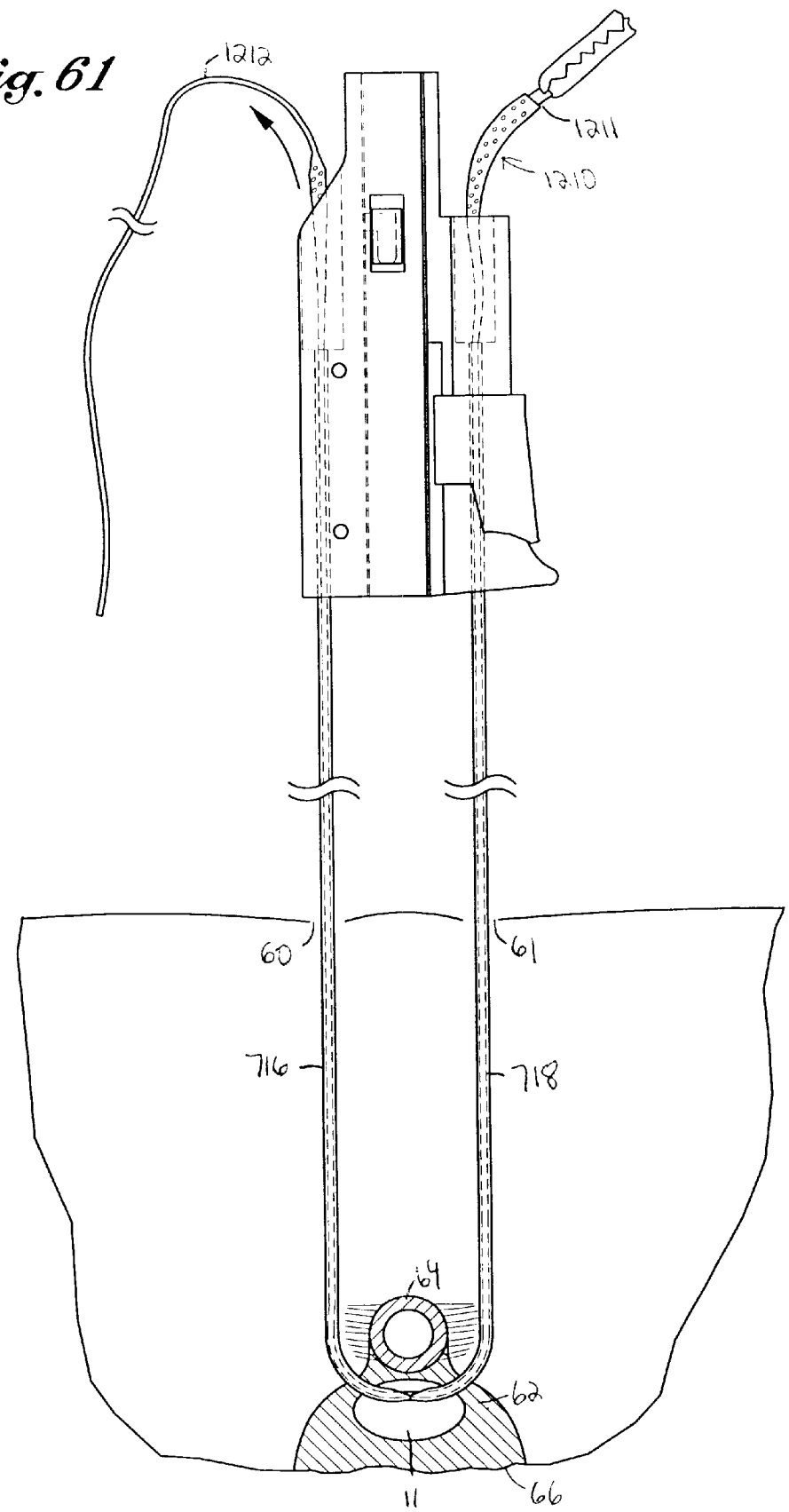
FIG. 61 shows the sling being withdrawn from the sling introducer as the sling introducer is advanced through the tissue between the urethra and the upper vaginal wall.
Figure 62:
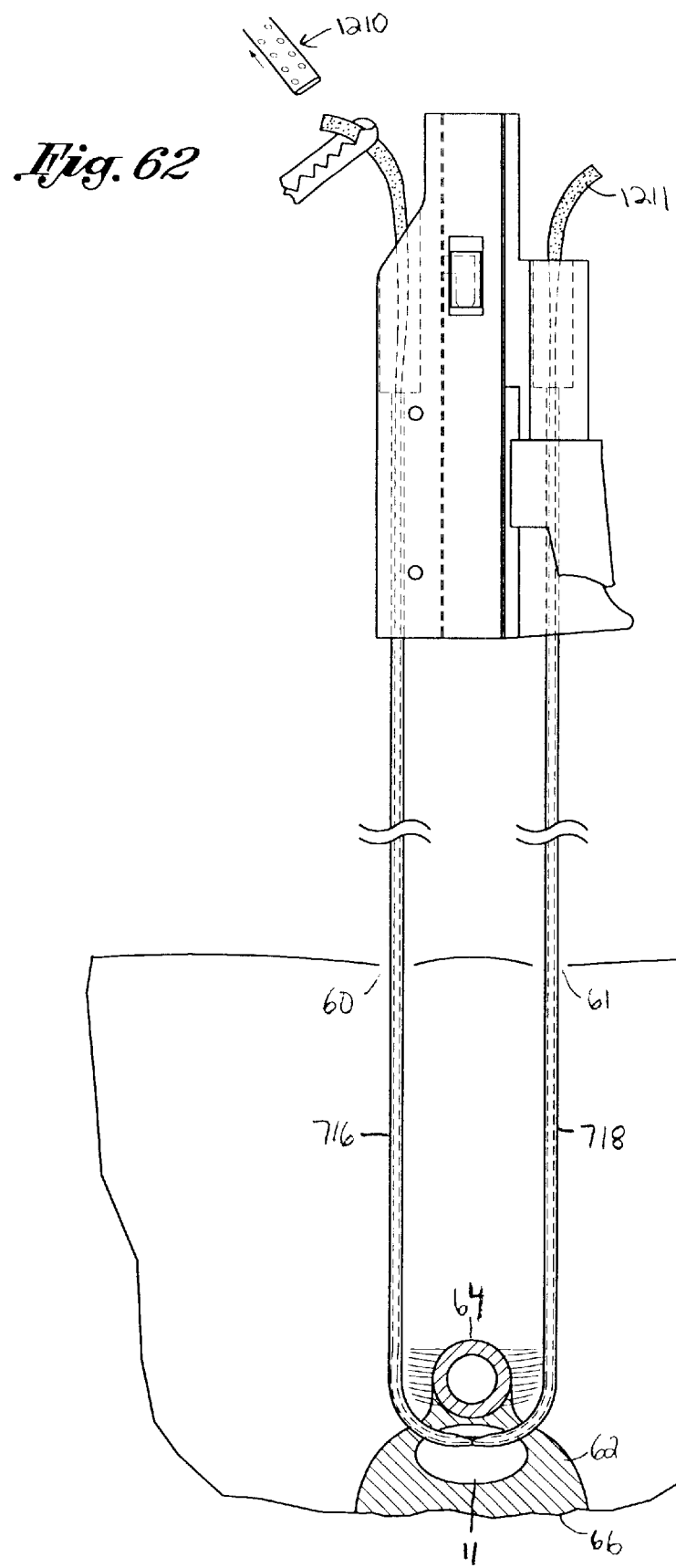
FIG. 62 shows the sling fully withdrawn from the sling introducer and located within the first and second shafts of the sling application device.
Figure 63:
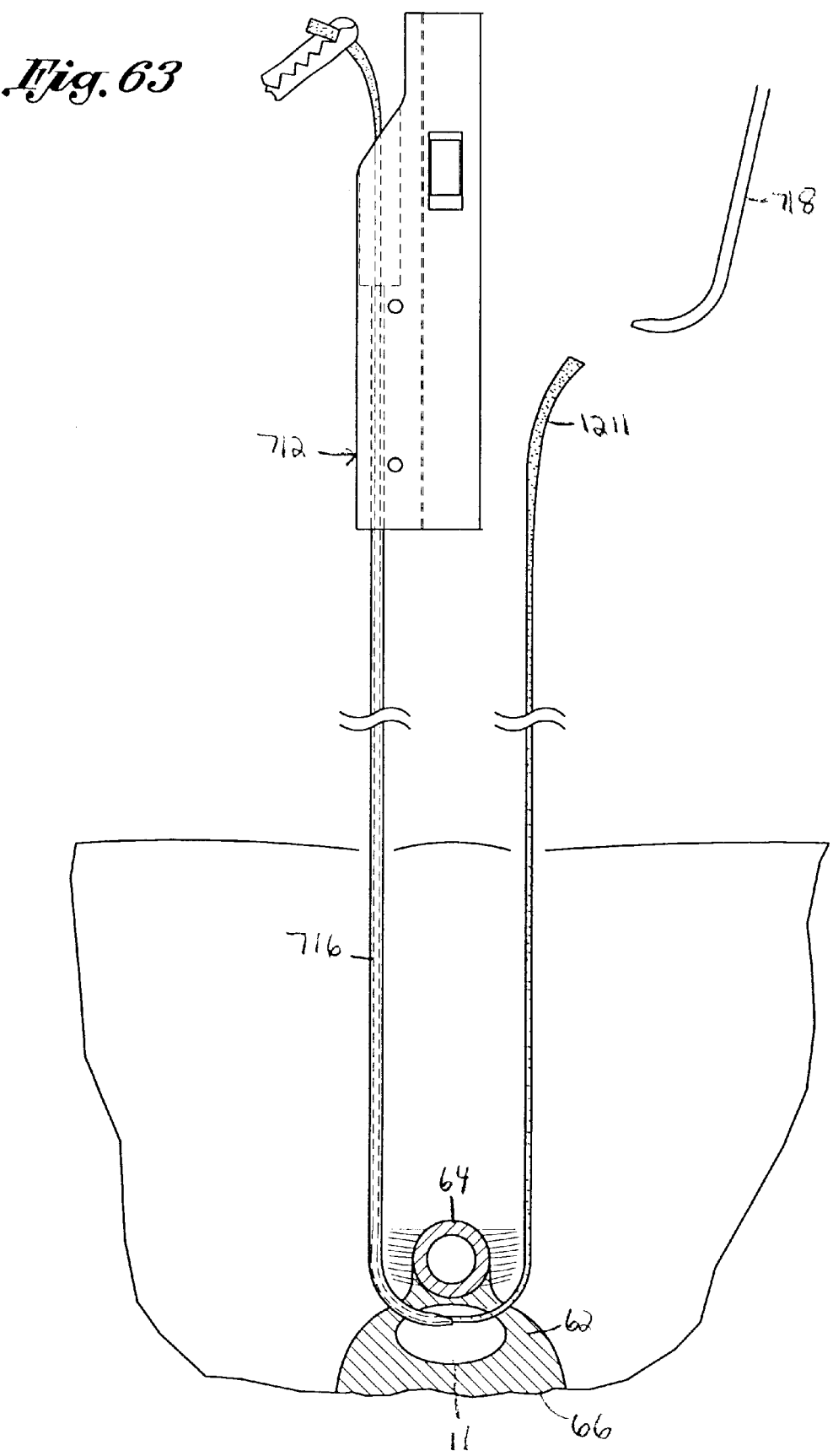
FIG. 63 shows the second shaft of the sling application device being removed from the patient's body.

The elongate distal end 1212 of the sling introducer is advanced through the opening 727 in the second handle, into the lumen of the second shaft 718, into the lumen of first shaft 716, and out the opening 725 in the first handle as shown in FIG. 61. While holding the proximal end of the sling 1211, the elongate distal end 1212 of the sling introducer 1210 is pulled. The sling introducer 1210 is advanced until it exits the opening in the first handle 725, leaving the sling 1211 within the first and second shafts 716, 718, as shown in FIG. 62. Following this step, the sling 1211 is located within the first 716 and second 718 shafts and extends out of the proximal ends of the openings 725, 727 in the first and second handles. As shown in FIG. 63, the end of the sling 1211 extending out of the proximal end of the opening in the first handle is grasped and the second shaft 718 is removed from the patient's body, leaving the sling 1212 in the opening 11 in the tissue which was formerly occupied by the second shaft.

Figure 64:
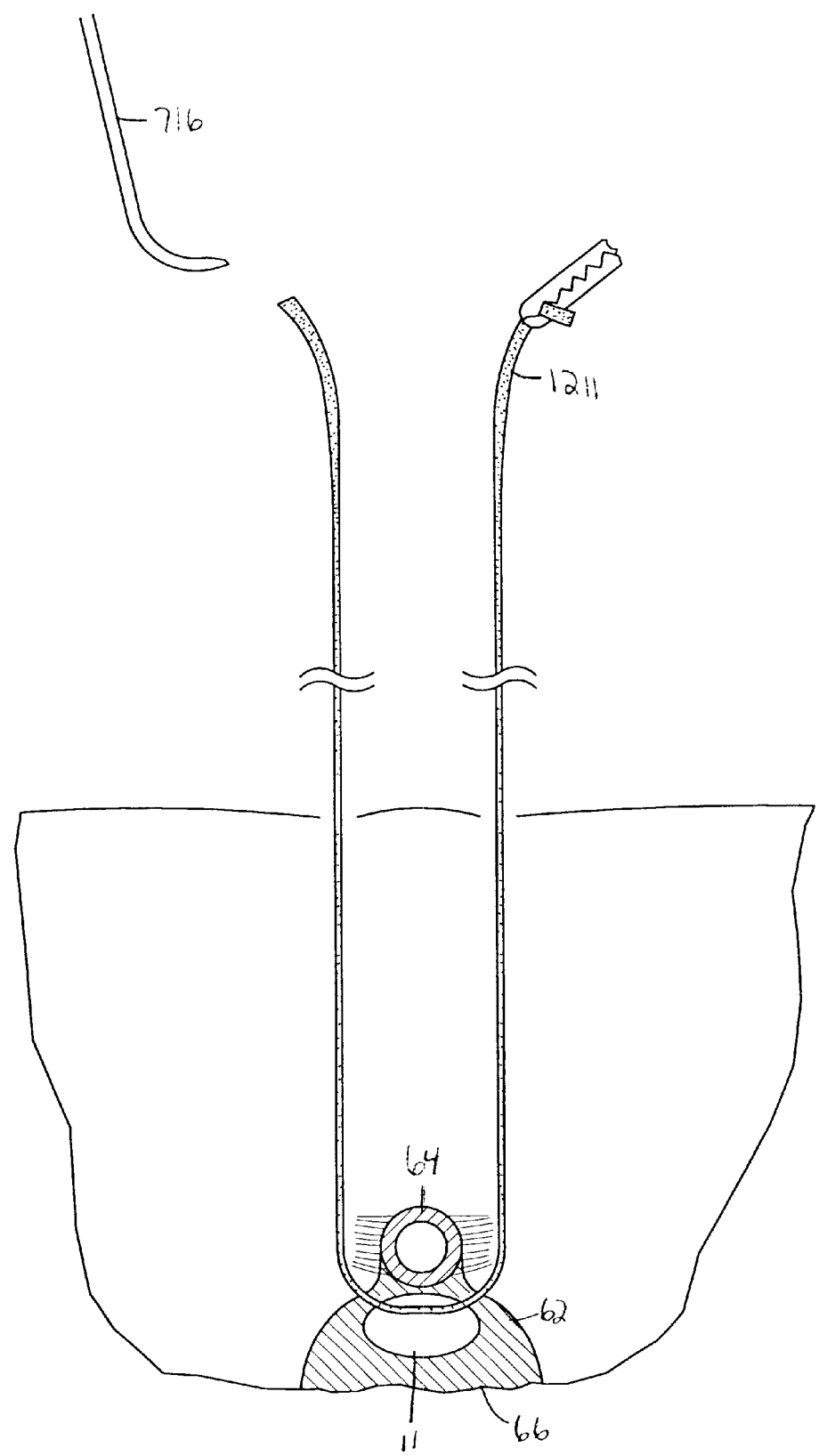
FIG. 64 shows the first shaft of the sling application device being removed from the patient's body.
Figure 65:
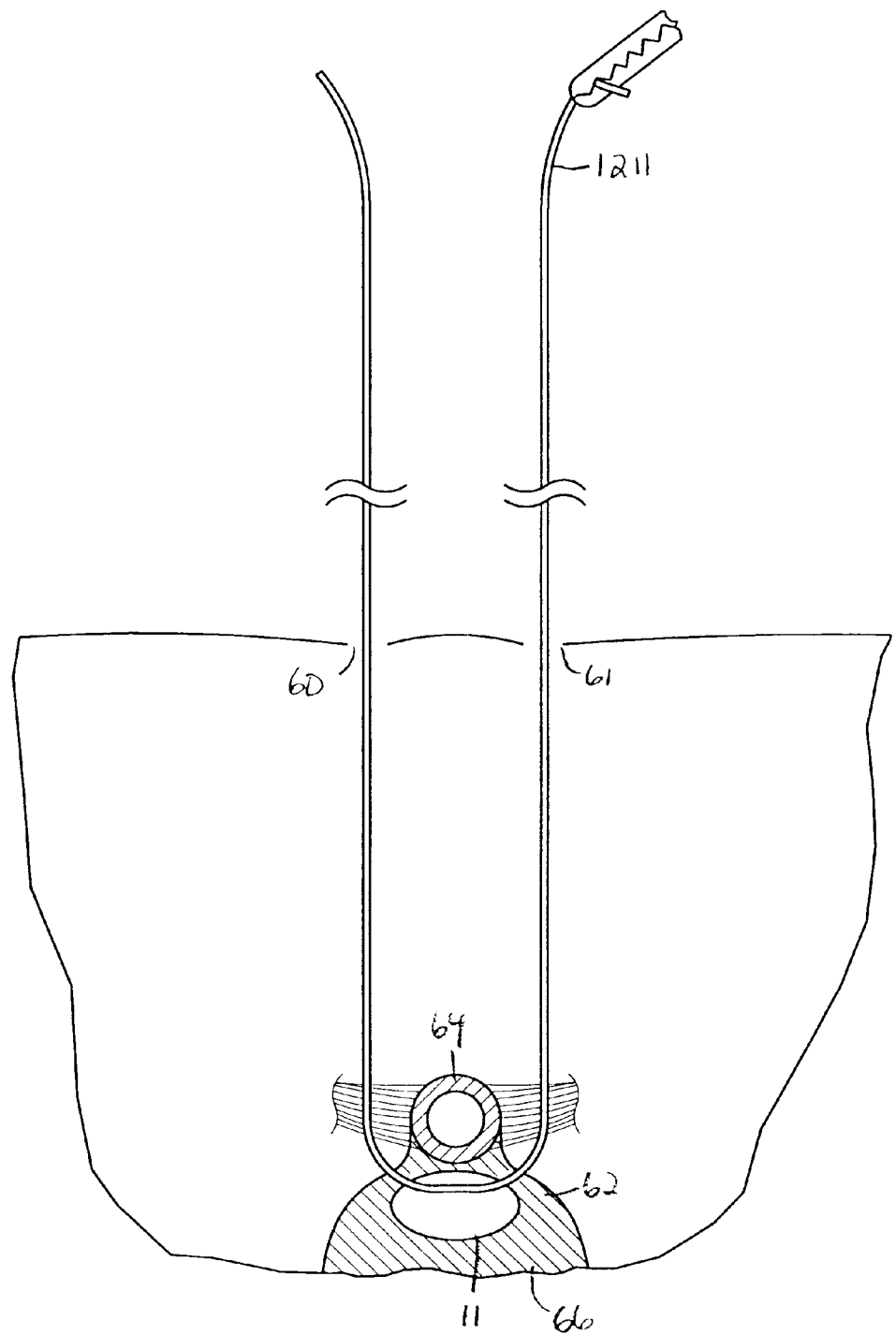
FIG. 65 shows the sling extending between the suprapubic incisions and passing through the tissue between the urethra and the upper vaginal wall.

As shown in FIG. 64, the proximal end of the sling 1212 which had formerly been inside the second shaft 718 is grasped, and the first shaft 716 is removed from the patient's body. After this procedure, the sling 1211 passes through the continuous opening in the patient's body tissue created by the above procedure, as shown in FIG. 65.

The sling 1212 may then be secured to a structure, such as the pubic bone by anchoring, stapling, riveting, or sewing to suspend or stabilize the bladder neck or create a platform to stabilize the urethral floor using approaches such as those disclosed in the copending U.S. patent application entitled "Stabilization Sling for Use in Minimally Invasive Pelvic Surgery" (VESITEC.023A), filed simultaneously herewith, the identically titled U.S. Provisional Patent Application Serial No. 60/038,379, filed Feb. 13, 1997, and U.S. Pat. No. 5,611,515, issued Mar. 18, 1997 to Benderev et al., the disclosures of which are incorporated herein by reference. Tension on the sling may be adjusted using procedures such as those disclosed in the U.S. Pat. No. 5,611,515, issued Mar. 18, 1997 to Benderev et al., the disclosure of which is incorporated herein by reference, to support the bladder neck or stabilize the urethral floor, thereby maintaining or improving urinary continence.

Detachable Member Sling Application Device and Retrieval Device

Another aspect of the present invention relates to a detachable member sling application device resembling the guide member placement device discussed above.

In general, the detachable member sling application device comprises a housing with an introduction shaft having a lumen extending therethrough connected to the housing. A detachable member is located on the distal end of the introduction shaft, the detachable member being connected to at least one of the sutures attached to the sling. The lumen in the shaft of the detachable member sling application device is capable of receiving a sling therein. Preferably, the sling is in an accordion like configuration when inside the lumen. The accordion like configuration may consist of random folds.

Optionally, the detachable member sling application device may further comprise an axially movable needle located inside the lumen of the introduction shaft. The needle, which comprises a needle shaft and a sharpened point, is extendable from the introduction shaft.

As illustrated in FIGS. 66–81, the shaft bends toward its distal end in the same manner as discussed above with regard to the guide member placement device.

A detachable member sling application device 1410 according to the present invention is depicted in FIGS. 66–79. The detachable member sling application device comprises a housing 1412 and a shaft 1414 with a lumen 1416 extending therethrough. The shaft 1414 has an engaging member 1411 near its distal tip for engaging a detachable member. Preferably, the engaging member 1411 comprises an annular ring on the outer surface of the shaft.

An axially movable inner shaft 1440 is located inside the shaft 1414 and is extendable therefrom and retractable therein. The axially movable inner shaft 1440 has a lumen extending therethrough. Movement of the axially movable inner shaft 1440 is controlled by an actuator 1442 which pivotally engages the housing 1412. Pivoting the actuator 1442 distally causes the axially movable inner shaft to move distally.

An axially movable plunger 1444 is located inside the axially movable inner shaft 1440 and is extendable therefrom and retractable therein. Movement of the axially movable plunger 1444 is controlled by a button 1446 which slidably engages the housing 1412. The button 1446 is movable between a first proximal position, a second intermediate position, and a third distal position. When the button 1446 is in first proximal position, sharpened point 1425 of the axially movable needle 1422 is retracted in the detachable member.

An axially movable needle 1422 having a shaft 1423 and a sharpened point 1425 at its distal end passes through an aperture in a deployment member 1448 which is located inside a detachable member 1424 located at the distal end of the shaft 1414. A spring 1413 is disposed between the deployment member 1448 and the detachable member 1424. The engaging member 1411 on the distal end of the shaft 1414 releasably engages the detachable member 1424. Preferably, the detachable member comprises a cup.

The detachable member 1424 has an engaging surface 1426 which engages the distal end of the shaft and a connecting member 1450. The connecting member 1450 is connected to at least one suture 1428 attached to a sling 1418 located in the lumen of the shaft 1414. Preferably, the sling 1418 is in an accordion like configuration inside the shaft 1414 to reduce the amount of space it occupies.

When the button 1446 is in the intermediate position, the sharpened point 1425 of the axially movable needle 1422 is extended from the detachable member 1424 so as to permit the tissue to be easily punctured while the device is advanced. When the button 1446 is in the distal position, the axially movable needle 1422 is maximally extended from the detachable member 1424 such that the shaft 1423 protrudes from the detachable member 1424 to permit extension through the hiatal area into the vagina for ease of grasping and securing.

Figure 67:
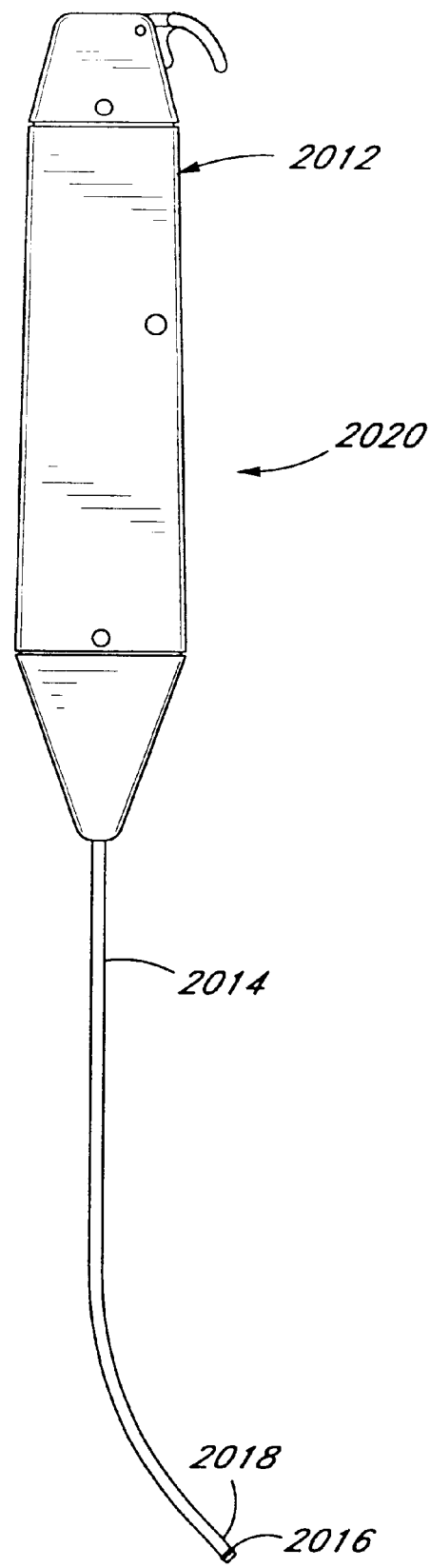
FIG. 67 is a side view of a retrieval device.

Another aspect of the present invention is a retrieval device for introducing a sling into an opening or pocket in a body tissue. One embodiment of the retrieval device is illustrated in FIG. 67. The retrieval device 2010 comprises a handle 2012 attached to a shaft 2014 having an engaging member 2016 near its distal end.

The handle 2012 of the retrieval device may have a variety of configurations which may vary depending on anatomical considerations and the type of procedure being performed. For example, the handle may have a similar configuration as that of the detachable member sling application device shown in FIG. 66.

Figure 66:
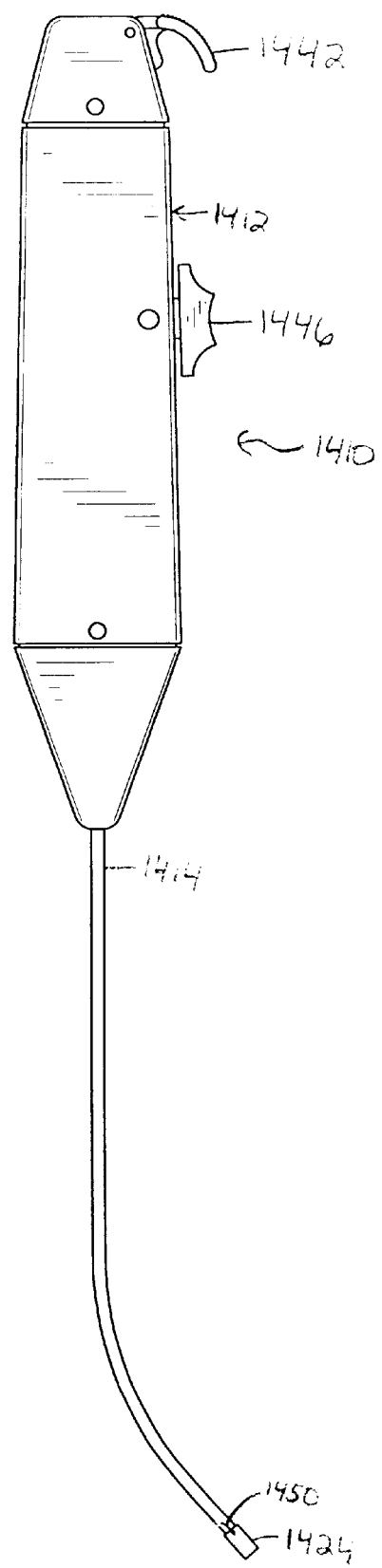
FIG. 66 is a side view of a detachable member sling application device.

Similarly, the shaft 2014 of the retrieval device may have the same configuration as the shaft 1414 of the detachable member sling application device 1410 shown in FIG. 66. Preferably, the engaging member 2016 comprises an annular ring on the outer surface of the shaft 2014.

In one embodiment, the retrieval device 2010 may be a modified detachable member sling application device 1410 having a hollow or solid shaft and lacking the actuator 1442, the button 1446, the detachable member 1424, the sling 1418, and the mechanism inside the shaft for deploying the detachable member.

The distal end of 2018 the shaft 2014 of the retrieval device has an engaging member 2016 adapted to engage the detachable member 1424. Preferably, the engaging member 2016 comprises an annular ring on the outer surface of the shaft. The shaft 2014 of the retrieval device may be solid or may have a hollow interior.

Although the detachable member sling application device 1410 and the retrieval device 2010 described above and depicted in FIGS. 66 and 67 may be used in a variety of procedures, a representative procedure for using the device to apply a sling beneath the female urethra is described below and depicted in FIGS. 68–81.

The first step of the procedure involves creating an opening or pocket 11 in the tissue 62 between the urethra 64 and the upper vaginal wall 66 into which the sling 1418 can be introduced. The opening or pocket 11 may be created in a variety of ways, including those described herein and in the copending U.S. patent application No. entitled "Stabilization Sling for Use in Minimally Invasive Pelvic Surgery" (VESITEC.023A) filed simultaneously herewith, and the identically titled U.S. Provisional Patent Application Serial No. 60/038,379, filed Feb. 13, 1997, the disclosures of which are incorporated herein by reference.

Figure 68:
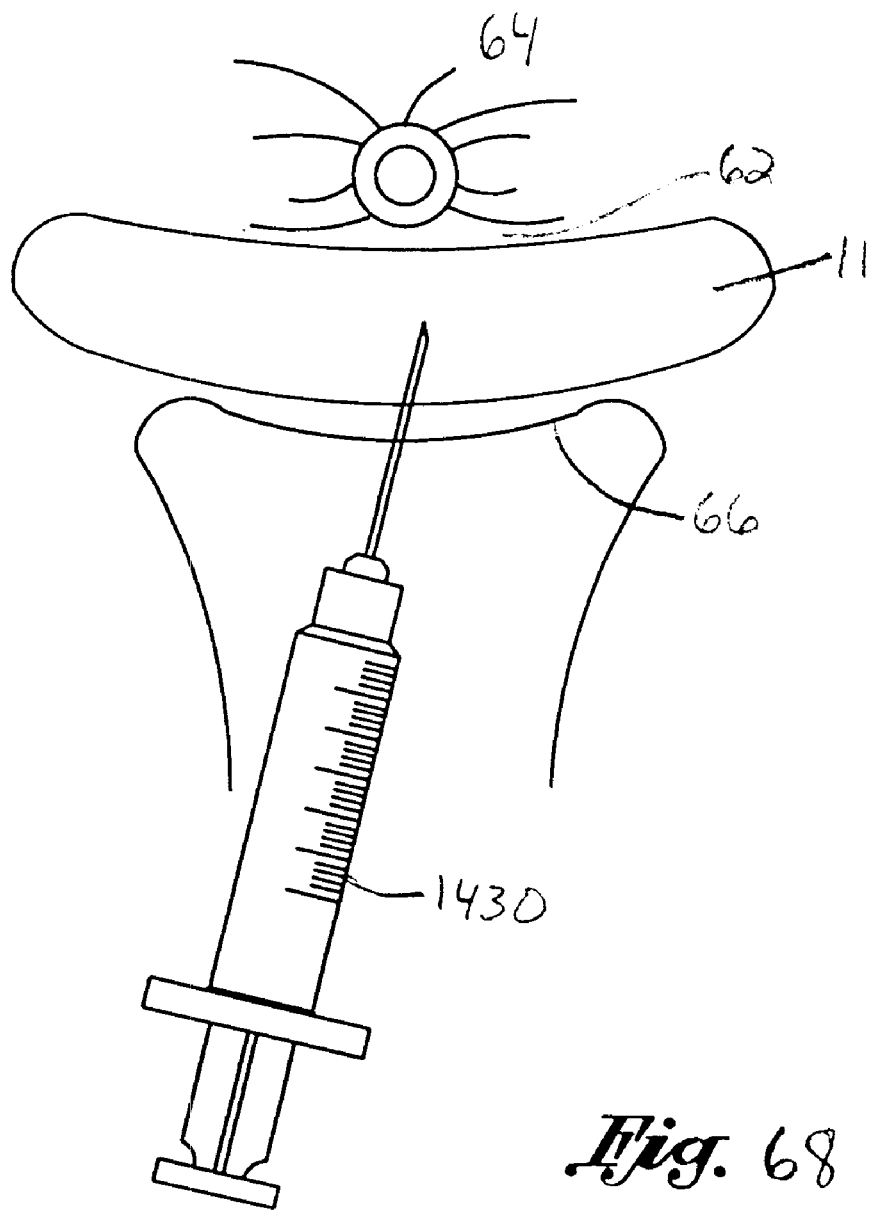
FIG. 68 shows the creation of an opening in the tissue between the urethra and the upper vaginal wall by hydrodissection.
Figure 69:
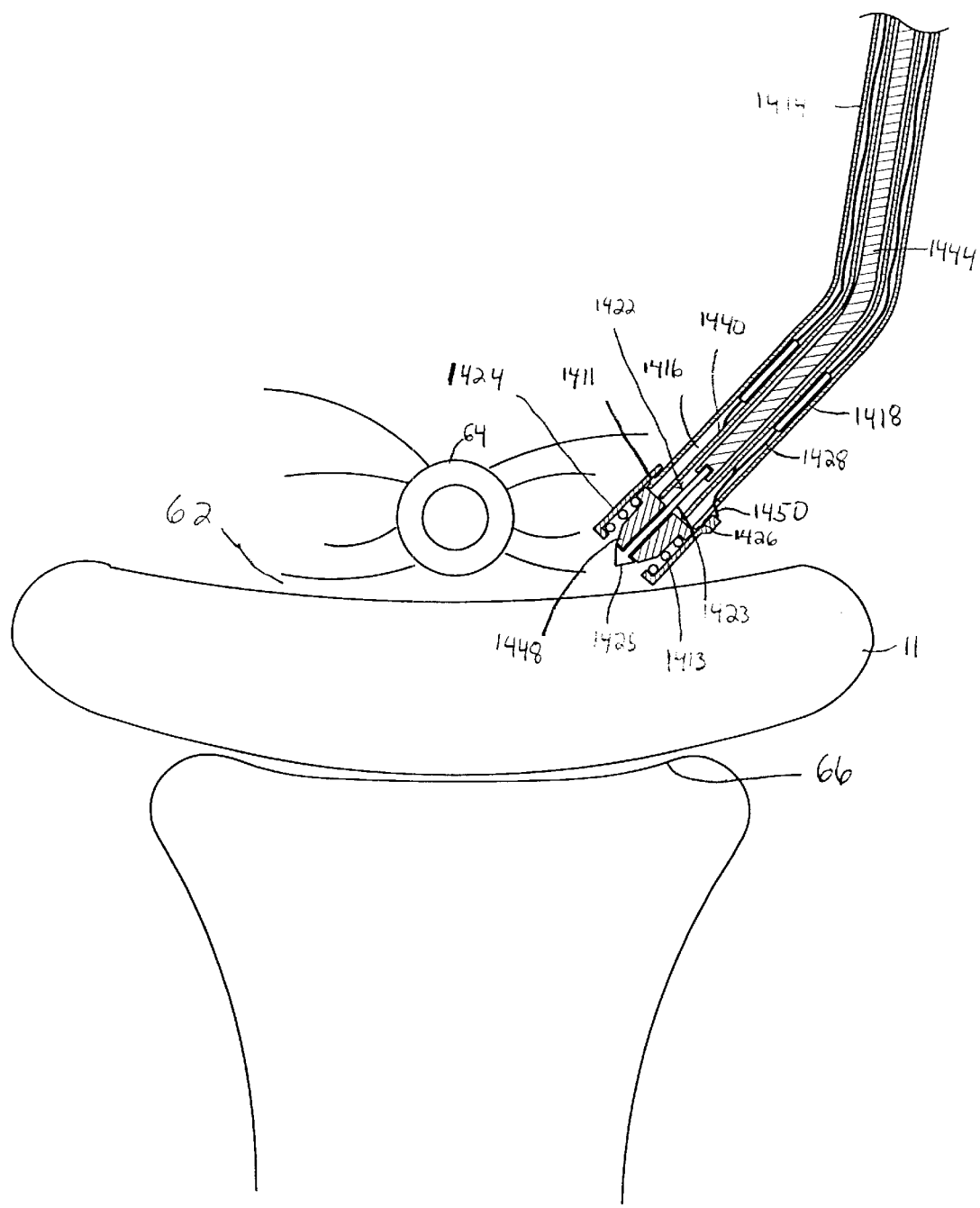
FIG. 69 shows the shaft of a detachable member sling application device sling application device being advanced to a pocket or opening in the tissue between the urethra and the upper vaginal wall.
Figure 10:
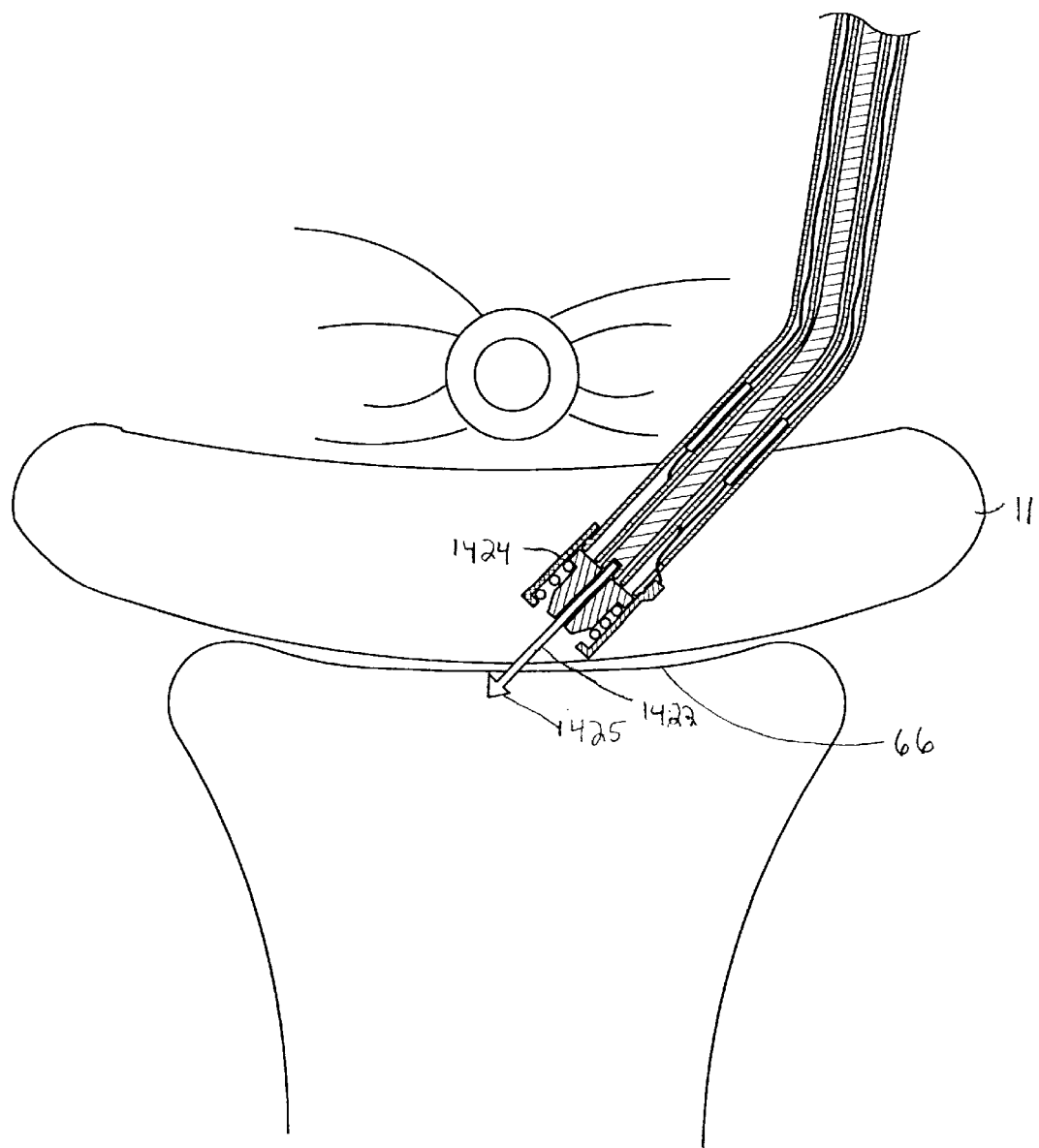

A preferred method of creating the pocket involves hydrodissection. As shown in FIG. 68, a syringe 1430 filled with saline is inserted through the vaginal wall 66 into the tissue 62 between the urethra and the upper vaginal wall. A bolus of saline is dispensed into the tissue, creating an opening or pocket 11 therein as shown in FIG. 68. Preferably, the bolus comprises about 4 cc of saline. The shaft 1414 of the detachable member sling application device is inserted percutaneously. For example, the shaft 1414 may be inserted percutaneously through a first suprapubic incision 61. The shaft 1414 of the detachable member sling application device 1410 is inserted therein. The shaft 1414 of the detachable member sling application device 1410 is advanced through the patient's body tissue along the back side of the pubic bone to the opening or pocket 11 created in the tissue 62 between the urethra 64 and the upper vaginal wall 66, as shown in FIG. 69. During advancement of the shaft 1414, the button 1446 may be advanced from the most proximal position, in which the sharpened point 1425 of the needle is within the detachable member 1424, to the intermediate position, in which the sharpened point 1425 of the needle extends from the detachable member. In particular, the sharpened point 1425 may be extended to dissect through muscle groups.

Figure 71:
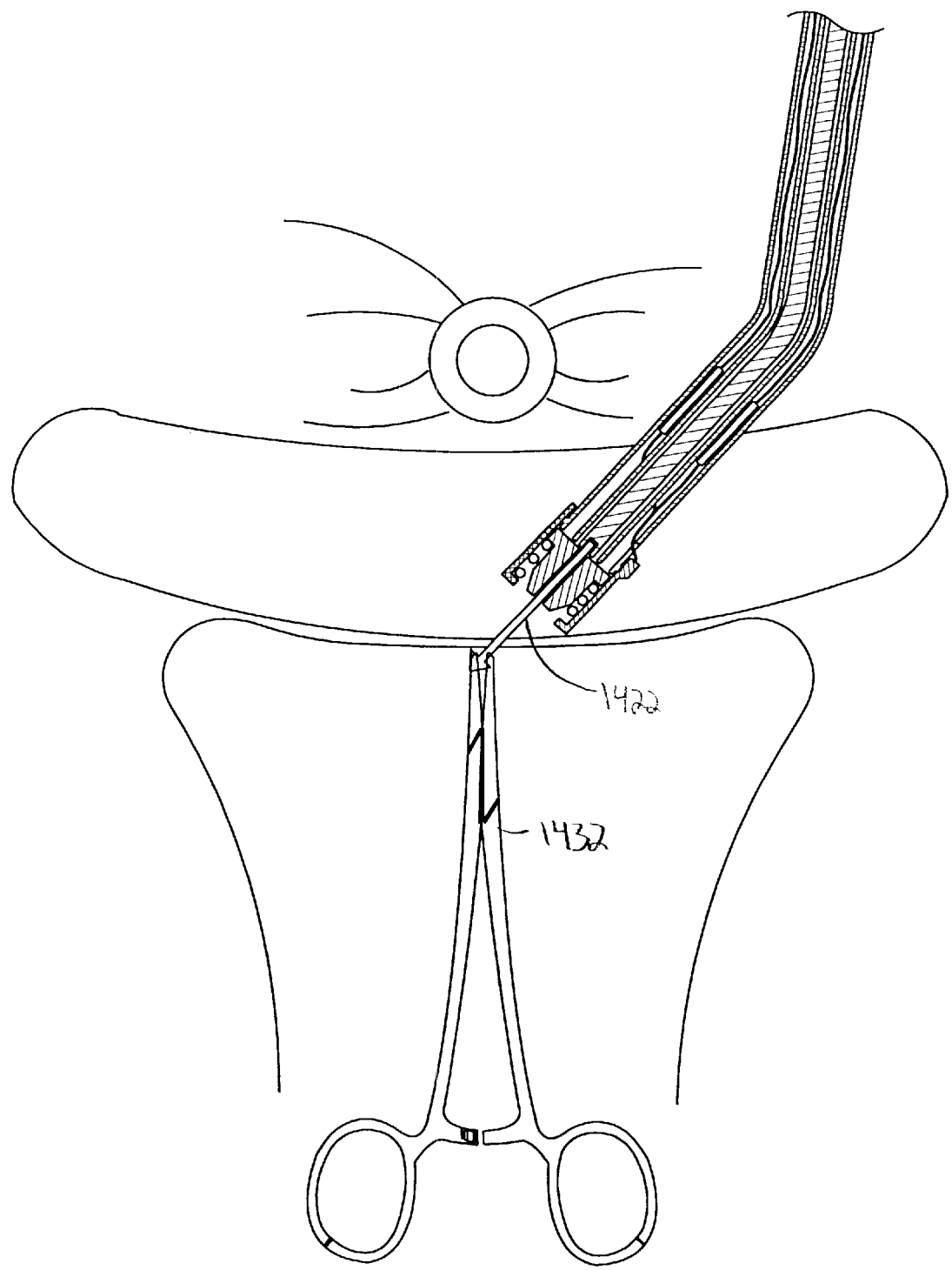
FIG. 71 shows the needle of the detachable member sling application device being secured on the vaginal side with a hemostat.

The distal end of the shaft 1414 is advanced percutaneously or laparoscopically to the bottom of the pocket or opening 11 and the button 1446 is advanced to the most distal position, in which the needle 1422 is maximally extended and the sharpened point 1425 passes through the upper vaginal wall 66 as shown in FIG. 70. The needle 1422 is secured on the vaginal side with a device such as a hemostat 1432 as shown in FIG. 71.

Figure 72:
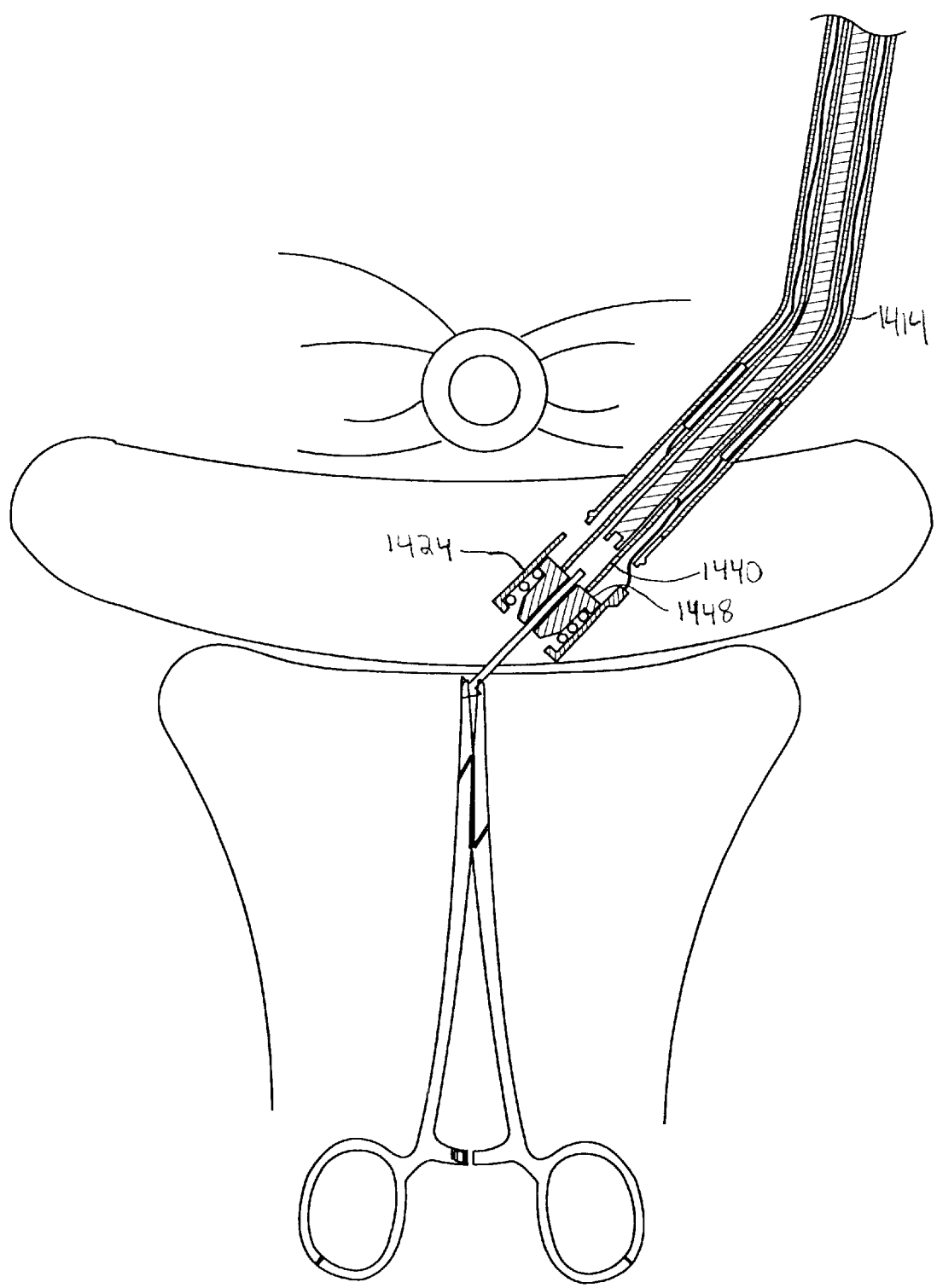
FIG. 72 shows the detachable cup being detached from the distal end of the shaft of the detachable member sling application device.

As shown in FIG. 72, the detachable member 1424 is then detached from the distal end of the shaft 1414 by pivoting the actuator 1442 distally, thereby causing the inner shaft 1440 to move distally such that it contacts the deployment member 1448 and pushes the detachable member 1424 off the distal end of the shaft 1414.

Figure 73:
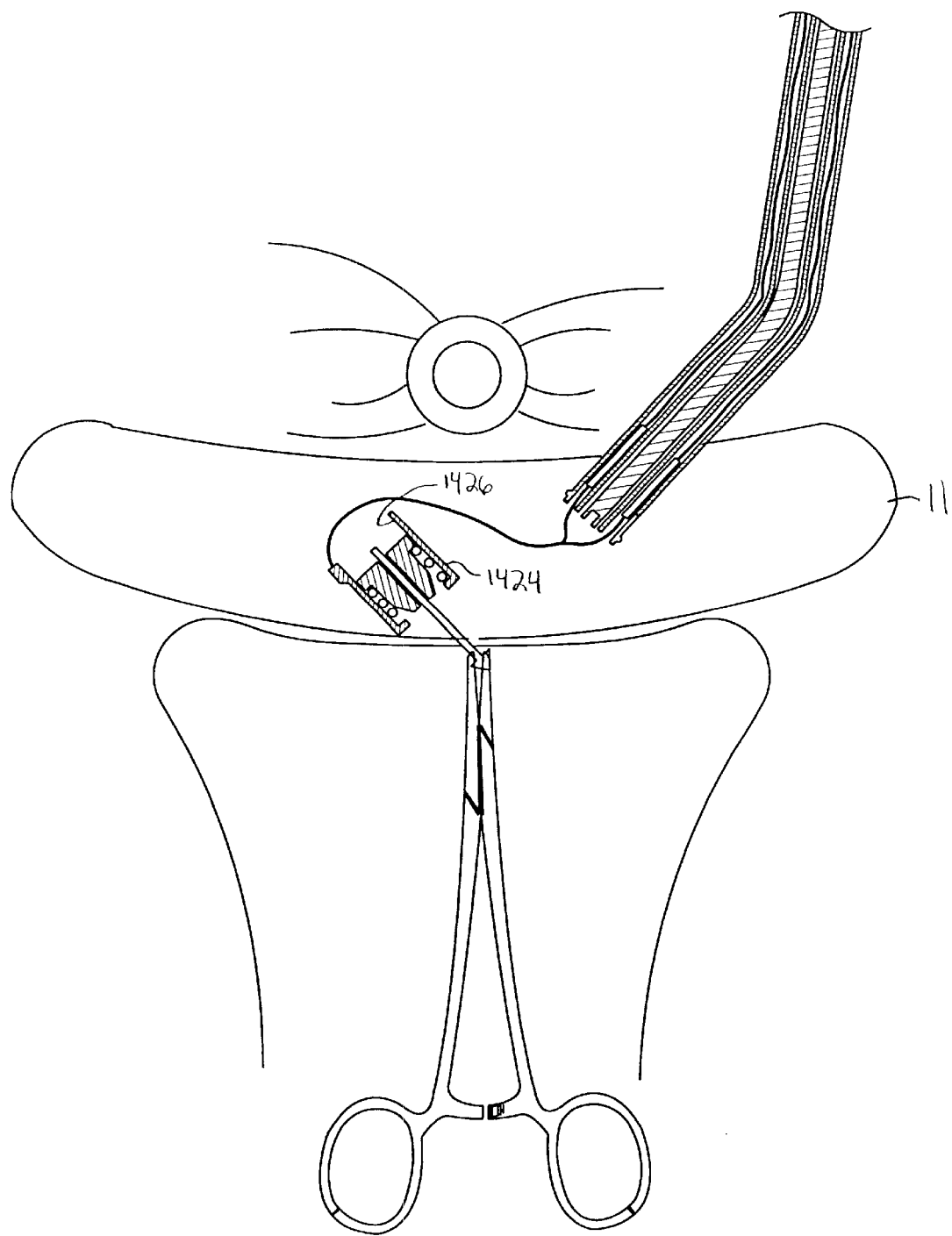
FIG. 73 shows the needle of the detachable member sling application device being toggled.

As illustrated in FIG. 73, the needle 1422 is toggled within the pocket or opening 11 such that the engaging surface 1426 of the detachable member will be accessible to the engaging member 2016 of a retrieval device 2010. Preferably, the needle is toggled from about 30° to about 150°. More preferably the needle is toggled from about 60° to about 120°. In a highly preferred embodiment, the needle is toggled about 90°.

As will be appreciated by those skilled in the art, other methods of positioning the detachable member for engaging the engaging member of a retrieval device may be used with embodiments of the detachable member sling application device which do not have the axially movable needle.

Figure 74:
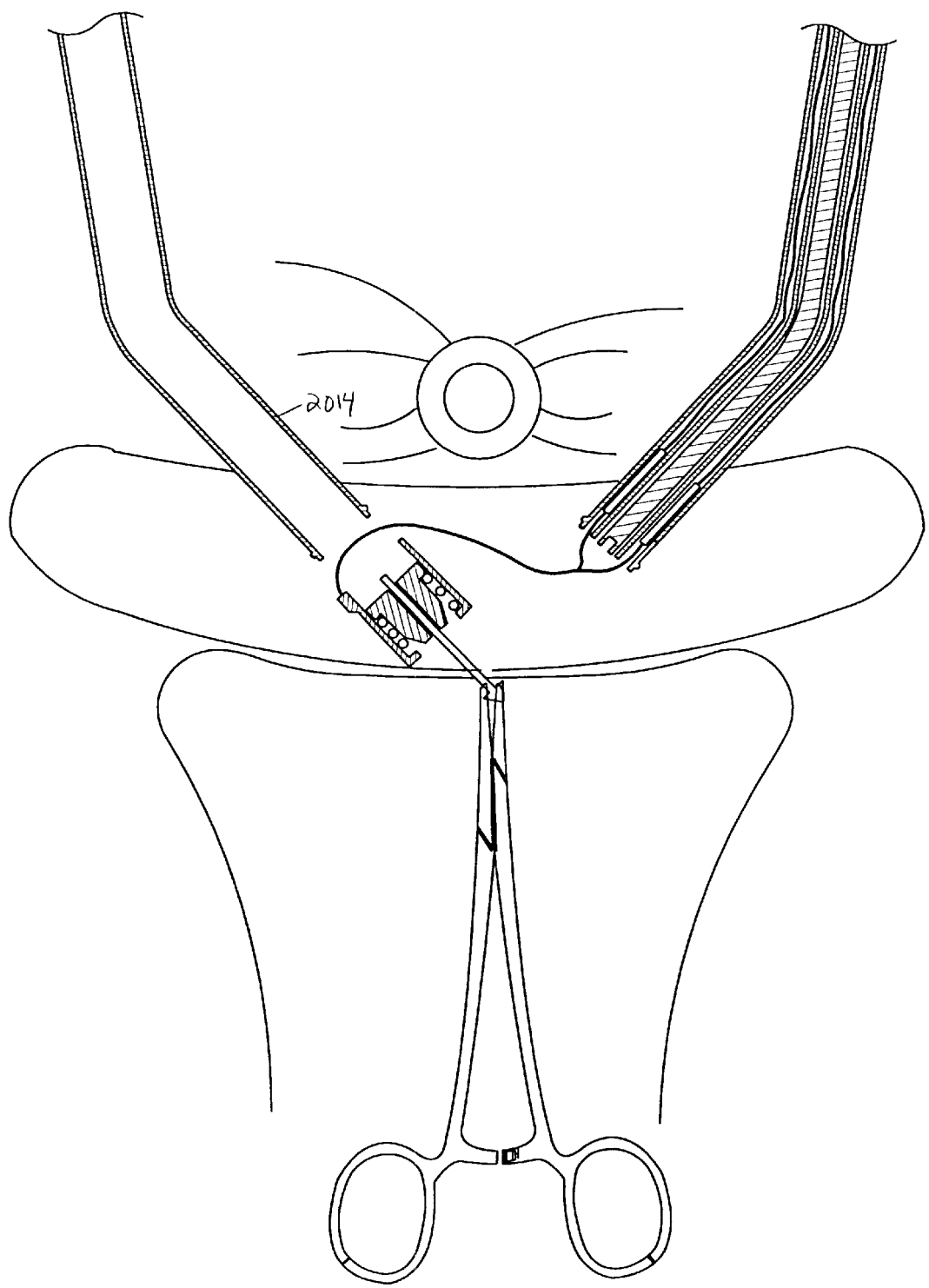
FIG. 74 shows the shaft of a retrieval device being advanced through a second suprapubic incision into the pocket.

The shaft 2014 of a retrieval device is advanced percutaneously or laparoscopically into the opening or pocket 11 as shown in FIG. 74. For example, the shaft may be advanced into the opening or pocket through a second suprapubic incision 60.

Figure 75:
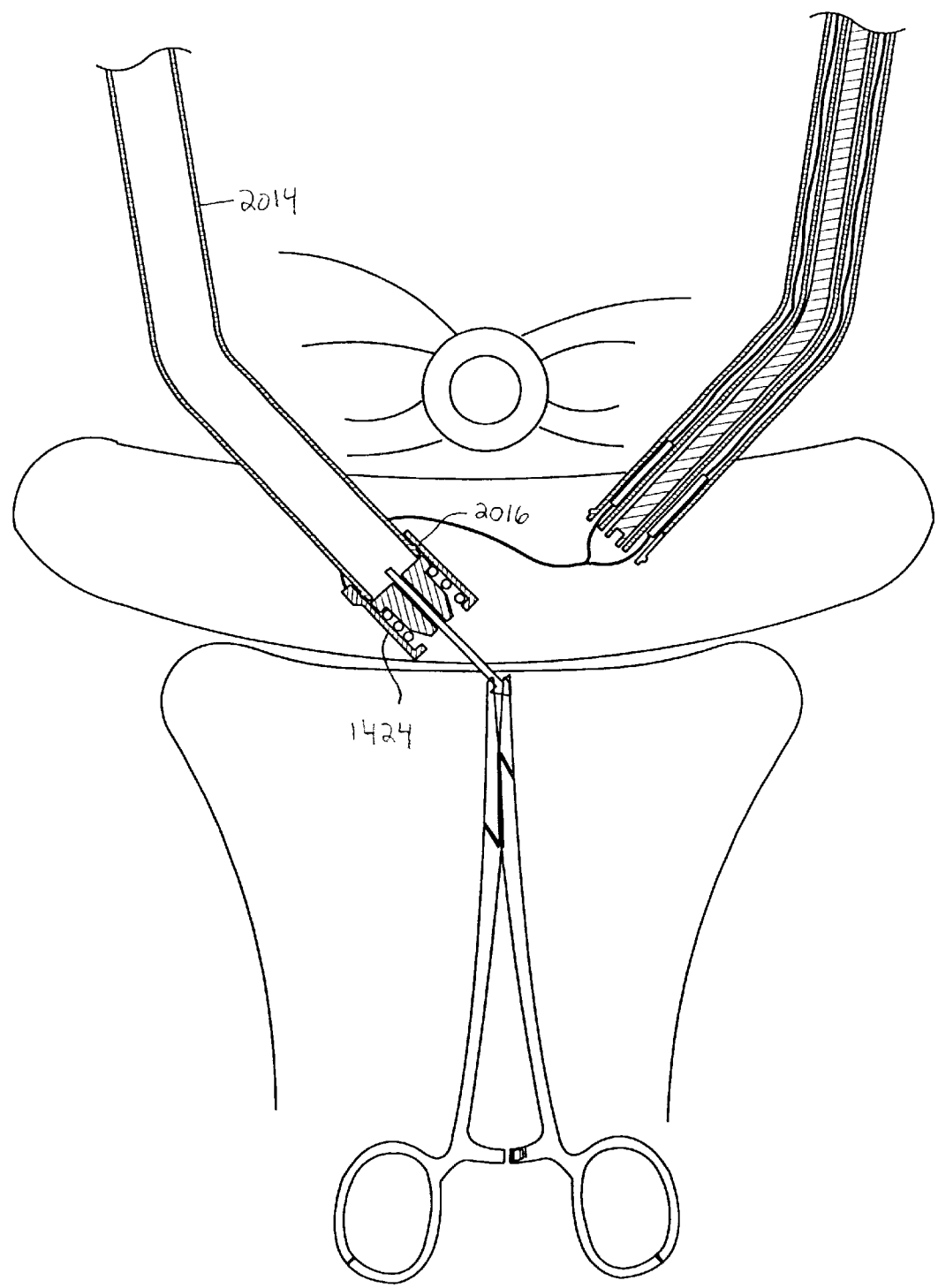
FIG. 75 shows the shaft of the retrieval device being inserted into the detachable cup and engaging the detachable cup.
Figure 76:
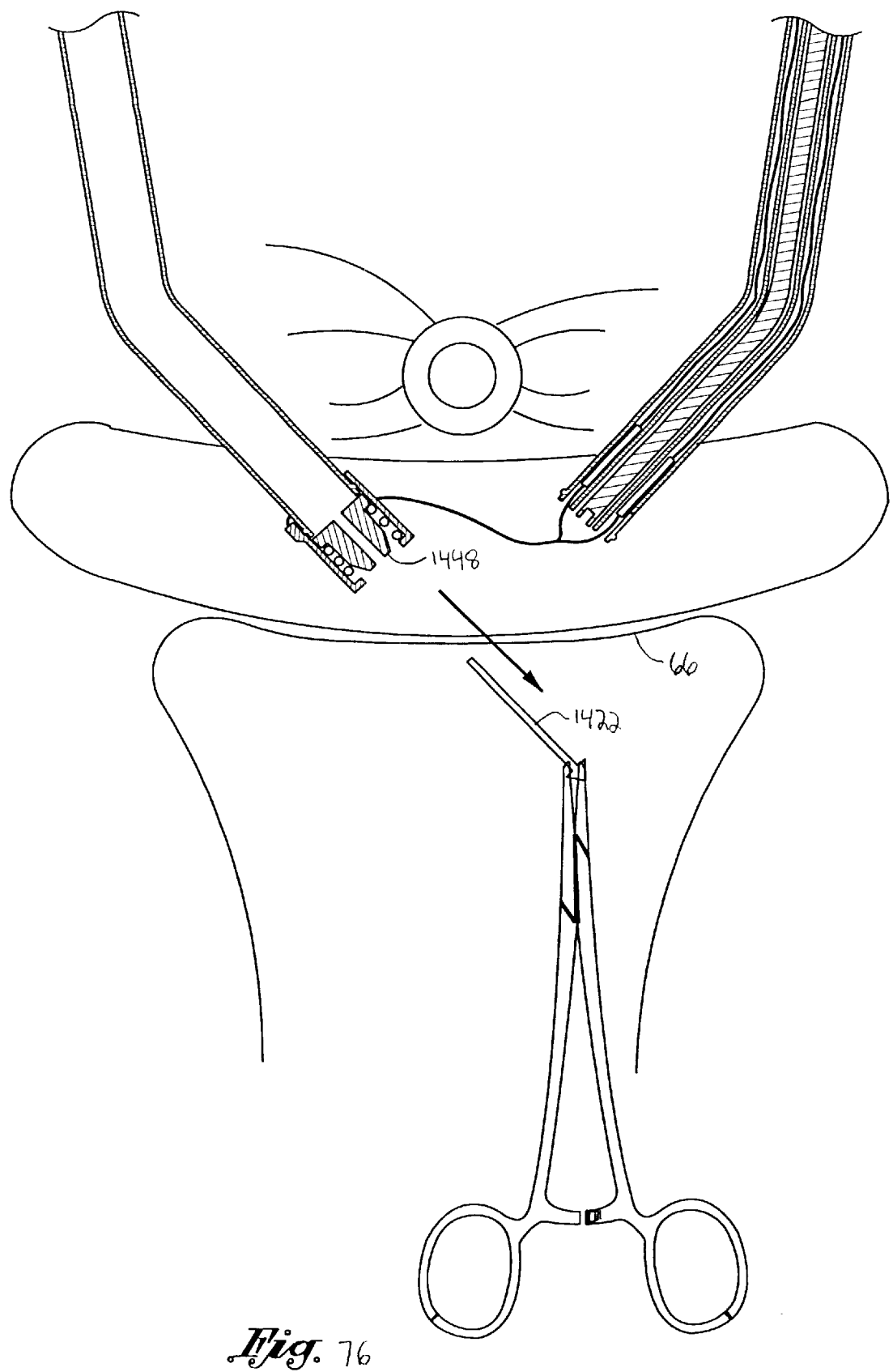
FIG. 76 shows the needle being removed from the vagina.

The distal end of the shaft 2014 of the retrieval device is inserted into the detachable member 1424 and the engaging member 2016 engages the engaging surface 1426 of the detachable member 1424 as shown in FIG. 75. As shown in FIG. 76, the needle 1422 protruding through the vaginal wall 66 is then pulled out of the deployment member 1448 and removed from the vagina so as not to draw bacteria back into the pelvic area.

Figure 77:
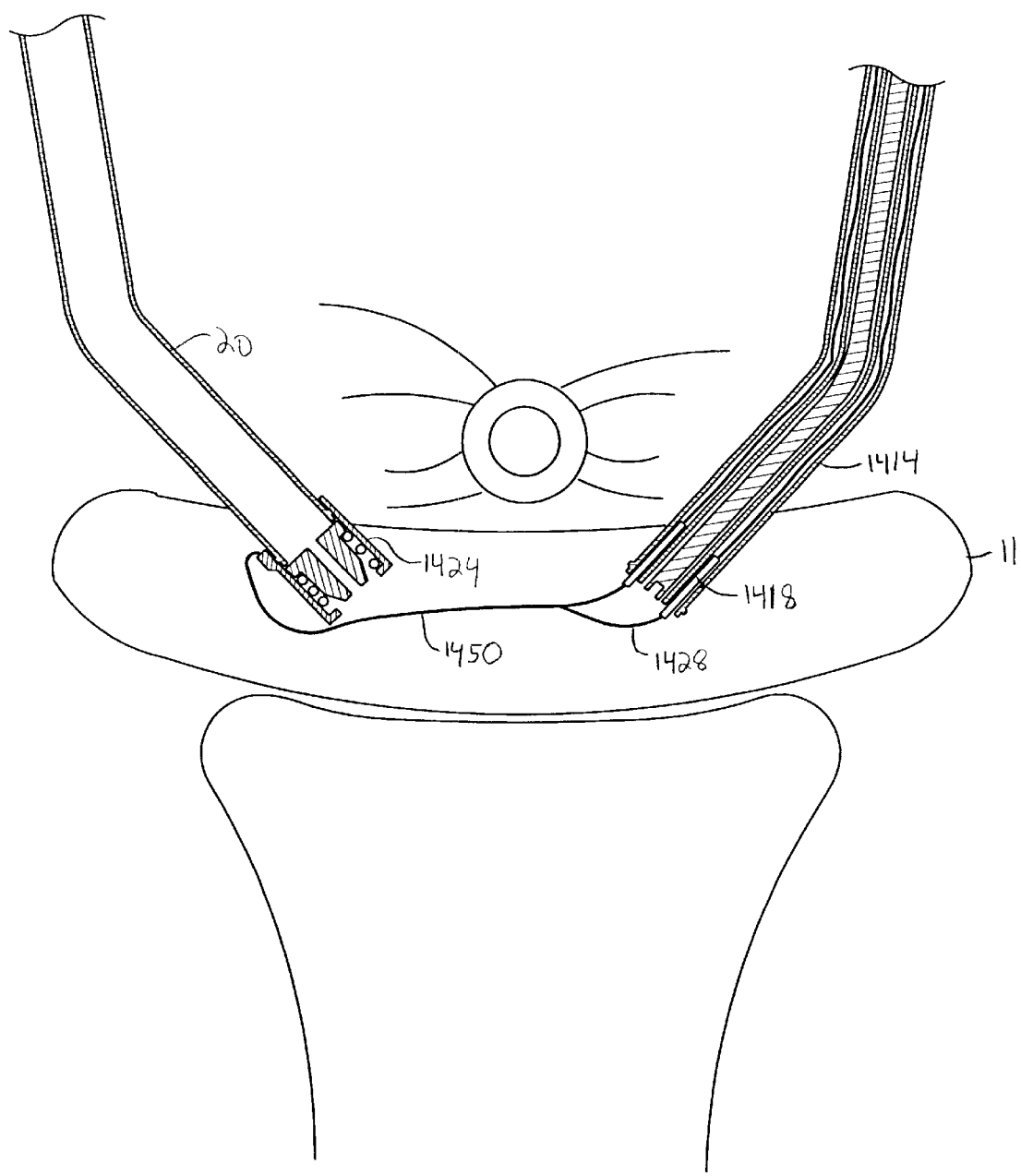
FIG. 77 shows the sutures connected to the sling being pulled out of the shaft of the detachable cup sling application device.
Figure 78:
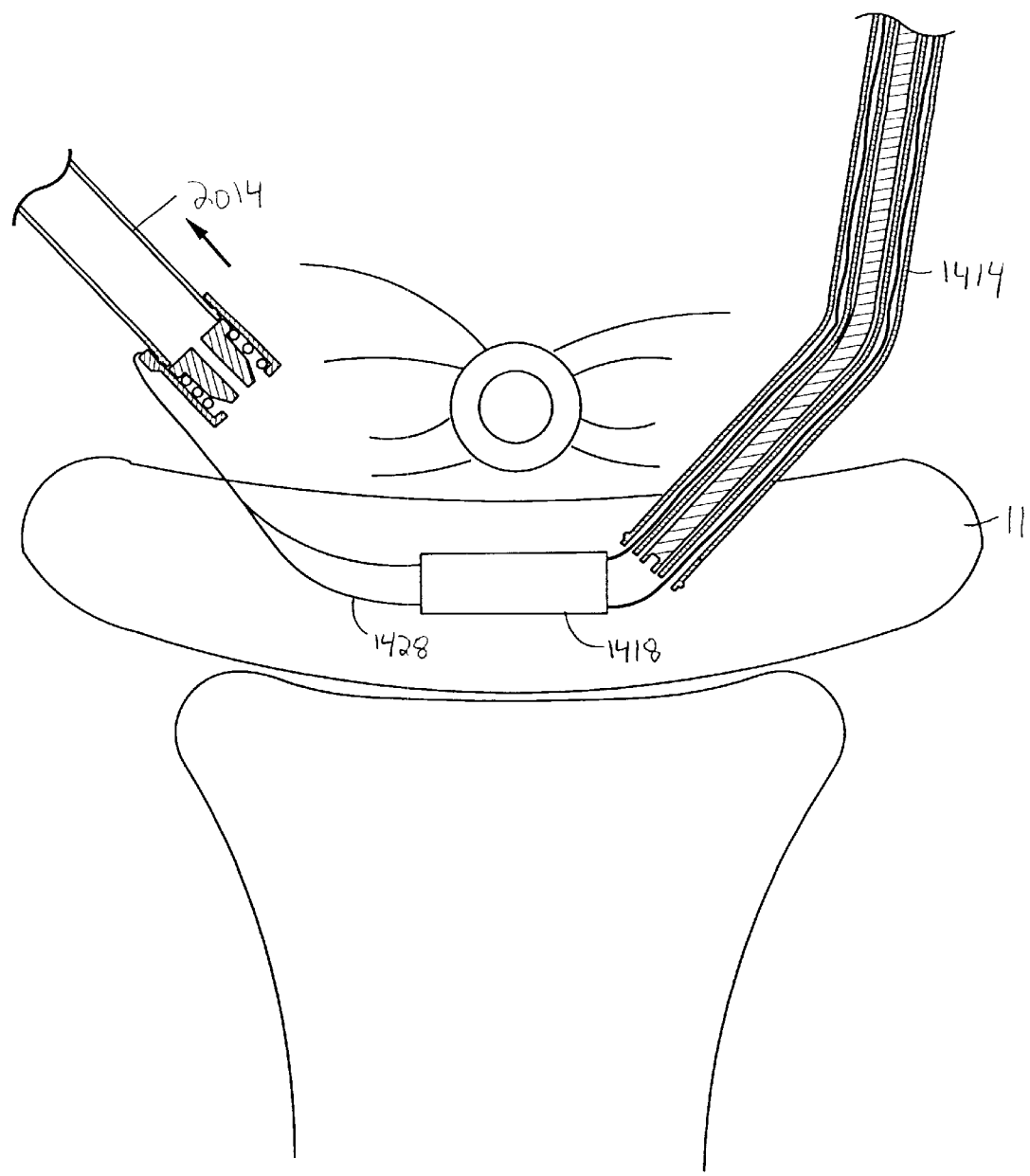
FIG. 78 shows the shaft of the retrieval device being withdrawn from the pocket or opening, pulling the sling out of the shaft of the detachable member sling application device.

As the shaft 2014 of the retrieval device is withdrawn from the pocket or opening 11, the connecting member 1450 on the detachable member 1424 pulls the sutures 1428 connected to the sling 1418 out of the shaft 1414 of the detachable member sling application device 1410, as illustrated in FIG. 77. As the shaft 2014 of the retrieval device is withdrawn further from the pocket or opening 11, the sling 1418 and the sutures 1428 connected thereto are pulled out of the shaft 1414 of the detachable member sling application device 1410, as illustrated in FIG. 78.

Figure 79:
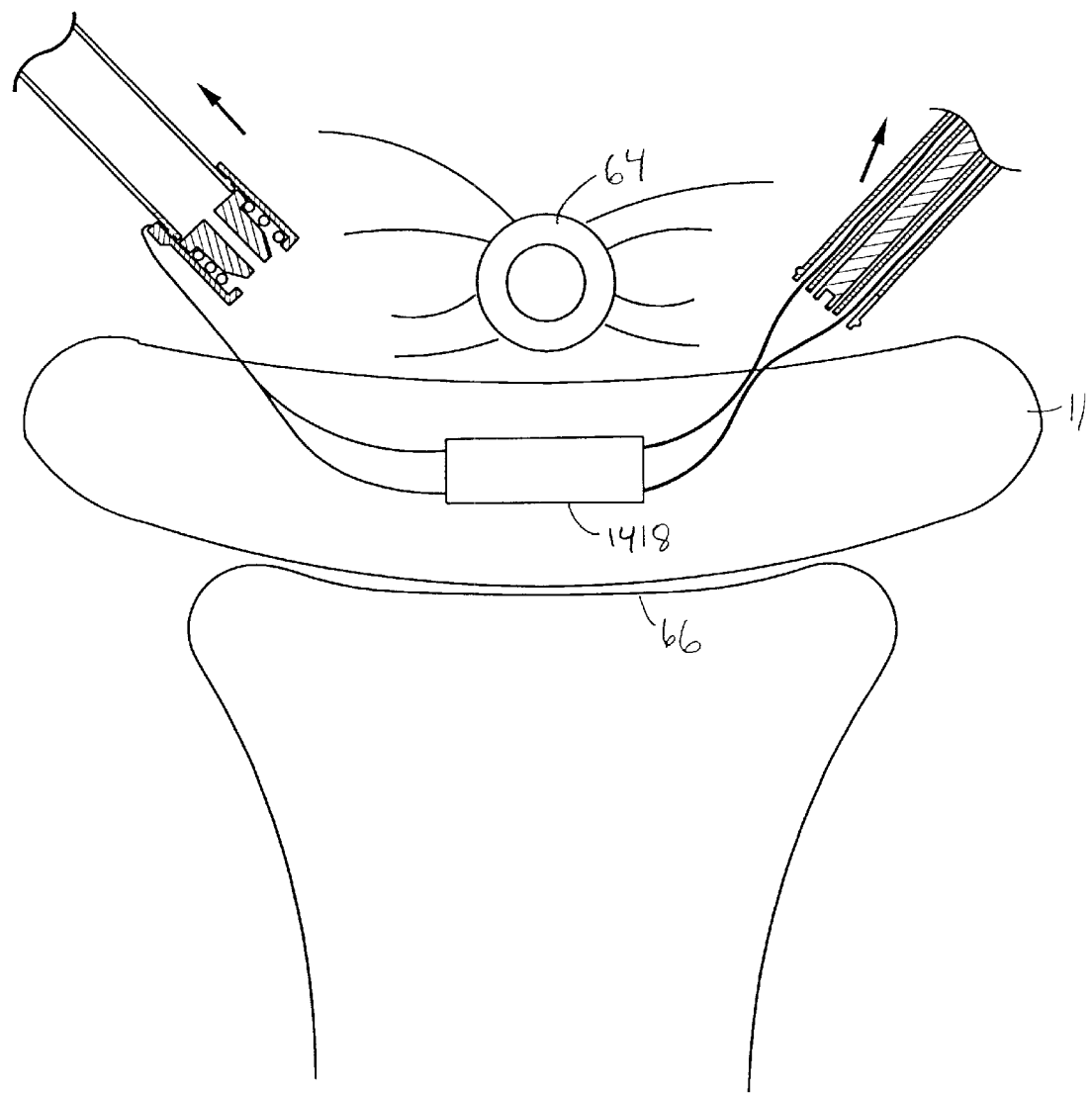
FIG. 79 shows the shafts of the retrieval device and the detachable member sling application device being withdrawn from the pocket.
Figure 80:
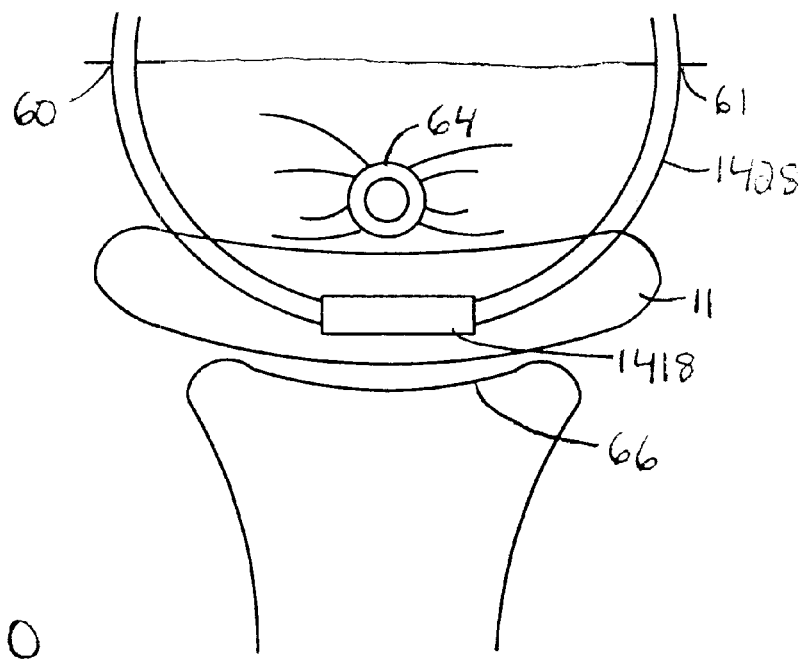
FIG. 80 shows the sling located in the opening in the tissue between the urethra and the upper vaginal wall with the sutures extending through the incisions to the outside of the patient's body.

The shaft 1414 of the detachable member sling application device 1410 and the shaft 2014 of the retrieval device 2010 are withdrawn from the patient's body as shown in FIG. 79. The sling 1418 is thereby left in the opening or pocket 11 between the urethra 64 and the upper vaginal wall 66 such that the sutures 1428 extend from the first and second suprapubic incisions 60, 61 patient's body, as shown in FIG. 80.

Figure 81:
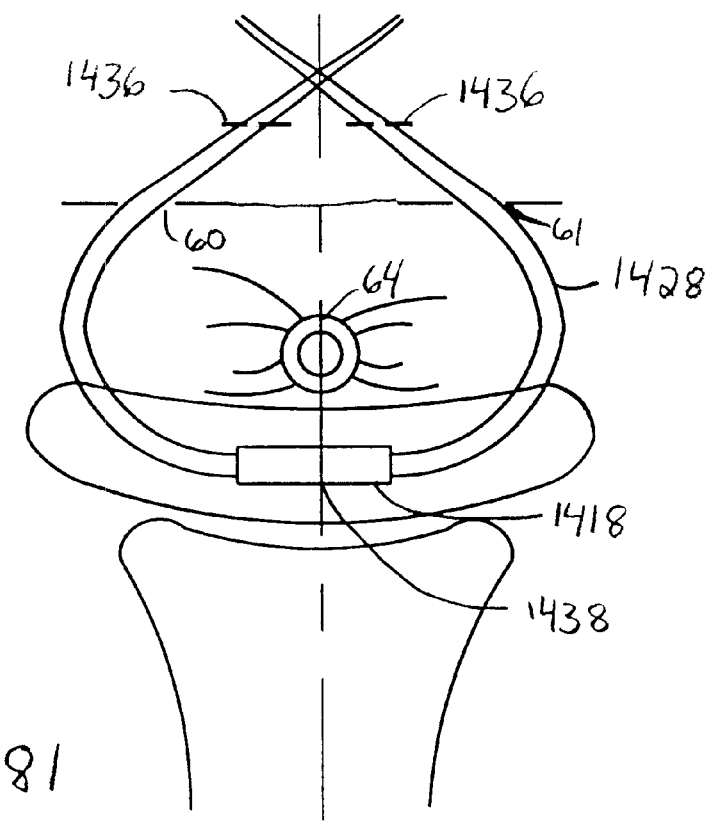
FIG. 81 shows the marks on the sutures being aligned to ensure centering of the sling beneath the urethra within the opening in the tissue between the urethra and the upper vaginal wall.

Preferably, the sutures 1428 or integral attachment members attached to the sling 1418 have markings 1436 thereon for ensuring that the sling 1418 is properly centered beneath the urethra in the opening or pocket 11. The markings 1436 on the sutures or integral attachment members are equidistant from the center 1438 of the sling. Following placement of the sling 1418 in the opening or pocket 11, the physician crosses the sutures 1428 as shown in FIG. 81. When the markings 1436 on the sutures 1428 or integral attachment members are positioned along a line extending transversely to the patient's abdomen, as shown in FIG. 81, the sling 1418 is properly centered in the pocket or opening 11.

The sling can then be attached to a bone anchor or other structures, and tensioned to support the bladder neck or stabilize the urethral floor, thereby maintaining or improving urinary continence, using approaches such as those described in the copending U.S. patent application entitled "Stabilization Sling for Use in Minimally Invasive Pelvic Surgery" (VESITEC.023A), filed simultaneously herewith, the identically titled U.S. Provisional Patent Application Serial No. 60/038,379, filed Feb. 13, 1997 and U.S. Pat. No. 5,611,515, issued Mar. 18, 1997 to Benderev et al., the disclosures of which are incorporated herein by reference.

Tissue Expander, Grasping Device, and Balloon Catheters

A further aspect of the invention relates to hiatal techniques for creating an opening or pocket in the tissue between the urethra and the upper vaginal wall and devices for use in the hiatal techniques. The hiatal methods can be practiced without the necessity for a vaginal incision, thus minimizing the risk of infection from the procedure.

As will be described in greater detail below, in the hiatal approach a lumen is created in the hiatal tissue between the urethra and the upper vaginal wall. The lumen is then expanded to create an opening or pocket of a size sufficient to accept a sling. The opening or pocket is then held open with the tissue expander while a first suture or flexible guide member is percutaneously advanced into the opening or pocket. The guide member may be a suture, guidewire, or other structure suitable for guiding a sling to a desired location. The first suture or flexible guide member is grasped with a grasping device and withdrawn through the lumen and out of the body. The process is repeated with a second suture or flexible guide member on the opposite side of the urethra. The two sutures or flexible guide members are then tied together to create a guide for delivering a sling into the pocket. The knotted section of the suture or guide member is then translocated outside of the body so that the progress of the sling along the suture or guide member is unimpeded.

Alternatively, the sling may be attached to the sutures extending outside of the body, rolled or restuffed, and drawn into the body through the lumen by pulling on the sutures.

As discussed above, after creation of the lumen in the hiatal tissue, the lumen is expanded to create a pocket or opening. One aspect of the present invention relates to balloon catheters for expanding the lumen and creating the pocket or opening. The balloon catheters generally comprise an outer tube having a lumen extending therethrough and at least one expandable balloon inside the outer tube. The expandable balloon has a blunt dissection tip at its distal end having sufficient rigidity to allow it to create an opening in a body tissue when contacting the tissue.

One embodiment of a balloon catheter 536 suitable for use in the hiatal approach was described above and is shown in FIG. 26.

In the embodiment shown in FIG. 26, there is a single expandable balloon 540. In an alternative embodiment of the balloon catheter, there is more than one balloon. This embodiment permits the creation of an opening or pocket wide enough to accommodate the sling using balloons having a smaller diameter than would a single balloon capable of creating a pocket of that width. In this way, tearing of tissue above and below the pocket is minimized.

Figure 82:
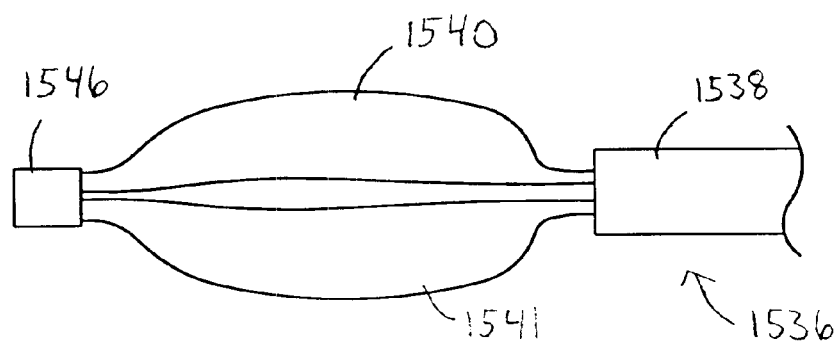
FIG. 82 is a side view of a balloon catheter having two expandable balloons joined at their distal ends.

FIG. 82 shows a preferred embodiment 1536 in which there are two expandable balloons 1540 and 1541 in the lumen of the outer tube 1538 which are joined at their distal ends. Preferably, the expandable balloons are joined at their distal ends by a blunt dissection tip 1546. The blunt dissector tip may comprise a plastic or metal cap. Alternatively, the ends of the two balloons may be potted together. In the embodiment of FIG. 82, the two balloons have a common inflation tube. However, those skilled in the art will appreciate that the balloons may also have separate inflation tubes.

Figure 83:
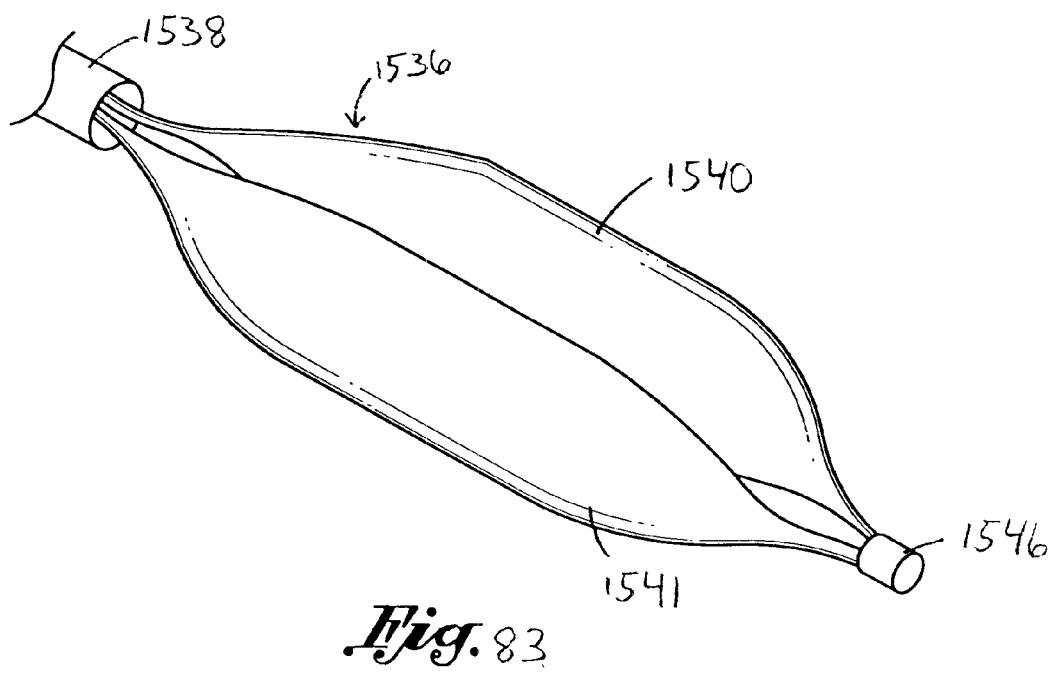
FIG. 83 shows the balloon catheter of FIG. 82 with the balloons expanded.

FIG. 83 shows the embodiment of FIG. 82 in which the balloons 1540, 1541 have been inflated. As illustrated in FIG. 83, the balloons 1540, 1541 have a generally cylindrical configuration when inflated. In this embodiment, each balloon 1540, 1541 may be from about 2 cm to about 3 cm in length and has a diameter when expanded of from about 1 cm to about 2.5 cm. In a preferred embodiment, each balloon 1540, 1541 is from about 2 cm to about 3 cm in length and has a diameter when expanded of from about 1.5 cm to about 2 cm. More preferably, each balloon is about 2.75 cm in length and 2.5 cm in diameter when expanded.

Some physicians prefer procedures which take place beneath the pelvic floor so as to avoid any unnecessary disruption of muscle, the slings are preferably about 1.5 cm to about 6 cm in length and about 2 cm in width. More preferably, the slings used in such procedures are 2.5 cm to 4 cm in length, although longer slings may be more manageable for general surgeons since they allow for slippage off center during placement.

Other physicians prefer procedures which break through the pelvic floor and produce scarring which may reinforce the area. In such procedures, the slings may be as long as 20–25 cm. These long slings minimize the length of attaching suture and permit more tissue ingrowth while providing security against suture breakage. Preferably, the slings used in such procedures are about 2 cm wide.

Those skilled in the art will appreciate that the sling dimensions can be varied as appropriate. In any case, however, it is preferred that the balloon on the balloon catheter is appropriately sized to create a pocket or opening capable of accommodating the sling.

Alternatively, a balloon catheter 1636 having a flat profile balloon 1640 may be used to create the lumen. The flat profile balloon 1640 is capable of forming a flat pocket sized to receive a sling while avoiding the unnecessary dilation or tearing of tissue above and below the sling pocket which may occur if a cylindrical balloon was used to create the pocket. Preferably, the flat profile balloon 1640 has a square or rectangular shape when inflated. However, those skilled in the art will appreciate that other shapes are compatible with the present invention and that the shape may be readily modified to be compatible with the particular device or procedure used.

The flat profile balloons 1640 are preferably made of two sheets of noncompliant material such as mylar, polyethylene, or PET. Alternatively, the balloons may be made by blow molding.

Figure 84:
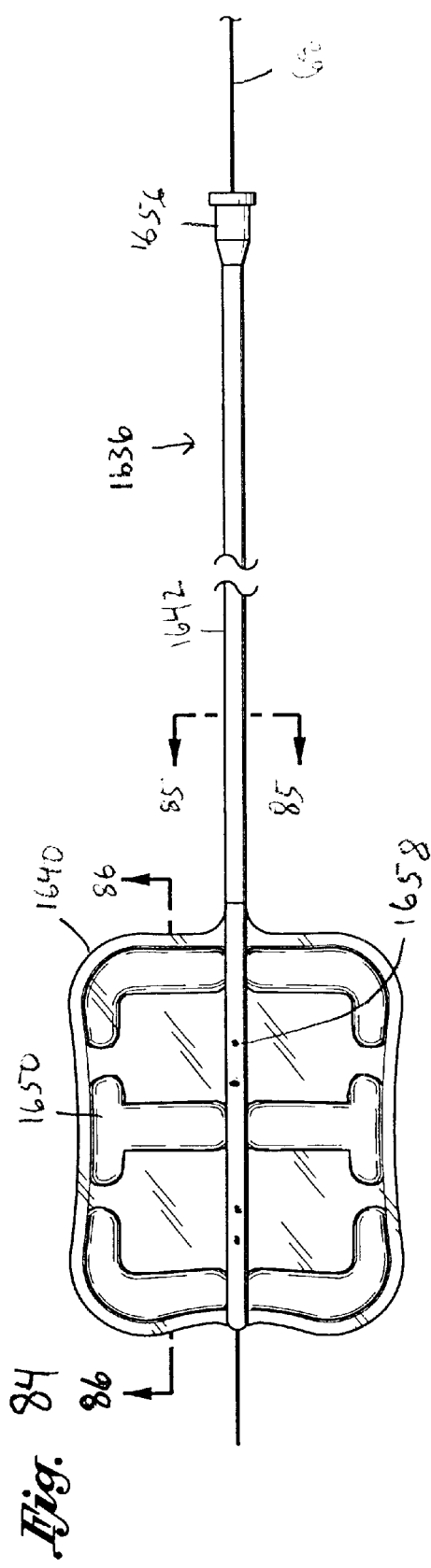
FIG. 84 is a plan view of the balloon catheter having a flat profile balloon.

A flat profile balloon 1640 according to the present invention is shown in FIG. 84. As illustrated, the balloon 1640 has a series of internal non-expansive ribs 1650 which serve to maintain a shallow profile after expansion, direct the flow of air to promote even unrolling during expansion, reduce buckling in critical areas after expansion, and provide a conduit structure which delivers a consistent expansion of tissue into the desired shape. The internal structure of the catheter and balloon 1640 are further illustrated in the cross sectional views of FIGS. 85 and 86.

As illustrated in FIG. 84, the balloon 1640 is located at the distal end of a generally rigid inflation tube 1642 which extends through the interior of the balloon 1640. The inflation tube 1642 provides a generally rigid support structure during advancement and placement of the balloon 1640 in the body tissue. Preferably, the inflation tube 1642 has a series of fill holes 1658 in the interior of the balloon 1640 which promote uniform inflation of the balloon. However, those skilled in the art will appreciate that a single fill hole may also be used.

Figure 85:
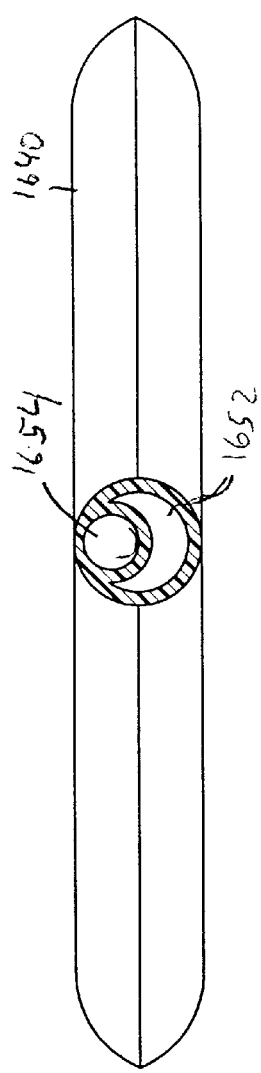
FIG. 85 is a cross-sectional view taken along line 85—85 of the balloon catheter of FIG. 84.
Figure 86:
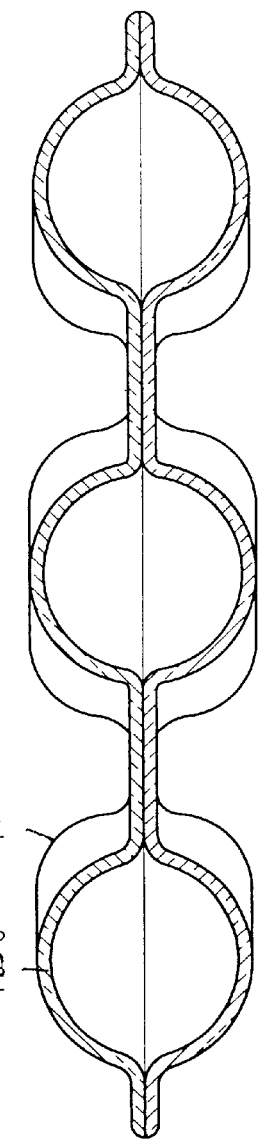
FIG. 86 is a cross-sectional view taken along line 86—86 of the balloon catheter of FIG. 84.

In one embodiment, shown in FIG. 85, the inflation tube 1642 has two lumens in its interior. One lumen, the guide lumen 1652, is adapted to receive a guide member, while the other lumen, the inflation lumen 1654, is for inflation of the balloon and is in fluid communication with the interior of the balloon. In an alternative embodiment, the catheter has a single inflation lumen.

Those skilled in the art will appreciate that the catheter may be provided with more than two lumens to accommodate other instruments necessary to perform the surgical procedure.

The inflation tube has a luer tip 1656 at its proximal end which is adapted to engage a syringe filled with saline or sterile water. When the plunger of the syringe is depressed, fluid is force through the inflation lumen 1642 and out of the fill holes into the interior of the balloon, causing the balloon 1640 to inflate. When the plunger of the syringe is retracted, a vacuum is created, drawing the fluid out of the balloon 1640 and causing the balloon to deflate 1640.

In a preferred embodiment, the balloon 1640 is rolled on the exterior surface of the inflation tube 1642 to reduce its entry profile.

Those skilled in the art will appreciate that the above described balloon catheters 536, 1536, 1636 can be used to dilate body tissues in contexts other than the hiatal procedures discussed below. For example, the balloon catheters 536, 1536, 1636 may be utilized in the tissue dissector/dilator 510 described above, or may be used to create a pre-formed opening for receiving the guide member placement devices 10, 1910, the sling application devices 710, 810, 910, 1010, or the detachable member sling application devices 1410 described above.

Additionally, the balloon catheters 536, 1536, 1636 of the present invention can also be used to create the opening or pocket in the tissue between the urethra and the upper vaginal wall in transvaginal incontinence treatments. In such transvaginal procedures the balloon catheter is inserted through the upper vaginal wall into the area in which the opening or pocket is to be made. The balloon is then expanded, creating the opening or pocket for receiving a sling. In some instances, the physician may use the balloon catheters in conjunction with transvaginal bone anchor implantation devices such as those disclosed in the copending U.S. patent application Ser. No. 08/744,439 entitled "Transvaginal Anchor Implantation Device", filed Nov. 8, 1996, the disclosure of which is incorporated herein by reference. However, use of the balloon catheters in conjunction with transvaginal bone anchor implantation devices may impact the expense of such procedures.

The balloon catheters described above and depicted in FIGS. 2B and 82–86 may be introduced into the body in a number of ways. In one method a needle or guide member is inserted into the hiatal tissue to the desired location. The needle or guide member is inserted into the guide lumen of the catheter. The catheter is advanced along the guide member or needle to the desired location. A syringe filled with saline or sterile water is attached to the luer tip at the end of the catheter and the plunger of the syringe is depressed, ejecting the fluid from the syringe and causing the balloon to inflate. The inflated balloon dilates or tears the tissue thereby creating a shallow opening or pocket adapted to receive a sling.

In an alternate procedure, a hollow needle or trocar is introduced into the body tissue and advanced to the desired location. A balloon catheter, which may have a single inflation lumen, is passed through the lumen of the needle or trocar and advanced to the end. The needle or trocar is partially withdrawn from the patient's body to expose the balloon. The balloon is inflated and deflated as described above to create an opening or pocket adapted to receive a sling.

Further aspects of the present invention relate to tissue expanders 1710 for expanding an opening or pocket in a body tissue and grasping devices 1810 for grasping a suture advanced into the opening or pocket.

In general, the tissue expander comprises a tube with a lumen extending therethrough, an expandable and collapsible member attached to the tube for insertion into the opening within the body tissue and expansion thereof, and an expansion and collapse control in communication with the expandable and collapsible member for moving the expandable and collapsible member between a first position in which it is collapsed and a second position in which it is expanded.

Figure 87:
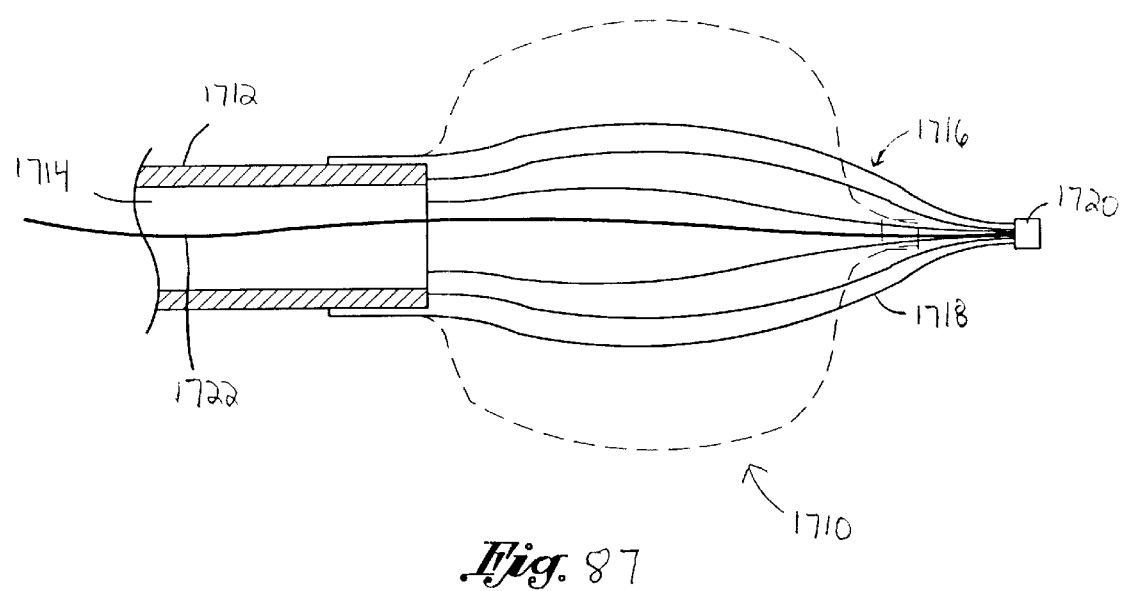
FIG. 87 is a cross-sectional view of a tissue expander.

One embodiment of a tissue expander 1710 according to the present invention is shown in FIG. 87. The tissue expander comprises a tube 1712 with a lumen 1714 extending therethrough. Preferably, the lumen 1714 of the tube 1712 is of sufficient diameter to permit a visualizer, such as a fiberoptic scope, and a grasping device to be simultaneously housed therein.

An expansion basket 1716 is attached to the tube 1712. Preferably, the expansion basket 1716 comprises a plurality of wires 1718 joined at their distal ends by a tip 1720 which is connected to a pull wire 1722. The expansion basket 1716 is movable between a first position in which it is collapsed (indicated with solid lines) and a second position in which it is expanded (indicated with dashed lines) as shown in FIG. 87. When the pull wire 1722 is pulled towards the proximal end of the device, the expansion basket 1716 moves to the expanded position. When the pull wire 1722 is released, the expansion basket 1716 collapses.

The expansion basket 1716 may be fabricated from a variety of materials such as stainless steel or Nitinol. Preferably, the expansion basket 1716 is made of stainless steel.

The expansion basket 1716 may expand the tissue from about 0.25 inch to about 1.5 inches. Preferably, the expansion basket 1716 expands the tissue from about 0.5 inch to about 1.25 inches. In a highly preferred embodiment, the expansion basket 1716 expands the tissue about one inch.

In an alternative embodiment of the tissue expander, a self-expanding net or a self-expanding mesh tube may be used in place of the expansion basket.

A further aspect of the present invention relates to a grasping device which is adapted to fit inside the lumen of the tube of the tissue expander described above. When inserted into the lumen of the tube of the tissue expander, the grasping device is axially movable and extendable from and retractable in the lumen of the tube. Generally, the grasping member comprises a catheter with a grasper on its distal end.

Figure 88:
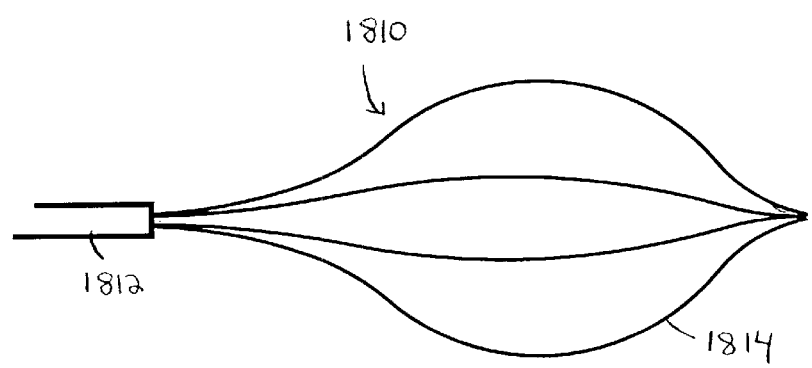
FIG. 88 is a side view of a grasping device.

A grasping device 1810 according to the present invention is shown in FIG. 88. The grasping device 1810 comprises an elongate member 1812 and self-expanding grasping basket 1814 attached to the distal end of the elongate member 1812.

Preferably, the grasping device 1810 is adapted to fit inside the tube 1712 of the tissue expander 1710. When the self-expanding grasping basket 1814 is inside the lumen of the tube 1712 of the tissue expander 1710, it is held in a collapsed configuration by the tube 1712. However, when the self-expanding grasping basket 1814 is extended outside the tube 1712, it expands. Preferably, in its expanded state, the self-expanding grasping basket 1814 on the grasping device 1810 fits inside the expansion basket 1716 of the tissue expander 1710. When the grasping device 1810 is retracted back into the lumen 1714 of the tube 1712 it collapses.

The above grasping devices 1810 and tissue expanders 1710 can be used in a wide variety of surgical procedures in which it is necessary to expand an opening in a body tissue and grasp a suture which has been advanced into the expanded opening. For illustrative purposes, the use of the above devices in a hiatal bladder neck stabilization procedure is described below.

Figure 89:
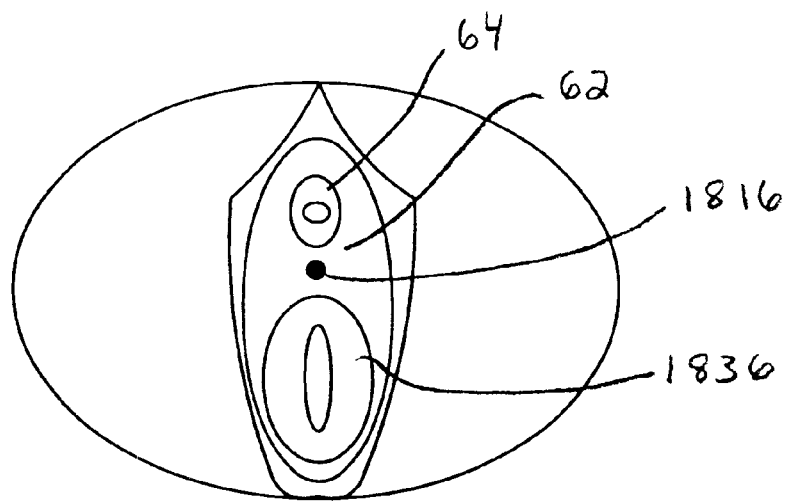
FIG. 89 shows the target site for insertion of a device for creating a lumen in the hiatal tissue between the urethra and the upper vaginal wall.

FIG. 89 shows the urethra 64, the vagina 1836, the hiatal tissue 62 between the urethra and the upper vaginal wall, and a target site 1816 for insertion of a device for creating a lumen 1818 in the hiatal tissue. In the hiatal bladder neck stabilization procedure disclosed herein, the urethra 64 is straightened prior to creation of the lumen 1818 in the hiatal tissue.

Figure 90:
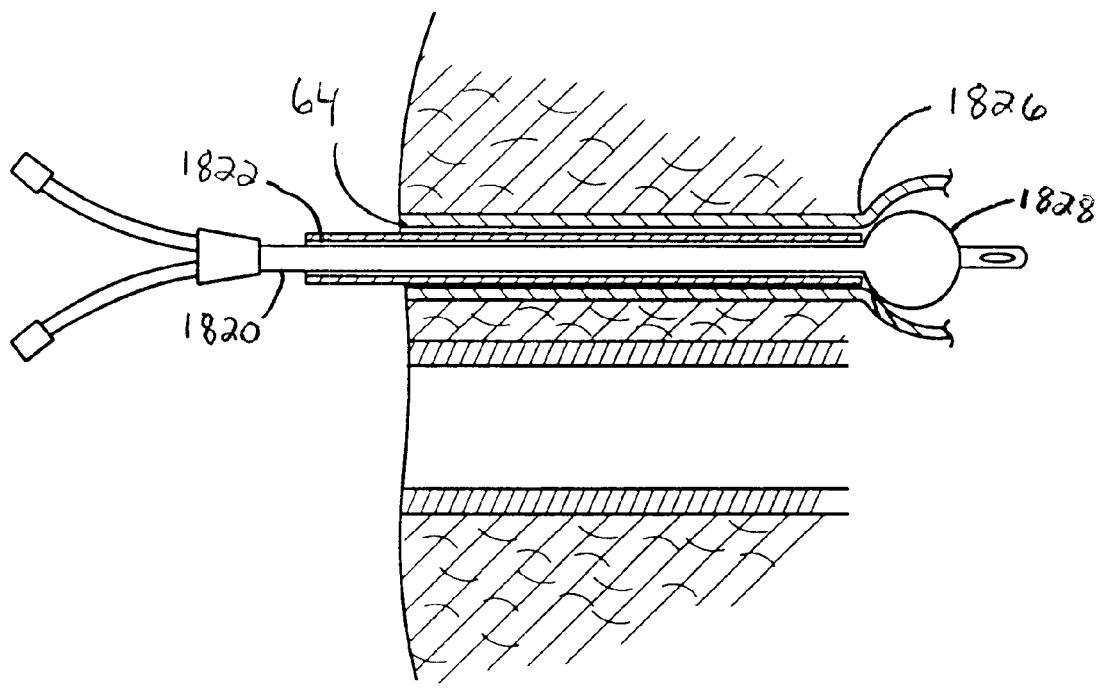
FIG. 90 shows the urethra straightened with a Foley catheter.

As shown in FIG. 90, the urethra 64 can be straightened with a Foley catheter 1820 inside a large bore tube 1822. The large bore tube 1822 fits securely over the Foley catheter and extends out of the urethra. Preferably, the large bore tube is sufficiently firm to rigidify the Foley catheter.

Preferably, the large bore tube 1822 comprises a metal shaft. In a preferred embodiment the metal shaft includes a means to measure the length of the urethra from the bladder neck to the proximal end. In some embodiments, the large bore tube 1822 has guide means thereon which allow the needle 1830 or other dissecting device for dissecting the hiatal tissue, such as a cutter knife, to be guided to the desired site. Such devices are described in the copending U.S. patent application entitled "Method and Apparatus for Minimally Invasive Pelvic Surgery," (VESITEC.028A) filed simultaneously herewith, and the identically titled U.S. Provisional Patent Application Serial No. 60/038,380, filed Feb. 13, 1997, the disclosures of which are incorporated herein by reference.

As shown in FIG. 90, the Foley catheter 1820 is inserted into the urethra 64 and advanced to the bladder neck 1826. When the balloon 1828 of the Foley catheter is inside the bladder neck 1826, it is inflated. Alternatively, the urethra 64 may be straightened with a urethroscope or by other methods familiar to those skilled in the art.

Figure 91:
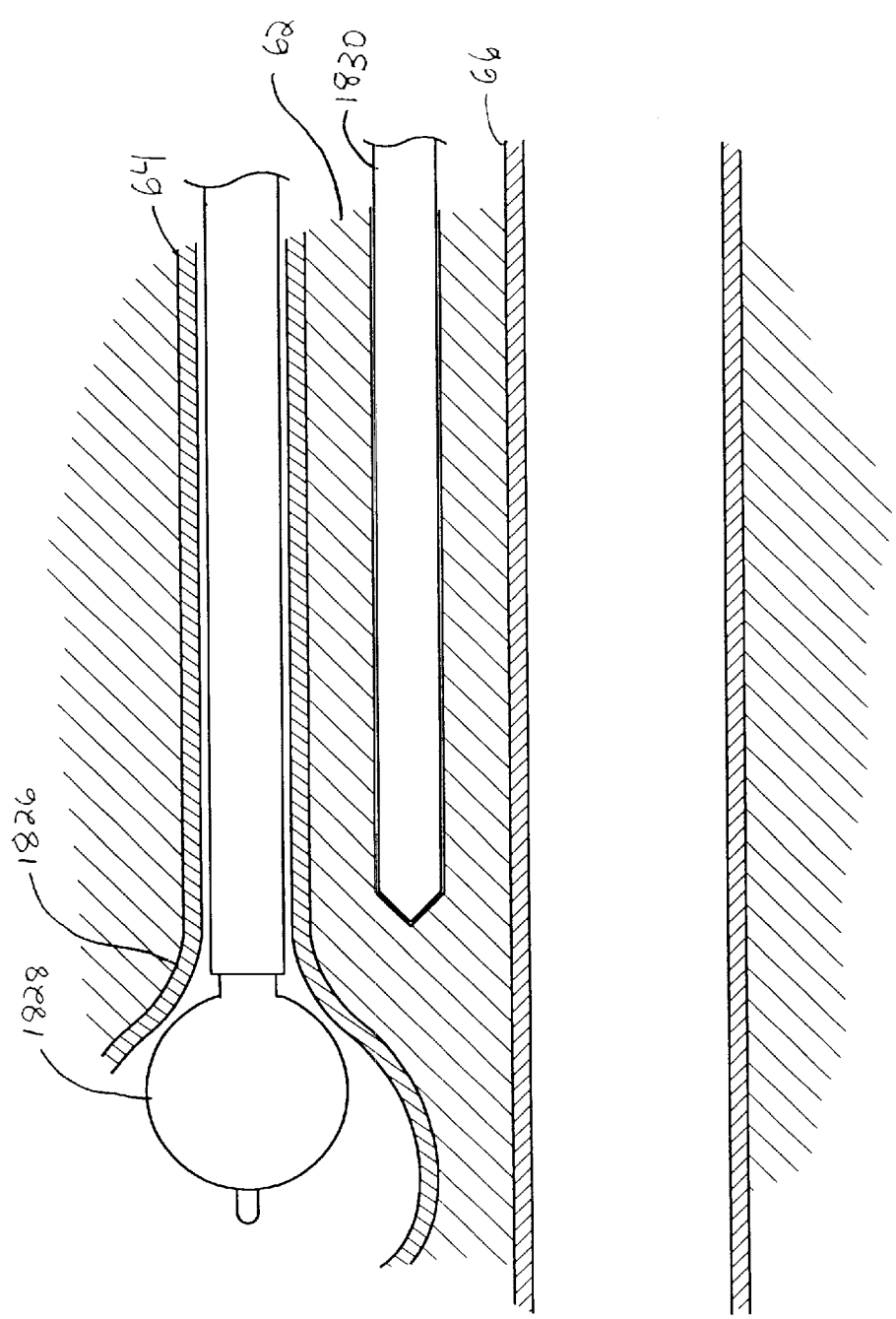
FIG. 91 shows a large bore needle being inserted into the hiatal tissue between the urethra and the upper vaginal wall.

As shown in FIG. 91, a large bore needle 1830 is inserted into the hiatal tissue 62 between the urethra 64 and the upper vaginal wall 66 at the target site 1816 indicated in FIG. 89. An appropriately sized needle may be selected by measuring the distance between the balloon 1828 of the Foley catheter 1820, which is positioned at the bladder neck 1826, and the external urethra. The needle should be slightly shorter than the measured length. For example, the needle may be approximately 0.25 inch less than the measured length.

The needle 1830 may be guided by eye or may be mechanically guided to penetrate the hiatal tissue parallel to the without penetrating the upper vaginal wall. The needle is advanced parallel to the urethra 64 below the midline of the urethra.

Figure 92:
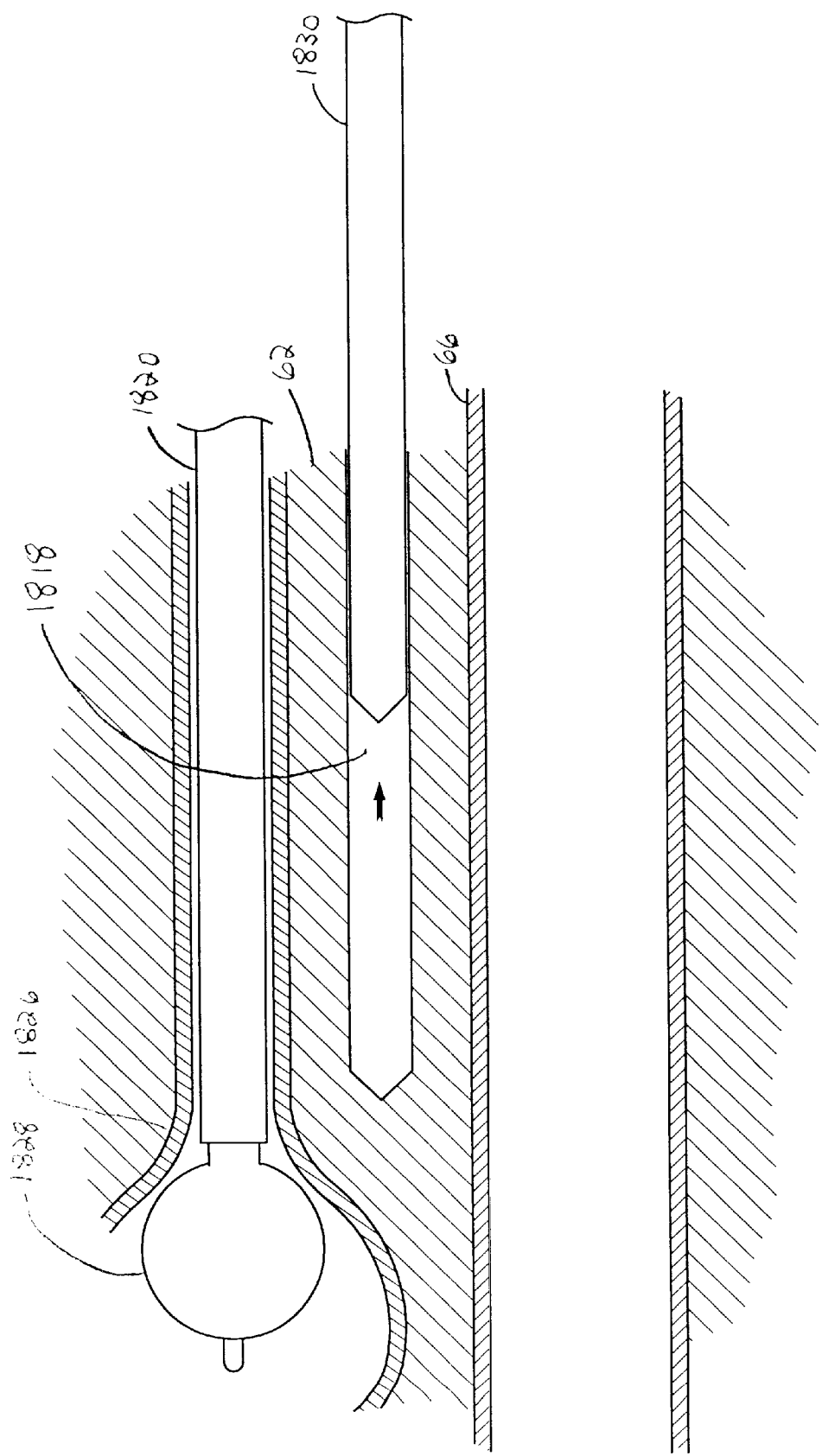
FIG. 92 shows the needle partially retracted such that the lumen created by the needle provides an access channel.

As shown in FIG. 92, the needle 1830 is partially retracted and the lumen 1818 in the hiatal tissue 62 which was created by the needle 1830 provides an access channel for the devices discussed above.

Alternatively, a bi-polar RF cutter may be used to dissect an opening in the hiatal tissue. The bi-polar cutting device comprises a pair of wires, one flexible and one rigid, for cutting a slot from the proximal portion of the hiatus to the bladder neck having a width adapted for receiving a sling therein. Preferably, the bi-polar cutting devices uses 80 Watts of power to cut and coagulate the tissue. In this embodiment, the large bore tube 1822 in which the Foley catheter is placed has a series of thermistors and associated connectors which provide temperature feedback for use in conjunction with a bi-polar RF cutter device. Such devices are described in the copending U.S. patent application entitled "Method and Apparatus for Minimally Invasive Pelvic Surgery" (VESITEC.028A) filed simultaneously herewith, and the identically titled U.S. Provisional Patent Application Serial No. 60/038,380, filed Feb. 13, 1997, the disclosures of which are incorporated herein by reference.

Figure 93:
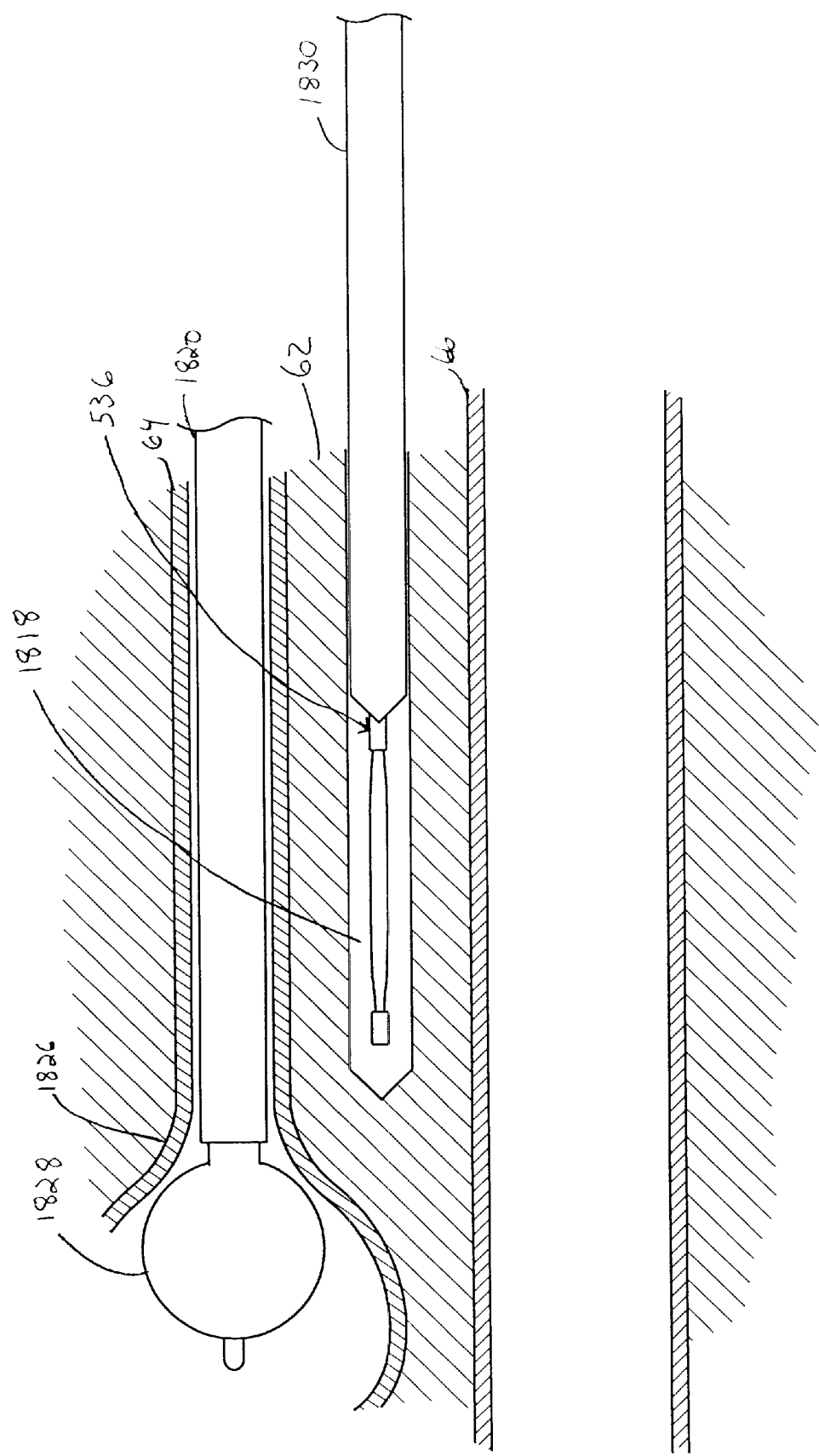
FIG. 93 shows a balloon catheter being advanced beyond the tip of the needle into the lumen created in the hiatal tissue.

A balloon catheter 536 is inserted into the bore of the needle 1830 and advanced beyond the tip of the needle 1830 into the lumen 1832 in the hiatus as shown in FIG. 93. Although FIG. 93 shows the balloon catheter 536 depicted in FIG. 26 being used, the balloon catheters 1536 and 1636 depicted in FIGS. 82–86 may also be used.

Figure 94:
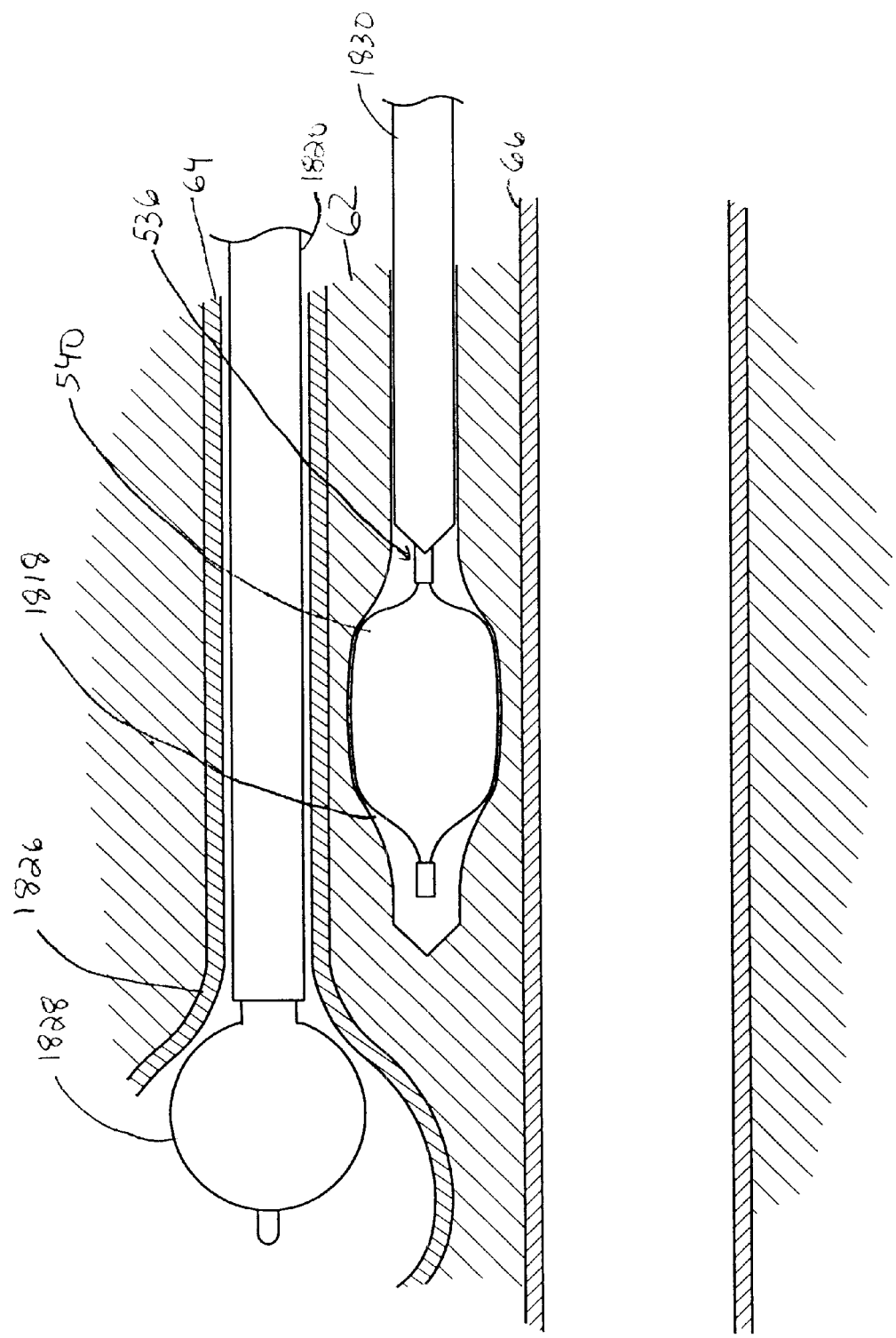
FIG. 94 shows the balloon of the balloon catheter being inflated to dilate the tissue around the lumen created in the hiatal tissue.

As shown in FIG. 94, the balloon 540 is then inflated with saline or sterile water, dilating the hiatal tissue 62 around the lumen 1818 created by the large bore needle 1830. The balloon 540 is then deflated and the balloon catheter 536 is withdrawn from the patient's body.

Figure 95:
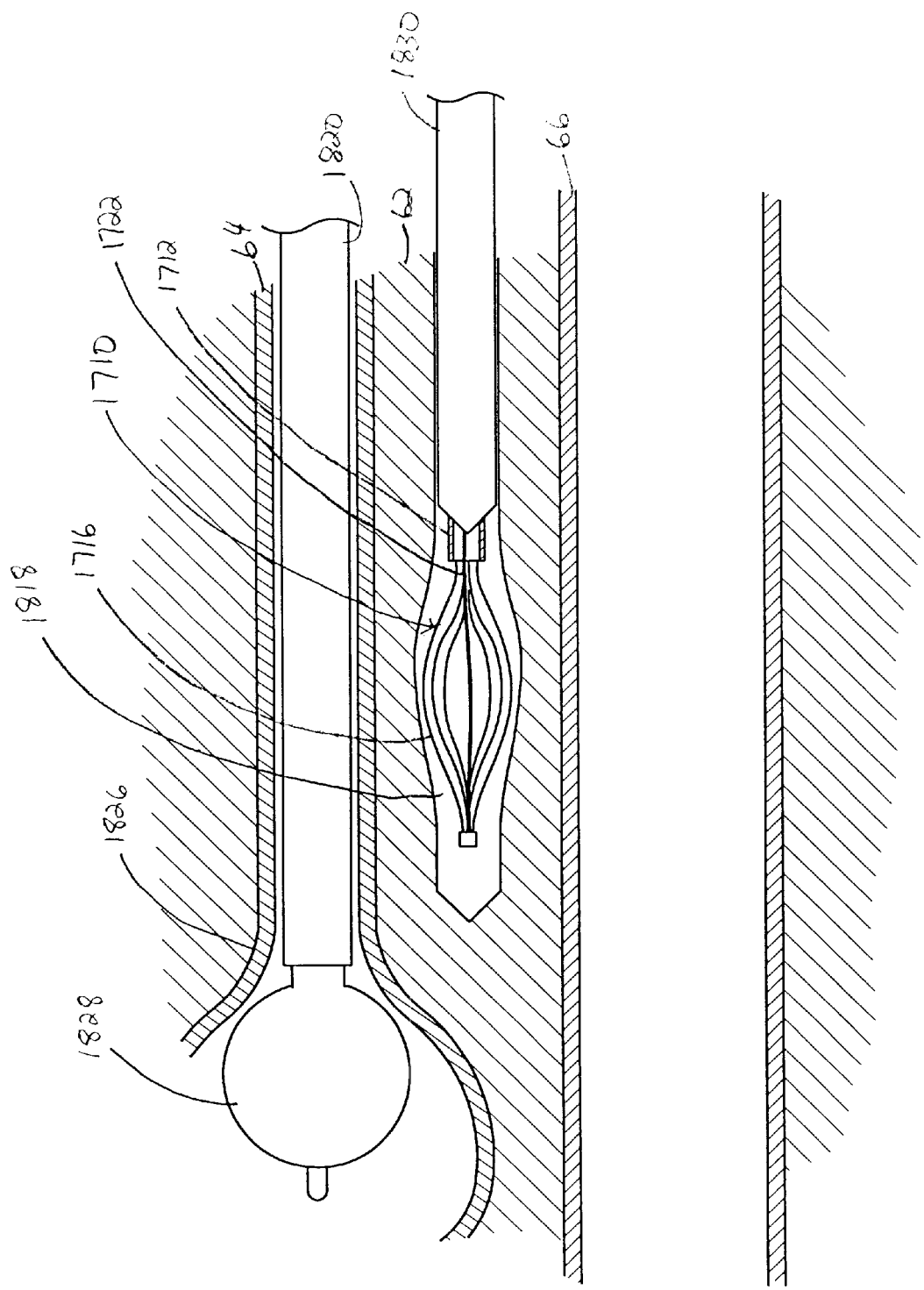
FIG. 95 shows the tissue expander being advanced beyond the tip of the needle into the lumen created in the hiatal tissue.
Figure 96:
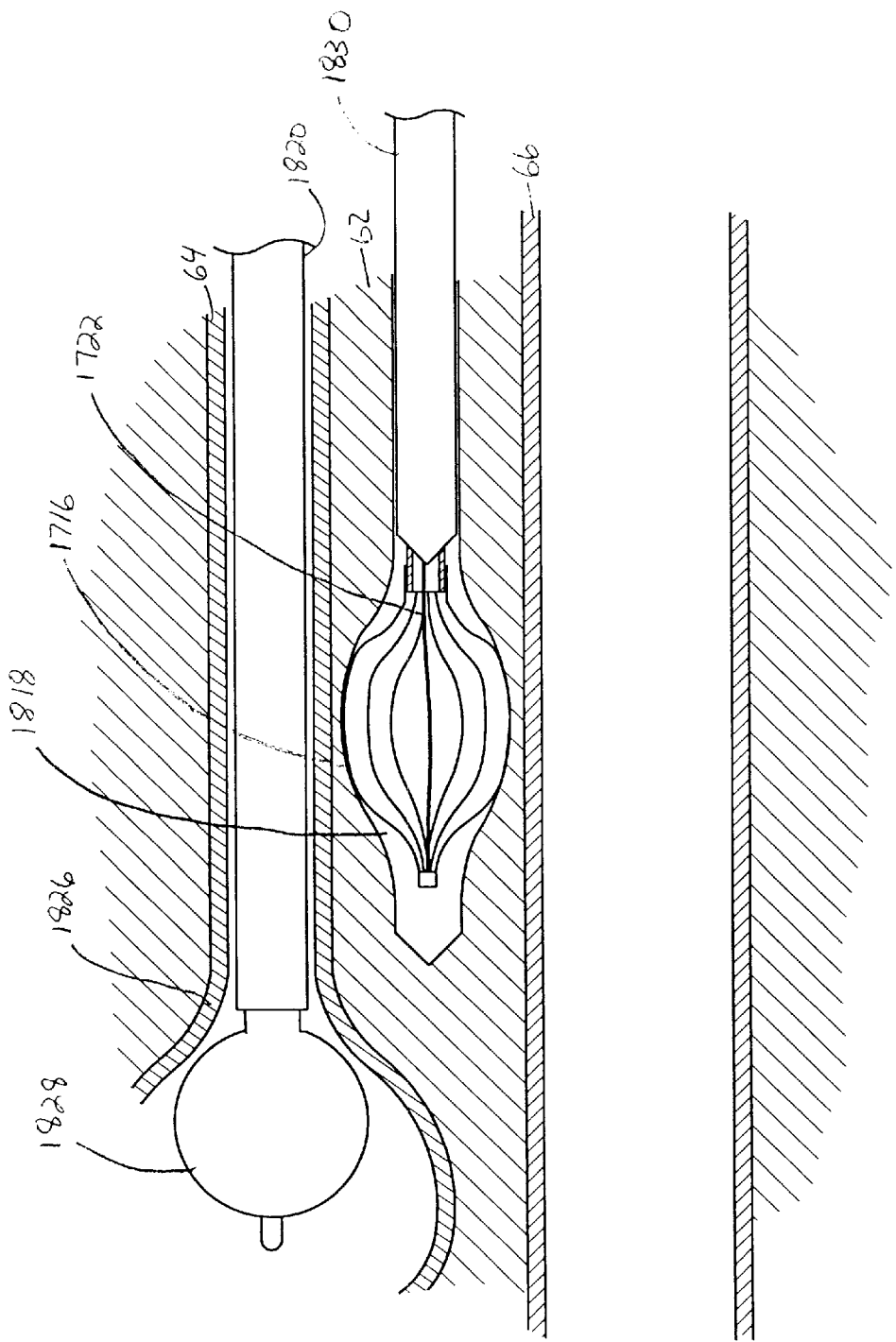
FIG. 96 shows the tissue expander in the expanded configuration within the lumen created in the hiatal tissue.

The tissue expander 1710 is inserted into the large bore of the needle 1830 and advanced beyond the tip of the needle into the lumen 1818 in the hiatal tissue 62, as shown in FIG. 95. The pull wire 1722 is then pulled towards the proximal end of the tissue expander 1710, causing the expansion basket 1716 to adopt the expanded configuration and thereby expanding the lumen 1818 in the hiatal tissue as shown in FIG. 96.

A fiberoptic scope 1832 is inserted into the tube 1712 of the tissue expander 1710 and is extended into the interior of the expansion basket 1716.

Figure 97:
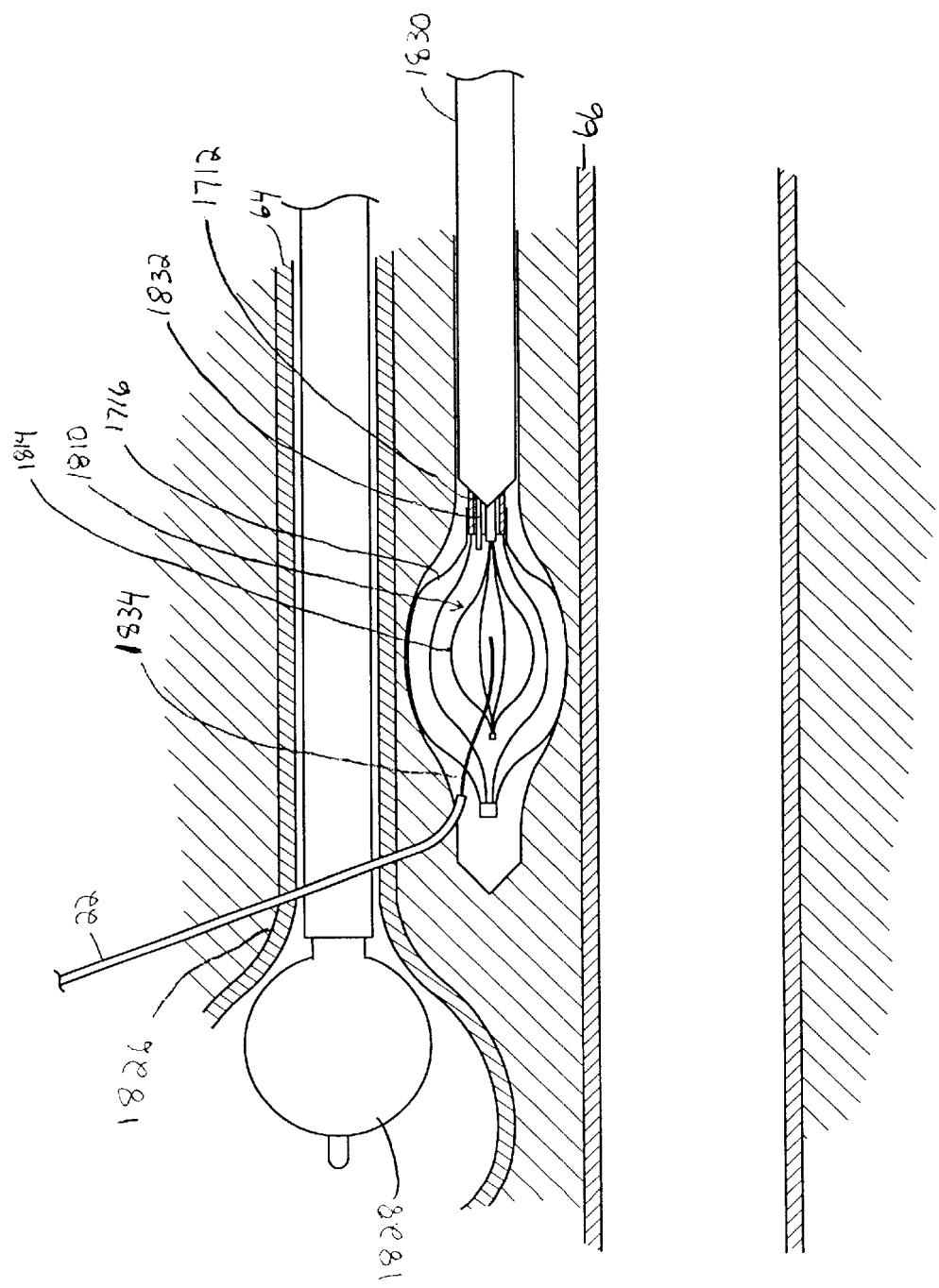
FIG. 97 shows a suture passing through the expansion basket of the tissue expander and into the self expanding basket of the grasping device.

A guide member placement device 10 such as that described above is used to advance a suture 1834 or guide member from a suprapubic incision, along the back side of the pubic bone toward the upper vaginal wall. The suture 1834 or guide member is extended into the expansion basket 1716 of the tissue expander 1710 as shown in FIG. 97. The fiber optic scope 1832 permits the physician to visualize the position of the suture 1834 or guide member in order to determine when the suture 1834 or guide member is within the expansion basket 1716.

Figure 98:
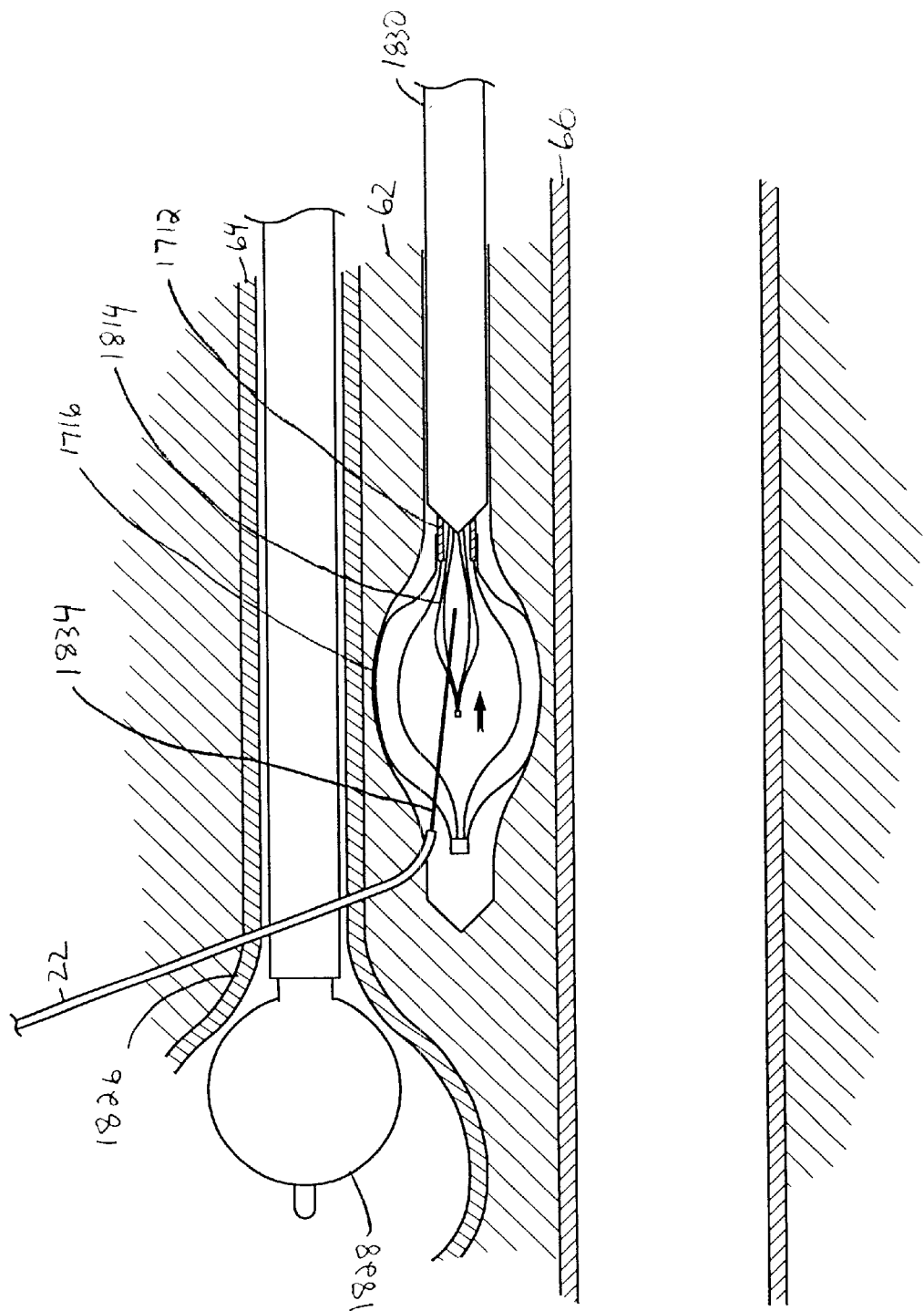
FIG. 98 shows the grasping device grasping the suture.
Figure 99:
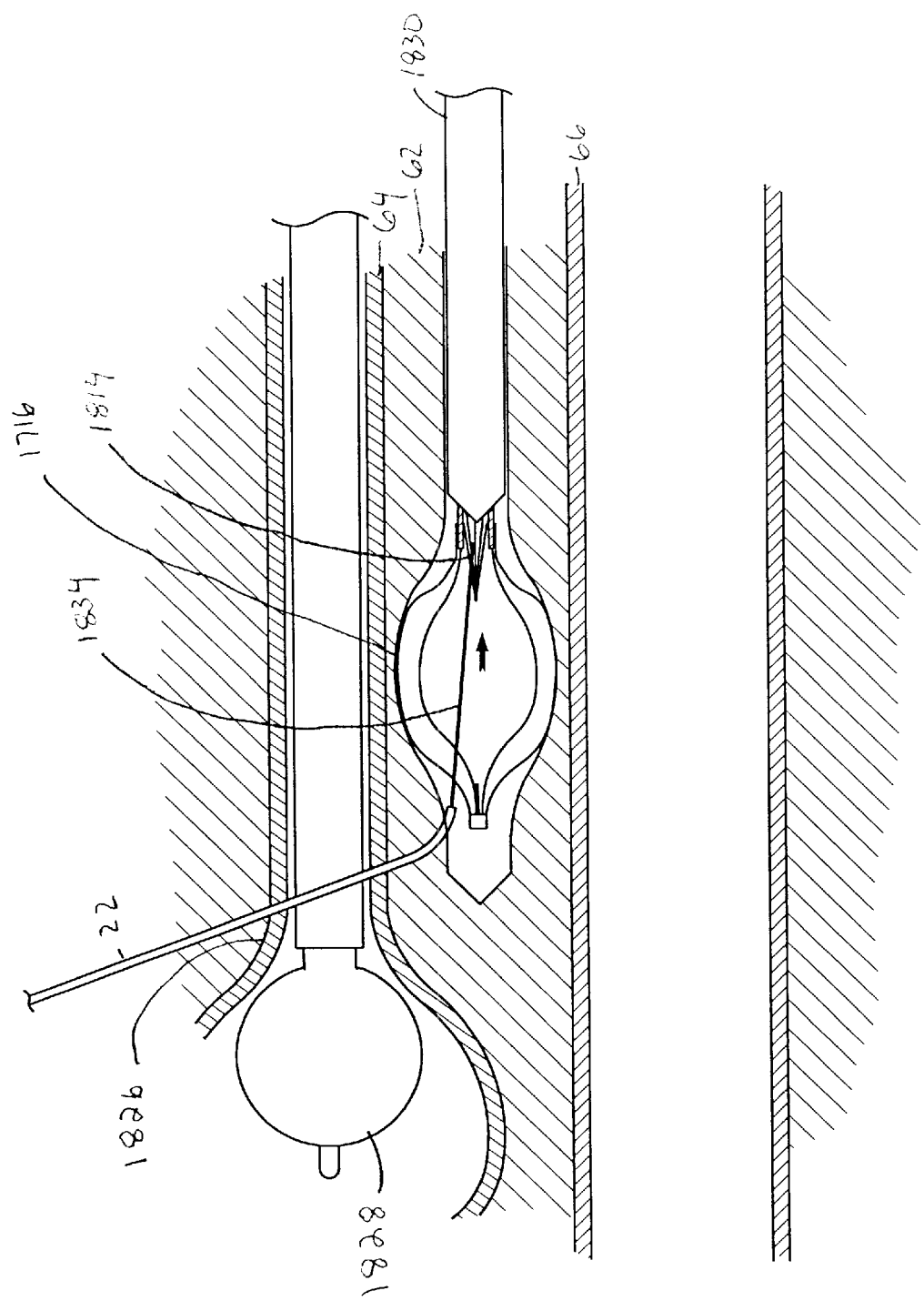
FIG. 99 shows the grasping device being withdrawn from the rigid tube and drawing the suture towards the outside of the patient's body.

A grasping device 1810 is inserted into the lumen 1714 of the tube 1712 of the tissue expander 1710. The self-expanding grasping basket 1814 of the grasping device is extended from the tube 1712, causing the self-expanding basket 1814 to expand, as shown in FIG. 97. The suture 1834 or guide member 68 is positioned inside the self-expanding basket 1814 and the self-expanding basket 1814 is pulled back into the lumen 1714 of the tube 1712, causing the self-expanding basket 1834 to collapse and grasp the suture 1834 or guide member, as shown in FIG. 98. As shown in FIG. 99, the self expanding basket 1814 is withdrawn through the tube 1712, drawing the suture toward the outside of the patient's body. The grasping device 1810 is removed from the tube 1712, pulling the suture 1834 outside the patient's body.

A second suture is advanced along the back side of the pubic bone toward the upper vaginal wall with a guide member placement device as described above. The second suture is positioned on the opposite side of the urethra from the first suture and is advanced into the expansion basket, grasped with the grasping basket, and drown outside the patient's body as described above. Following this procedure, a second suture or guide member extends from the patient's body.

The large bore needle 1830 and tissue expander 1710 are then removed from the patient's body. The ends of the two sutures are knotted together and the ends of the knotted suture extending from the suprapubic incisions are pulled to draw the knotted suture back into the body. The knot is advanced out of one of the suprapubic incisions providing an uninterrupted suture or guide member extending between the suprapubic incisions around the urethra. The suture provides a guide path from the suprapubic incisions around the urethra which may be used to introduce a sling using a sling introduction catheter as described above.

In an alternative embodiment, the large bore needle 1830 is left in place. A sling is secured to the sutures outside the body, rolled or restuffed, and then drawn through the bore of the needle and into the opening or pocket in the body tissue by pulling on the ends of the sutures extending from the suprapubic incisions.

The tension on the sling may be adjusted as described above. Bone anchors or other means may be used to secure the sutures as discussed above to support the bladder neck or stabilize the urethral floor, thereby maintaining or improving urinary continence.

Although this invention has been described in terms of certain preferred embodiments, other embodiments which will be apparent to those of ordinary skill in the art in view of the disclosure herein are also within the scope of this invention. Accordingly, the scope of the invention is intended to be defined only by reference to the appended claims. In addition, for clarity, letter references are used in some of the claims. These letter references, however, are not meant to imply any particular order for performing the method steps.

What is claimed is:

1. A guide member placement device for inserting a guide member into a body tissue, comprising:
   a handle including a distal end, a proximal end, and a lumen extending therethrough;
   a rigid shaft including a proximal end, a distal end, and a lumen extending therethrough, the proximal end of the shaft being attached to the distal end of the handle such that the lumens extending through the handle and the shaft are aligned; and
   an engaging member disposed near the distal end of the shaft, wherein the engaging member is adapted to engage a second guide member placement device.

2. The guide member placement device of claim 1, wherein the guide member placement device is adapted for use in urethral floor reconstruction procedures.

3. The guide member placement device of claim 1, wherein the guide member placement device is adapted for use in bladder neck stabilization procedures.

4. The guide member placement device of claim 1, wherein the engaging member comprises a male connector adapted to be releasably couple to the female connector on the second guide member device.

5. The guide member placement device of claim 1, wherein the engaging member comprises a female connector adapted to be releasably couple to the male connector on the second guide member device.

6. The guide member placement device of claim 1, wherein the shaft includes a straight proximal section, a bent intermediate section and a distal section, the distal section being oriented at an angle of approximately 90 degrees relative to the proximal section.

7. The guide member placement device of claim 1, further comprising a guide member removably positioned in the lumen of the shaft.

8. The guide member placement device of claim 7, wherein the guide member comprises a guidewire.

9. The guide member placement device of claim 7, wherein the guide member comprises a suture.

10. The guide member placement device of claim 1, further comprising an axially-movable blunt dissection tip positioned near the distal end of the shaft.

11. The guide member placement device of claim 10, wherein the blunt dissection tip is positioned on a blunt dissector disposed within the lumen of the shaft, the blunt dissection tip being extendable from and retractable into the shaft.

12. The guide member placement device of claim 11, wherein the blunt dissector is biased toward a retracted position.

13. The guide member placement device of claim 10, wherein the blunt dissector comprises a narrow portion including a lumen, the narrow portion being connected to a body portion located within the handle.

14. The guide member placement device of claim 13, wherein the body portion of the blunt dissector comprises a recessed portion and a spring, the recess portion being adapted for receiving the spring which biases the blunt dissector toward the retracted position.

15. The guide member placement device of claim 13, further comprising a rotatable cam adapted to place axial distal force upon the body portion of the blunt dissection to thereby place blunt dissector tip in the extended position.

16. The guide member placement device of claim 13, wherein the body portion of the blunt dissector comprises a lumen which is in fluid communication with a lumen disposed in the narrow portion of the blunt dissector.

17. The guide member placement device of claim 13, wherein the body portion of the blunt dissector has an axial range of motion from about 2 mm to about 10 mm.

18. The guide member placement device of claim 13, wherein the mounting support includes a proximal endwall which limits the distal travel of the body portion of the blunt dissector.

19. The guide member placement device of claim 10, wherein the handle includes a proximal endwall which limits the proximal travel of the body portion of the blunt dissector.

20. The guide member placement device of claim 1, wherein the shaft and the handle are oriented along a common longitudinal axis.

21. The guide member placement device of claim 1, wherein the blunt dissector comprises a semi-elastic metal material.

22. The guide member placement device of claim 1, wherein at least part of the exterior surface of the handle is textured to produce a high-friction gripping surface.

23. The guide member placement device of claim 1, wherein the handle comprises a gripping area and a mounting support.

24. The guide member placement device of claim 23, wherein the gripping area comprising a hollow tubular body including a proximal endwall and a distal endwall.

25. The guide member placement device of claim 24, wherein the mounting support includes a distal end and a proximal end, and the proximal end of the mounting support extends into the hollow tubular body of the handle.

26. The guide member placement device of claim 25, wherein the proximal end of the shaft is secured to the distal end of the mounting support.

27. The guide member placement device of claim 1, wherein the distal end of the shaft is oriented at an angle of approximately 90° relative to the handle.

* * * * *